United States Patent
Pathak

(10) Patent No.: US 9,072,678 B2
(45) Date of Patent: Jul. 7, 2015

(54) METHODS FOR LOCAL DRUG DELIVERY BY MICROINJECTION

(71) Applicant: Pathak Holding, LLC, Phoenix, AZ (US)

(72) Inventor: Chandrashekhar P. Pathak, Pheonix, AZ (US)

(73) Assignee: Pathak Holdings LLC, Phoenix, AZ (US)

( * ) Notice: Subject to any disclaimer, the term of this patent is extended or adjusted under 35 U.S.C. 154(b) by 0 days.

(21) Appl. No.: 14/209,827

(22) Filed: Mar. 13, 2014

(65) Prior Publication Data

US 2014/0271897 A1 Sep. 18, 2014

Related U.S. Application Data

(60) Provisional application No. 61/786,215, filed on Mar. 14, 2013, provisional application No. 61/820,449, filed on May 7, 2013, provisional application No. 61/946,825, filed on Mar. 2, 2014, provisional application No. 61/934,795, filed on Feb. 2, 2014.

(51) Int. Cl.

| | |
|---|---|
| A61F 2/02 | (2006.01) |
| A61K 9/50 | (2006.01) |
| A61K 31/496 | (2006.01) |
| A61K 31/7036 | (2006.01) |
| A61L 31/16 | (2006.01) |
| A61K 9/00 | (2006.01) |
| A61K 9/16 | (2006.01) |
| A61K 31/155 | (2006.01) |
| A61K 31/337 | (2006.01) |
| A61K 31/727 | (2006.01) |
| A61M 37/00 | (2006.01) |
| A61M 5/30 | (2006.01) |

(52) U.S. Cl.
CPC ............. *A61K 9/5031* (2013.01); *A61K 31/496* (2013.01); *A61K 31/7036* (2013.01); *A61L 31/16* (2013.01); *A61K 9/0024* (2013.01); *A61K 9/1694* (2013.01); *A61K 9/0021* (2013.01); *A61K 9/1647* (2013.01); *A61K 9/5089* (2013.01); *A61K 31/155* (2013.01); *A61K 31/337* (2013.01); *A61K 31/727* (2013.01); *A61M 5/3015* (2013.01); *A61M 2205/3606* (2013.01); *A61M 2205/3653* (2013.01); *A61M 37/0076* (2013.01); *A61M 2037/0023* (2013.01)

(58) Field of Classification Search
CPC .... A61L 31/16; A61K 9/0024; A61K 9/1647; A61K 9/1694
See application file for complete search history.

(56) References Cited

PUBLICATIONS

Hickerson et al, "Gene Silencing After Deposition of Seld-Delivery siRNA With a Motorized Microneedle Array Device", Mol. Ther Nucleic Acid, v 2(10), Oct. 2013.*
Bauman et al, "An Injectable Platform for Sustained Combination Therapy", Journal of COntrolled Release (2009).*

* cited by examiner

*Primary Examiner* — Carlos Azpuru
(74) *Attorney, Agent, or Firm* — Maschoff Brennan, PLLC

(57) ABSTRACT

This invention provide novel compositions, methods and devices for sustained drug delivery. The microencapsulated sustained drug delivery compositions are deposited using oscillating needle apparatus oscillating at 10-12000 minutes per minutes. The injected compositions may undergo variety of physical chemical changes upon deposition. The physical and chemical changes enables improved drug encapsulation and sustained drug release. Also described are new methods to form polymer microparticles or polymer films/implants in situ inside the tissue. The invention also describes colored biodegradable microparticle based compositions wherein the compositions comprise drug encapsulated microparticles and coloring agent encapsulated microparticles mixed in any proportion. Medical applications of the compositions and methods described in this invention are also described.

9 Claims, 32 Drawing Sheets

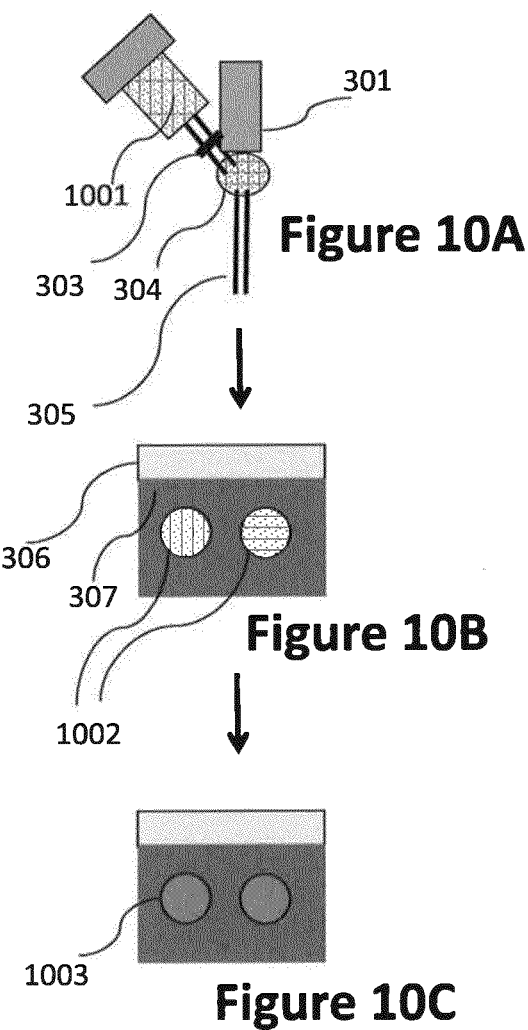

METHODS FOR LOCAL DRUG DELIVERY BY MICROINJECTION

CROSS-REFERENCE TO RELATED APPLICATIONS

This application claims priority to each of U.S. Provisional Patent Application No. 61/786,215 filed Mar. 14, 2013; U.S. Provisional Patent Application 61/820,449 filed May 7, 2013; U.S. Provisional Patent Application 61/946,825 filed Mar. 2, 2014, and U.S. Provisional Patent Application 61/934,795 filed Feb. 2, 2014, each of these provisional applications being herein incorporated by specific reference in their entirety for all purposes.

FIELD OF THE INVENTION

This invention generally relates to compositions, methods and devices for drug delivery. More particularly, the invention relates to compositions, methods and devices for local, sustained drug delivery, wherein such compositions comprise of drug encapsulated microparticles that are made or implanted in situ and delivered in a controlled manner. The drug microparticles may be encapsulated in a biodegradable polymer and may also include a colored or fluorescent additive to aid in visualization during the drug delivery. The present invention also relates to methods and devices for preparation and delivery of such compositions. The invention aims to achieve precise control over the drug dose to help reduce unwanted side effects of a drug and is useful to deliver pain medications, for delivery of drugs that need to be delivered at very low dosage, for biodegradable tattoos, and for a wide range of surgical, cosmetic or therapeutic procedures wherein it is possible to view the location of delivery of the injectable composition by the naked eye.

BACKGROUND

Microencapsulation of drugs in biodegradable microparticles or microspheres is a well known pharmaceutical dosage preparation art. U.S. Pat. No. 6,599,627 cited herein for reference only; discloses one of the several ways known in prior art to prepare biodegradable microspheres for sustained drug delivery. The encapsulated drug particles can release a drug in a sustained manner ranging from few days and weeks to several months. However synthesizing microencapsulated drugs requires several chemical and physical steps, which leads to increased cost of preparation. The high surface area of such biodegradable microspheres also makes them more susceptible to bacterial contamination during preparation and uses. None of the known prior art references disclose methods of preparation of microspheres or microparticles or compositions of such microspheres or microparticles which are made in-situ and delivered during a surgical procedure and not in a factory setting.

BRIEF SUMMARY OF THE INVENTION

The present invention addresses the foregoing need for compositions, methods and devices for local sustained drug delivery. Such compositions are infused in the body tissue in the form of microparticles incorporating one or more of a drug, a biodegradable polymer and a visualization agent. The present invention is also directed towards methods for synthesizing such drug bearing microparticles in situ by using devices incorporating an oscillating needle. Accordingly, there is a need for such compositions, methods and devices as summarized herein in some detail.

It is therefore an embodiment of the present invention to provide a tattoo ink composition, wherein the composition comprises of a visualizing agent and a drug for local sustained drug delivery. The tattoo ink can be degradable so that the visibility of the color fades from the skin after injection into skin of a subject.

Another embodiment of the present invention to provide a method for delivering a bioactive agent (e.g., drug) composition for local site inside the human or animal body, in a precisely controlled manner. A further embodiment of the present invention to provide a method for producing drug bearing microparticles encapsulated in a biodegradable polymer in situ in the tissue. A still further embodiment of this invention is to provide a method to release a drug wherein the microencapsulated drug particle are injected in a bioprosthesis surface or in a live tissue surface and their delivery can be visualized during or after the injection. A further embodiment of the present invention to provide a method for producing water insoluble drug bearing microparticles in situ in the tissue. A further embodiment of the present invention to provide a method for producing drug bearing microparticles in a low melting polymer or non-polymer carrier in situ in the tissue. A further embodiment of the present invention to provide an injectable liquid based sustained delivery composition, wherein the injectable composition comprises of precursors of crosslinkable composition to form crosslinked microparticles in situ inside the tissue. A further embodiment of the present invention to provide a method for making sustained releasing gel particles in situ inside the tissue wherein the injectable composition comprises of thermoreversible gel composition in a fluid state. A further embodiment of the present invention to provide a method for making silver ion releasing gel particles in situ inside the tissue wherein the injectable composition comprises of an injectable silver salt solution. A further embodiment of the present invention to provide a device for injecting an injectable fluid composition such that the composition is delivered in the tissue at an oscillation rate of 10 to 12000 oscillations per minute. A further embodiment of the present invention to provide a device for injecting an injectable fluid composition such that the composition is deposited in situ at injection volume of 1.0E-02 ml to 1.0E-16 ml per injection. A further embodiment of the present invention to provide a device for injecting an injectable fluid composition such that the flow and temperature of the injectable composition can be controlled by the user. Yet another embodiment of the invention is to provide a method for infusion of sustained drug delivery injectable compositions over an area greater than 2 mm square, injected using at least 30 number of injections. Yet another embodiment of the invention is to provide a method for sustained drug delivery injectable composition wherein the composition increases its volume by absorbing tissue fluids. To achieve the forgoing and other embodiments and in accordance with the purpose of the invention, a variety of drug delivery compositions, methods and devices thereof are described.

An embodiment of the present invention provides a tattoo ink composition, wherein the composition is colored suspension/solution and a drug for local sustained drug delivery. In the preferred composition the drug is encapsulated in the biodegradable polymer microparticle. An alternate embodiment of the present invention provides a colored pharmaceutical composition wherein a microparticles comprising a drug and microparticles comprising a visualization agent, preferably coloring agent are mixed in any proportion to make a colored or fluorescent sustained drug delivery composition that enables easy visualization.

Another embodiment of the present invention provides a method for delivering a drug composition for local site inside the human or animal body, wherein an oscillating needle is used to deliver the composition. Preferably the needle is oscillating at 10-12000 times per minute. In the preferred compositions, drugs like Botox, insulin, anesthetics, and pain management medications are locally given using oscillating needle device. Another embodiment of the present invention provides a method for delivering a fluid drug composition for local site inside the body, wherein an oscillating needle is used to deliver the composition and the needle delivers 1.0E-02 to 1.0E-16 ml of drug solution/suspension or injectable composition per injection. Another embodiment of this invention provides a method to release a drug wherein the drug particles or microencapsulated drug particle are infused in the bioprosthesis surface using oscillating single or multi-needle injector. In the preferred embodiment, the colored particles are injected for better visualization. Another embodiment of this invention provides fluorescent injectable compositions of Botox or Dysport® or Insulin or other protein drugs wherein fluorescence of the drug composition helps to visualize the injected drug during or after injection.

Another embodiment of this invention provides a method for making biodegradable microparticles in situ inside the tissue. The methods involves following steps: a) provide an injectable composition comprising polymer solution in a water miscible solvent; b) injecting the composition in the tissue using an oscillating needle and c) dispersing the solvent and precipitating/isolating the polymer to form microparticles inside the tissue. Preferably the polymer used is biodegradable. Another embodiment of this invention provides a method for making biodegradable microparticles in situ inside the tissue. The methods involves following steps: a) provide an injectable composition comprising polymer solution in a water miscible solvent; b) injecting the composition in the tissue using at the rate of 1.0E-02 to 1.0E-16 ml per injection and c) dispersing the solvent and precipitating/isolating the polymer to form microparticles inside the tissue. Preferably the polymer used is biodegradable.

Another embodiment of this invention provides a method for making water insoluble drug particles in situ inside the tissue. The method involves following steps: a) provide an injectable composition comprising water insoluble drug solution in a water miscible organic solvent; b) injecting the composition in the tissue using an oscillating needle and c) dispersing the solvent and precipitating the drug crystals/solids inside the tissue. The precipitated drug release the drug by slow dissolution or biodegradation process.

Another embodiment of this invention provides a method for making microparticles in situ inside the tissue. The methods involves following steps: a) provide an injectable composition comprising low melting polymer or non-polymer carrier; b) melting the composition and injecting the melted composition in the tissue using an oscillating needle and c) cooling the melted polymer to form polymer Preferred composition is biodegradable.

Another embodiment of this invention provides a method for making liquid based sustained delivery compositions. The method involves following steps: a) provide an injectable composition comprising drug and polymeric or non-polymeric liquid carrier; b) injecting the drug and liquid carrier composition in the tissue using an oscillating needle and c) providing sustained delivery of drug using injected liquid carrier.

Another embodiment of this invention provides a method for making liquid based sustained delivery compositions. The method involves following steps: a) provide an injectable composition comprising drug and polymeric or non-polymeric liquid carrier; b) injecting the drug and liquid carrier composition in the tissue at the rate of 1.0E-02 to 1.0E-16 ml per injection and c) providing sustained delivery of drug using injected liquid carrier.

Another embodiment of this invention provides a method for making microparticles in situ inside the tissue. The method involves following steps: a) provide an injectable composition comprising precursors of crosslinkable composition; b) injecting the precursors in the tissue using an oscillating needle and c) crosslinking the precursors to form crosslinked microparticles.

Another embodiment of this invention provides a method for making sustained releasing gel particles in situ inside the tissue. The methods involves following steps: a) provide an injectable thermoreversible gelling compositions fluid state; b) injecting thermoreversible gelling fluid compositions in the tissue using an oscillating needle and c) gelling the compositions in situ using thermoreversible property to form gel particles. Another embodiment of this invention provides a method for making silver ions releasing particles in situ inside the tissue. The methods involves following steps: a) provide an injectable silver salt solution; b) injecting silver salt solution in the tissue using an oscillating needle and c) forming silver chloride or other silver salts particles inside the tissue.

Another embodiment of this invention discloses a drug delivery device wherein the device has an oscillating needle that oscillates at the rate of 10 to 12000 oscillations per minute and is used for injecting an injectable/fluid composition. The needle is connected to a reservoir of injectable composition with or without a flow control valve. If used with control valve, the valve can be turned of and on by the user. Optionally the needle and reservoir can be heated or cooled to a desired temperature.

One embodiment of this invention provides novel microparticle based compositions and methods wherein the implanted compositions increase its size volume by absorption of local water or tissue fluids. The increase in size mechanically locks the composition in situ and thus prevents/reduces its movement from the injection site. The preferred compositions are dry or semi-dry hydrogel compositions that absorb water from injected site.

Another embodiment the invention provides a method for infusion of sustained drug delivery injectable compositions over area greater than 2 mm square, injected using at least 30 number of injections. The number of injections can include 30 or more separate injections. Another embodiment the invention provides a method for infusion of sustained drug delivery injectable compositions over area greater than 2 mm square, and injected at the rate of 1.0E-02 to 1.0E-16 ml per injection.

Another embodiment of this invention provides a method for crosslinking tissues. The methods involves following steps: a) provide an injectable solution comprising tissue crosslinker; b) injecting crosslinker solution in the tissue using an oscillating needle wherein the injection volume is less than 1.0E-02 ml per injection and c) incubating the tissue under effective crosslinking condition wherein the tissue is exposed to the injected crosslinker solution and is effectively crosslinked. Preferably the tissue is a corneal tissue.

Another embodiment of this invention provides a method reducing postoperative adhesions. The methods involves following steps: a) provide an injectable solution comprising hyaluronic acid or polyethylene glycol copolymer; b) injecting polymer solution in the affected tissue using an oscillating needle wherein the injection volume is less than 1.0E-02 ml per injection.

Yet another embodiment of the present invention is to provide a method for delivery of injectable compositions wherein it is possible to deliver biodegradable implants, typically having an area greater than 5 mm square without requiring a surgical incision. The inventive method uses fusion/agglomeration of polymer droplet solutions to make the implant in situ.

BRIEF DESCRIPTION OF THE SEVERAL VIEWS OF THE DRAWINGS

FIG. 10A shows a partial schematic representation of an injection device apparatus in an embodiment of the invention wherein the injectable composition comprises of inorganic metal salt solution in a water or water based buffered solution.

FIG. 10B is a schematic representation of the epidermis layer and dermis layers along with injected composition droplets.

FIG. 10C shows a partial schematic representation of the epidermis layer and dermis layers along with injected composition retained at the implanted site for local sustained drug delivery. The injected undergoes chemical reaction with tissue extracellular matrix or tissue fluid components leaving behind precipitated silver salts.

FIGS. 21A through 22D represents a bioprosthesis tissue, a muscular tissue and cornea tissue implanted with biodegradable microparticle composition with rifampin as a drug or fluorescent dye as a visualization agent and/or as a model drug. The fluorescence of tissue embedded composition is clearly seen under blue light.

Figure 1A:
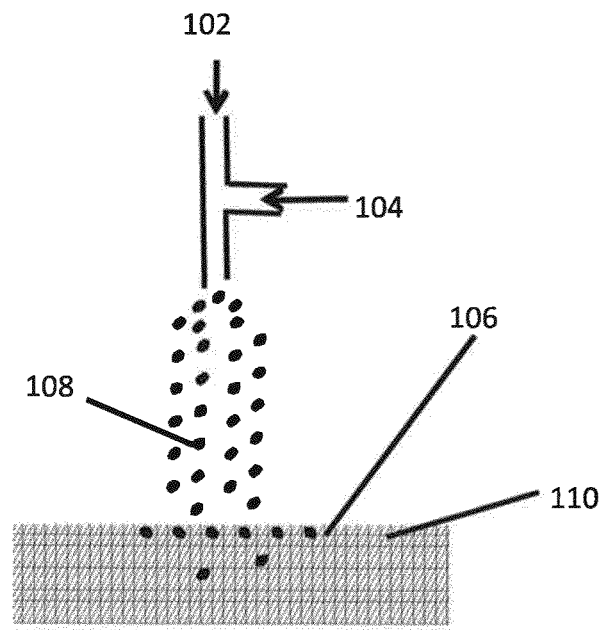
FIG. 1A is a representative diagram illustrating a method for infusing microencapsulated drug bearing particles in the bioprosthetic tissue in an embodiment of the invention wherein the drug particles are fed through a reservoir after being given sufficient kinetic energy using a pressurized means.

The figures are not necessarily drawn to scale unless specifically indicated.

DETAILED DESCRIPTION OF THE INVENTION

It is to be understood that the present disclosure is not limited in its application to the details of construction and the arrangement of components set forth in the following description or illustrated in the drawings. The present disclosure is capable of other embodiments and of being practiced or of being carried out in various ways. Also, it is to be understood that the phraseology and terminology used herein is for the purpose of description and should not be regarded as limiting. Exemplary embodiments of the present invention are directed towards compositions, methods and devices for facilitating local and sustained drug delivery.

It is advantageous to define several terms, phrases and acronyms before describing the invention in detail. It should be appreciated that the following terms are used throughout this application. Where the definition of terms departs from the commonly used meaning of the term, applicant intends to utilize the definitions provided below, unless specifically indicated. The following definitions are provided to illustrate the terminology used in the present invention. Unless defined otherwise, all technical and scientific terms used herein have the same meaning as is commonly understood by one who is skilled in the art. All scientific literature and patent citations in this invention are incorporated herein for reference use only. "Crosslinked material" is meant to denote the formation of intermolecular or intramolecular covalent bonds in the macromolecule or polymer. The crosslinked material may be in a highly hydrated state.

A "crosslinking agent" is defined as a compound capable of forming crosslinked material. For example, glutaraldehyde is generally known in the art as crosslinking agent for the tissue or with albumin or with collagen.

"In situ" is meant to denote at a local site, especially within or in contact with living organisms, tissue, organs, or the body. "Bioprosthesis" is defined to include any prosthesis, which is derived in whole or in part from animal or other organic tissue including cultured tissue and which is suitable for human or animal implantation. Tissue used in bioprosthesis as defined above is generally referred bioprosthetic tissue.

The term "tissue" or "extracellular matrix" (ECM) includes human or animal tissue suitable for implantation in human or animal body. For more specific definition of tissue, tissue as defined in U.S. Pat. No. 7,919,112, cited herein for reference only, may be used.

"Bioactive" refers to one or all of the activities of a compound that show pharmacological or biological activity in human or animal body. Such biological activity is preferred to have a therapeutic effect. Substances or compounds that are bioactive are referred to as "drugs" or "therapeutic agents" or "bioactive agents" or "bioactive compounds" The bioactive compounds that can be used include, but are not limited to, antiviral agents; antiinfectives such as, by way of example, and not limitation, antibiotics; antiviral agents, antifungal agents, antibacterial agents, antipruritics; anticancer agents, antipsychotics; cholesterol- or lipid-reducing agents; cell cycle inhibitors; anticancer agents; antiparkinsonism drugs; HMG-CoA inhibitors; antirestenosis agents; antiinflammatory agents; antiasthmatic agents; anthelmintic; immunosuppressives; muscle relaxants; antidiuretic agents; vasodilators; nitric oxide; nitric oxide-releasing compounds; beta-blockers; hormones; antidepressants; decongestants; calcium channel blockers; growth factors such as, by way of example, and not limitation, bone growth factors or bone morphogenic proteins; wound healing agents; analgesics and analgesic combinations; local anesthetic agents; antihistamines; sedatives; angiogenesis-promoting agents; angiogenesis-inhibiting agents; tranquilizers and the like, which can be therapeutic as well as bioactive agents that are toxins. Cellular elements, which can be used for therapeutic use, include, but are not limited to mammalian cells including stem cells; cellular components or fragments, enzymes, DNA, RNA, and genes may also be included as bioactive components or drugs. Extensive list of bioactive compounds or drugs that may be used can be found in U.S. Pat. No. 8,067,031 cited herein for reference only.

"Biodegradable" is meant to denote a material that will degrade in a biological environment by either a biologically assisted mechanism, such as an enzyme catalyzed reaction or by a chemical mechanism which can occur in a biological medium, such as hydrolysis or by a dissolution mechanism in which the substance dissolves and is removed safely without any degradation.

"Biostable" is meant to denote a high chemical stability of a compound in an aqueous environment, which is similar to the environment found in the human body such as phosphate buffered saline (pH 7.2).

The term "biodegradable polymers" may be may include polymers or macromolecules which degrade/dissolve safely in the biological environment such as human body. The term applies to polymers that are hydrophobic or hydrophilic. The term is applicable to polymers that are crosslinked or non-crosslinked. The crosslinking may be done via condensation polymerization or via free radical polymerization or via ionic bonding. The biodegradable polymers may be random or block or graft copolymers. The biodegradable polymers may be linear, graft, dendramer or branched. The hydrophobic biodegradable polymers include, but are not limited to, polymers, dendramers, copolymers or oligomers of glycolide, dl-lactide, d-lactide, l-lactide, caprolactone, dioxanone and trimethylene carbonate; degradable polyurethanes; polyamides; polyesters; polypeptides; polyhydroxyacids; polyorthocarbonates, polylactic acid; polyglycolic acid; polyanhydrides; and polylactones. Biodegradable polymers also include polyhydroxyalkanoates, which are polyesters produced by microorganisms including and not limited to poly (3-hydroxybutyrate), 3-hydroxyvalerate, 4-hydroxybutyrate, 3-hydroxyhexanoate, 3-hydroxyoctanoate. The term applies to hydrophilic polymers, which include, but are not limited to, polyethylene glycol-polyhydroxy acid or polyethylene glycol-polylactone copolymers (PEG-PL copolymers); polyvinyl alcohol-co-polylactone copolymers; and derivatives of cellulose; collagen or modified collagen derivatives; gelatin; albumin or crosslinked albumin; fibrinogen; keratin; starch; hyaluronic acid and dextran.

The term "completely biodegradable" means more than 99 percent and preferably 99.9 and even more preferably 100 percent of the material is degraded and removed safely from the implantation site.

The term "partially biodegradable" means more than 50 percent, preferably more than 70 percent of the implanted material is degraded or removed safely from the implantation site. The term "biostable polymers" include but not limited to aliphatic and aromatic polyurethanes; polycarbonate polyurethane; polyether polyurethane; silicone polyurethane block copolymers; silicone rubbers; polydimethylsiloxane copolymers; polytetrafluoroethylene and other fluorinated polymers; expanded polytetrafluoroethylene; polyethylene; polypropylene; polyamide; polyamide block copolymers, polymethacrylates, polyacrylates, polymethyl methacrylate, polybutyl methacrylates, polyethylene vinylacetate, polyethylene vinylalcohol, polyethylene, polypropylene, and the like. The polymers must be biocompatible and suitable for implantation in the human or animal body.

"Sustained release" or "long term release" or "deliveries" are phrases used interchangeably herein, to mean longer than the expected delivery of a bioactive compound from the inventive composition. Typically, delivery will be at least one hour or more, and may extend to one day, to few days, to weeks, months to few years. The long term release can be achieved by any of a number of known or yet to be discovered or unknown mechanisms.

A "hydrogel" as used herein, refers to a semisolid composition constituting a substantial amount of water, and in which polymers or mixtures thereof are dissolved or dispersed. The polymers may be physically or chemically crosslinked or not crosslinked.

The term "fluid" generally refers to any flowable substance such as gas, air, liquids, water, solutions, emulsions, and suspensions, or anything else that flows.

Polyethylene glycol (PEG) or polyethylene oxide (PEO) refers to the same polymer, which is made by polymerization of ethylene oxide. Polypropylene glycol (PPG) or polypropylene oxide (PPO) refers to the same polymer, which is made by polymerization of propylene oxide. Polymeric nomenclature used in this patent application such as poly (ethylene glycol) or polyethylene glycol or polyethyleneglycol refer to the same polymer, unless otherwise stated clearly. This is also true for all others polymers referred in this patent application.

The term "micron" is means a length of $\frac{1}{1000000}$ of a meter.

As used herein, the term "activated" means increasing the chemical reactivity of a given functional group so that it can react with the target molecule under mild reaction conditions. For example, acid functionality in acrylic acid is not reactive enough to react with amine groups of proteins in water at pH 7.2 at room temperature. The reactivity of acid group in acrylic acid can be increased sufficiently by making an n-hydroxysuccinimide derivative so that it can react with proteins or tissue in water around pH 7.2 at room temperature (also known in the art as activation of acid group by n-hydroxysuccinimide group). Many activation chemistries are known in the peptide synthesis or protein modification art. Preferred activating moieties include succinimidyl moieties, n-hydroxymaleimide moieties, n-hydroxydisuccinimidyl moieties, sulfosuccinimidyl moieties and the like.

The term "macromonomer" or "macromer" refers to oligomeric or polymeric materials capable of undergoing fee radical polymerization.

The term "hydrophobic" is defined as materials or polymers or macromolecules having a low degree of water absorption or attraction.

The terms "coloring compositions" include any coloring composition or chemical that is suitable for human or animal implantation and are preferably approved by FDA for use in implantable medical devices. The compounds include but not limited to: Methylene blue; Eosin Y; Fluorescein sodium; Chromium-cobalt-aluminum oxide; Ferric ammonium citrate; Pyrogallol; Logwood extract; 1,4-Bis[(2-hydroxyethyl)amino]-9,10-anthracenedione bis(2-propenoic)ester copolymers(3;1,4-Bis[(2-methylphenyl)amino]-9,10-anthracenedione; 1,4-Bis[4-(2-methacryloxyethyl)phenylamino]anthraquinone copolymers; Carbazole violet; Chlorophyllin-copper complex, oil soluble; Chromium-cobalt-aluminum oxide; Chromium oxide greens; C.I. Vat Orange 1;

2-[[2,5-Diethoxy-4-[(4-methylphenyl)thiol]phenyl]azo]-1,3,5-benzenetriol; 16,23-Dihydrodinaphtho[2,3-a:2',3'-i]naphth[2',':6,7]indolo[2,3-c]carbazole-5,10,15,17,22,24-hexone; N,N'-(9,10-Dihydro-9,10-dioxo-1,5-anthracenediyl)bis benzamide; 7,16-Dichloro-6,15-dihydro-5,9,14,18-anthrazinetetrone; 16,17-Dimethoxydinaphtho(1,2,3-cd:3',2',1'-lm)perylene-5,10-dione; Poly(hydroxyethyl methacrylate)-dye copolymers: one or more of Reactive Black 5; Reactive Blue 21; Reactive Orange 78; Reactive Yellow 15; Reactive Blue No. 19; Reactive Blue No. 4; C.I. Reactive Red 11; C.I. Reactive Yellow 86; C.I. Reactive Blue 163; C.I. Reactive Red 180; 4-[(2,4-dimethylphenyl)azo]-2,4-dihydro-5-methyl-2-phenyl-3H-pyrazol-3-one; 6-Ethoxy-2-(6-ethoxy-3-oxobenzo[b]thien-2(3H)-ylidene)benzo[b]thiophen-3(2H)-one; Phthalocyanine green; Iron oxides; Titanium dioxide; Vinyl alcohol/methyl methacrylate-dye reaction products; one or more of: (1) C.I. Reactive Red 180; C.I. Reactive Black 5; C.I. Reactive Orange 78; C.I. Reactive Yellow 15; C.I. Reactive Blue No. 19; C.I. Reactive Blue 21; Mica-based pearlescent pigments; Disodium 1-amino-4-[[4-[(2-bromo-1-oxoallyl)amino]-2-sulphonatophenyl]amino]-9,10-dihydro-9,10-dioxoanthracene-2-sulphonate (Reactive Blue 69); D&C Blue No. 9; D&C Green No. 5; [Phthalocyaninato(2-)]copper; FD&C Blue No. 2; D&C Blue No. 6; D&C Green No. 6; D&C Red No. 17; D&C Violet No. 2; D&C Yellow No. 10; and the like. Among the compounds listed above, coloring compositions that are biodegradable are most preferred.

The term "minimally invasive surgery" or (MIS) is used herein includes, but is not limited to, surgical techniques such as, by way of example, and not limitation, laparoscopy, thoracoscopy, arthroscopy, intraluminal endoscopy, endovascular techniques, catheter-based cardiac techniques (such as, by way of example, and not limitation, balloon angioplasty), and interventional radiology.

The term "non-denatured" applies to collagen proteins in the tissue, which are completely or substantially preserved in a triple helix molecular arrangement.

The term "hydrophilic" is defined as materials or polymers or macromolecules having a strong affinity for water.

Polylactic acid or poly(lactic acid) or poly(lactide) or PLA is term used for a polymer which is made from lactide or lactic acid. Similarly, PGA is term used for polyglycolic acid or polyglycolate. Some synthetic biodegradable polyesters polymers are generally referred to as polylactones or polyhydroxyacids.

The term "exposing" refers to soaking the tissue in a fluid comprising the treatment agent for a period of time sufficient to treat the tissue. The soaking may be performed by, but is not limited to, incubation, swirling, immersion, mixing, or vortexing.

The term "oscillating" refers to and from motion of a needle along its transversal axis and preferably perpendicular to the tissue. Oscillating has been used synonymously with injecting.

The term "polymerizable" denotes the molecules that have the capacity to form additional covalent bonds resulting in monomer and/or monomers interlinking to oligomer or polymer formation, for example, molecules contain carbon-carbon double bonds of acrylate-type molecules. Such polymerization is characteristically initiated by free-radical formation, for example, resulting from photon absorption of certain dyes and chemical compounds to ultimately produce free radicals. The term polymerizable is also applicable to compounds, which can undergo condensation polymerization and form a linear or crosslinked polymer.

The term "water soluble" generally refers to solubility of a compound in water wherein the compound has a solubility of greater than 5 g/100 g, preferably greater than 1 g/100 g in water or buffered water solutions.

The term "water insoluble" generally refers to solubility of a compound in water wherein the compound has a solubility of less than 5 g/100 g, preferably less than 1 g/100 g in water or buffered water solutions.

The term "imaging agent(s)" or "visualization agent(s)" include any medical imaging agent that helps to visualize the human body/tissue using naked human eye or using machine assisted viewing. The term generally applies to but not limited to: coloring compositions that induce coloring compounds added to medical devices and drug delivery compositions, radio-opaque contrast agents that helps to visualize organs/tissues using x-ray imaging techniques, NMR contrast agents that assist in MRI imaging techniques and the like.

The phrase "effective crosslinking" is used wherein the treated tissue shows improved resistance to enzymatic degradation or increase in shrink temperature. Generally "effective cross-linking" refers to, but is not limited to, exemplary conditions such as treating a biological tissue like bovine pericardium tissue (size 2 cm by 2 cm) with 20 ml 0.4% glutaraldehyde solution in distilled water or in 20 mM phosphate buffered saline (pH 7.2) for 24 to 48 hours at room temperature (around 25 degree C.). Under effective crosslinking conditions covalent bonds are formed between tissue components such as collagen, elastin and other proteins or between the tissue and external compounds or crosslinkers. Tissue is considered "effectively crosslinked" if it is substantially preserved (without degradation) when incubated in 4 percent pepsin solution in 0.1M hydrochloric acid at 37 degree C. for 24 hours or if the shrink temperature of the tissue is increased by five degrees or more relative to the same uncrosslinked tissue (control tissue).

The "Rifampicin" or "Rifampin" refers to the same drug molecule.

Tissue crosslinking for bioprosthesis use is reported in a number of patents and scientific journals. In bioprosthesis applications, tissue is first removed from the dead animal, processed and then used in medical device application such as heart valve. Some the examples of such prior art include, cited herein for reference only, U.S. 61/77514, U.S. 61/32986, and US Patent Application 2009/0130162 and cross-references cited therein.

Animal tissue based medical devices have a long history clinical use. Examples of bioprostheses include tissue based heart valves, surgical patch, hernia patch, wound coverings, vascular grafts and the like. Tissue based biomaterials are very successful in heart valve application due to their superior blood compatibility and durability. When animal tissue is implanted inside the human or animal body, it is degraded via enzymatic pathway within 4 to 6 weeks. To protect against degradation and to make the tissue useful for longer period of time, tissue must be stabilized against the degradation process. Most commonly, tissues are chemically treated or crosslinked to make them biostable and non-immunogenic. In heart valve application and many other bioprostheses applications, the tissue is generally modified or crosslinked with glutaraldehyde.

The present invention is now described with reference to the drawings.

FIG. 1A shows a partial schematic representation of a method for infusing drug bearing microencapsulated particles in the bioprosthetic tissue. The drug particles 102 are fed through a reservoir of a sandblasting machine where the drug particles are given sufficient kinetic energy using a gas pressure stream 104 or other means and the particles are bombarded on the tissue surface. The kinetic energy is controlled in such way that particles possessing kinetic energy, designated as 108, are embedded in the tissue surface or bioprosthesis surface 110. The embedded drug particles are represented as 106.

Figure 1B:
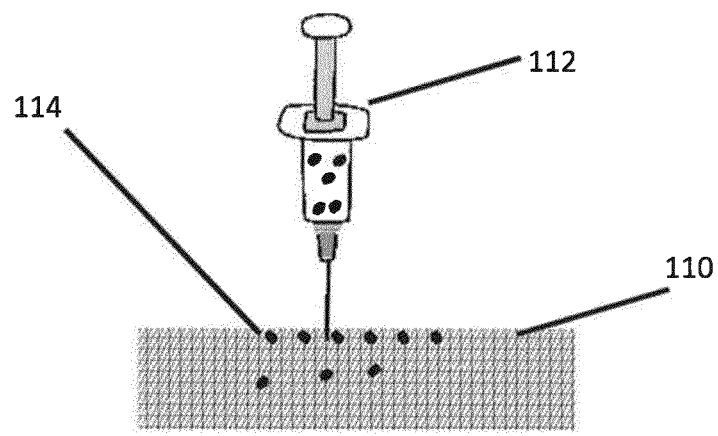
FIG. 1B is a representative diagram illustrating a method for infusing the microencapsulated drug bearing particles via an oscillating syringe needle in an alternate embodiment of the invention.

In an alternatively embodiment, as shown in FIG. 1B, drug particles may be injected in the tissue surface 110 via oscillating syringe needle or tattoo machine needle or other suitable particle injectable device designated as 112. The embedded drug particles are represented as 114.

Figure 2A:
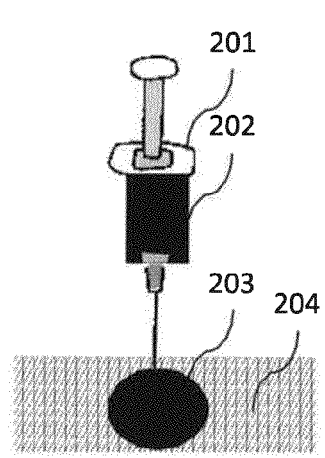
FIGS. 2A, 2B and 2C are representative diagrams illustrating method for infusion of liquid compositions in the skin tissue in an embodiment of the invention.
Figure 2B:
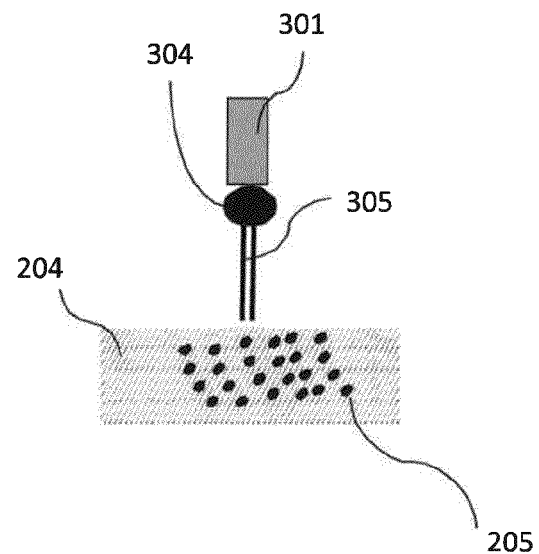
Figure 2C:
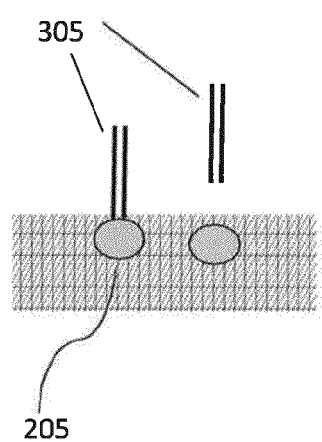

FIGS. 2A through 2C, show a partial schematic representation of a conventional method of infusion of liquids in the tissue such as skin tissue and a method of delivery described in this invention. In the conventional method shown schematically in FIG. 2A, a syringe 201 is used to dispense an injectable liquid designated as 202 in a tissue layer such as dermis layer 204. The syringe dumps the required amount of liquid 202 generally at one injection site forming a pool of liquid 203 at the injection site. Generally, all the liquid is dispensed at once forming a blob of liquid.

As shown in FIGS. 2B and 2C, an oscillating needle 305 activated by an oscillating device 301, is used to dispense the liquid from a temporary reservoir 304 in the tissue layer 204. As the needle 305 oscillates i.e. pulsates or reciprocates (needle goes in and out of the dermis layer or skin tissue), it dispenses several tiny liquid droplets 205 inside the dermis layer 204.

FIG. 2C shows a magnified view of the dispensing process. The liquid is pushed out from the oscillating needle 305. When the oscillating needle comes out the tissue surface, the liquid droplets 205 are separated from the needle and stays inside the tissue. This oscillation process is generally repeated 10 to 12000 times per minute, dispensing several droplets with droplet volume 1.0E-02 to 1.0E-16 ml. The oscillating needle is generally moved in large area of the skin or tissue to distribute the number of droplets in a larger area.

Figure 3A:
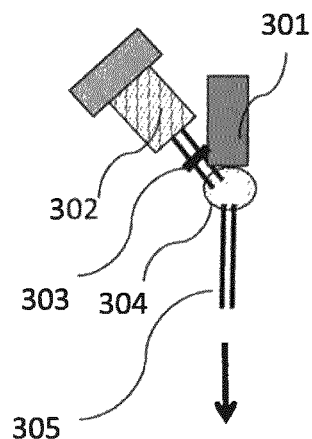
FIG. 3A shows a partial schematic representation of a device that is used for delivering a composition in an embodiment of the invention.
Figure 3B:
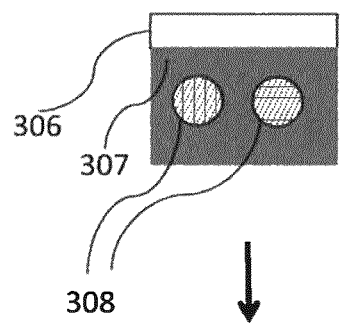
FIG. 3B illustrates a schematic view of the epidermis layer and dermis layers along with the injected composition.
Figure 3C:
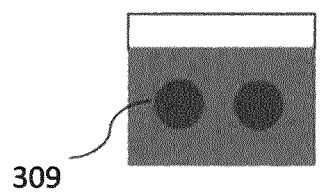
FIG. 3C shows partial schematic representation of the epidermis layer and dermis layers along with injected composition retained at the implanted site for local sustained drug delivery.

FIGS. 3A through 3C show partial schematic representations of a method for local delivery of injectable composition comprising; microparticles, preferably drug encapsulated microparticles and a biocompatible carrier fluid such as PBS buffer solution (pH 7.2), at a local site inside the human/animal body such as dermis layer of the skin tissue. The volume of injectable microparticulate composition deposited is less than 1.0E-02 ml. An injectable composition is loaded inside the injection device capable of injecting the composition at 10 to 12000 injections per minute. During each injection the device can deliver 1.0E-02 to 1.0E-16 ml of injectable composition. After injecting the composition, the fluid in the composition is dissipated by the surrounding tissue leaving behind the microparticles entrapped in the tissue, which deliver the encapsulated drug in a sustained manner.

FIG. 3A shows a partial schematic representation of the injection device wherein 301 represents an oscillation apparatus that is used to oscillate the injection needle 305. As an example, 301 could be magnetic coils and other parts of the tattoo machine. 302 represents an injectable composition reservoir which is connected to a temporary reservoir 304 via a control valve 303 which controls the flow of injectable composition to the needle 305. The oscillating needle delivers the composition from reservoir 304 in the skin tissue. An epidermis layer 306 and dermis layers 307 along with the injected composition droplets 308 are schematically shown in FIG. 3B. As shown in FIG. 3C, the fluid in the injected droplets is dissipated in the surrounding tissue leaving behind the microparticles 309 in the tissue, which release the drug at the injection site in a sustained manner. The carrier fluids in the injected composition have been dispersed in the tissue.

Figure 3D:
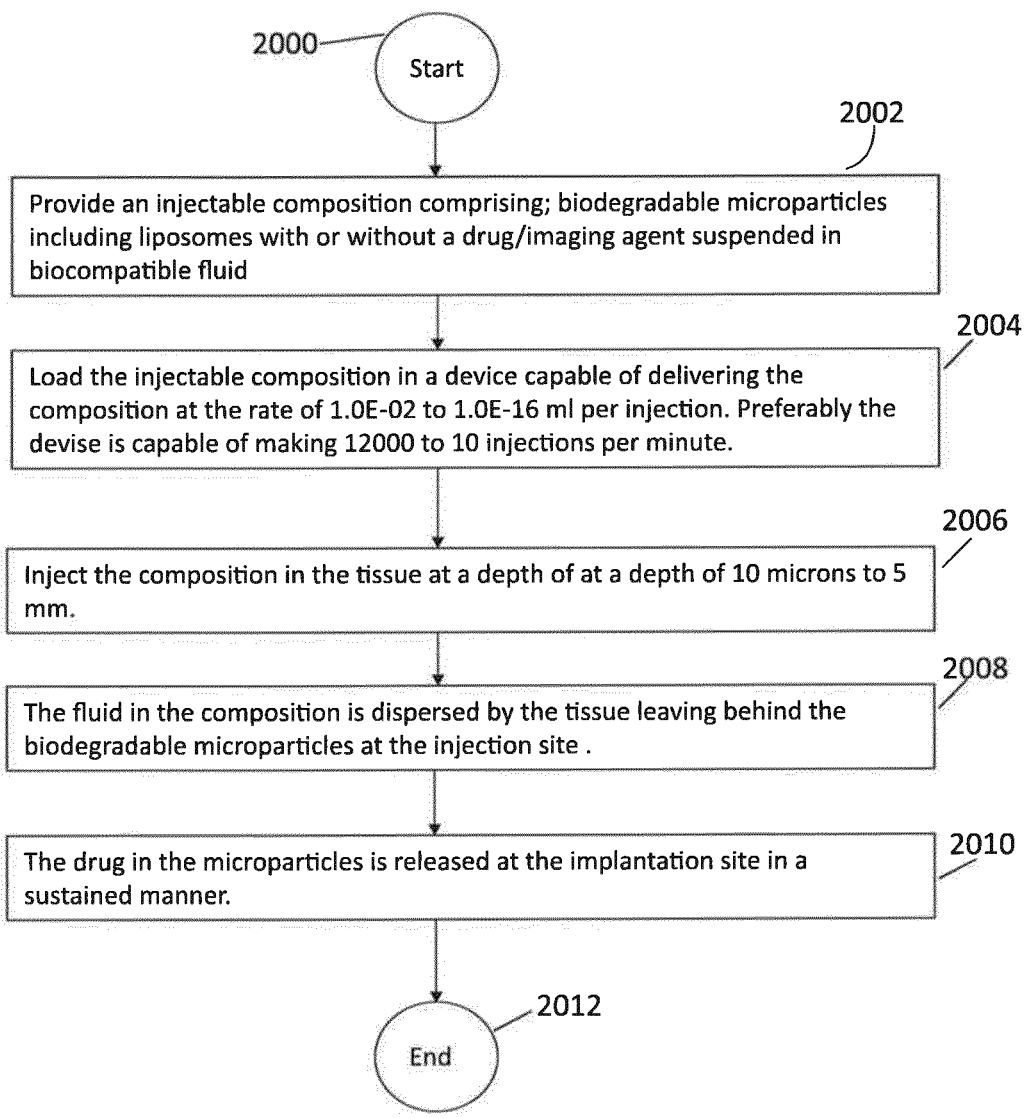
FIG. 3D denotes an illustrative flow chart depicting a method for injecting drug bearing microparticles in an alternate embodiment.

FIG. 3D denotes a flow chart depicting the sequence of steps followed in an embodiment wherein the injectable composition comprises of biodegradable microparticles including liposomes with or without a drug or imaging agent suspended in a biocompatible fluid.

In general, "microencapsulated particles" referred in this invention comprises polymer encapsulated microparticles, liposomes and related compositions, micellar system encapsulated compositions, cyclodextran encapsulated compositions and the like.

This invention is not limited to polymeric microspheres based drug delivery systems. R. P. Patel et al (Intl. R. J. of Pharmaceuticals (2011), Vol. 01, Issue 02, pp. 65-71) disclose anti-acne Tretinoin drug based liposome composition for sustained drug delivery; cited herein for reference only. Liposome based sustained drug delivery disclosed by Patel et al and other such sustained drug delivery systems known in the art can also be delivered using methods and compositions disclosed in this invention. Similar to liposomes, micellar drug delivery systems wherein the drug is encapsulated in a micelle formed in the water solution can also be used and deposited using compositions and methods described in this invention. Example 11c Part 2 illustrates one such example. Other known micellar drug delivery systems known in the art can also be used using methods described in this invention. Drugs encapsulated in cyclodextran or cyclodextran derivatives are also considered as microencapsulated particle systems.

Referring to FIG. 3D, at step 2002, an injectable composition as per predetermined concentration and formulation is provided. At step 2004, said composition is loaded in the device capable of delivering the composition at the rate of 1.0E-02 to 1.0E-16 ml per injection. Preferably the devise is capable of making 12000 to 10 injections per minute. At step 2006, the composition is injected in the tissue at a depth of at a depth of 10 microns to 5 mm. At step 2008, the fluid in the composition is dispersed by the tissue leaving behind the biodegradable microparticles at the injection site. At step 2010, the drug in the microparticles is released at the implantation site in a sustained manner.

Figure 4A:
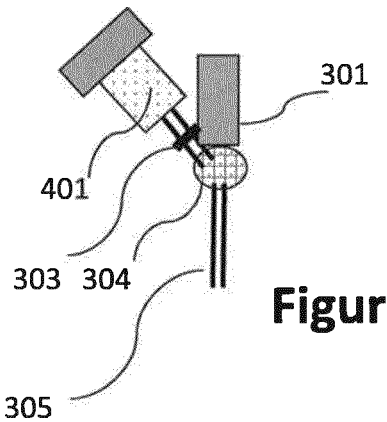
FIG. 4A shows a partial schematic representation of an injection device apparatus in an embodiment of the invention.
Figure 4B:
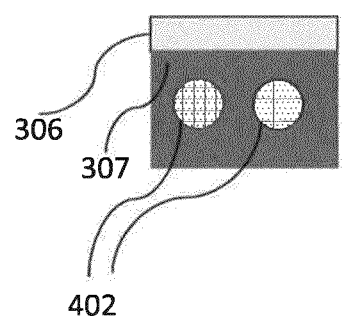
FIG. 4B is a schematic representation of the epidermis layer and dermis layers along with injected composition droplets.
Figure 4C:
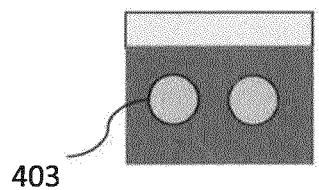
FIG. 4C shows a partial schematic representation of the epidermis layer and dermis layers along with injected composition retained at the implanted site for local sustained drug delivery. The solvent in the injected composition is dispersed in the tissue leaving behind the polymer particle.

FIGS. 4A through 4C show a partial schematic representation of a method for local delivery of injectable composition comprising; biostable polymer or biodegradable polymer solution and a combination of drug and an imaging agent, at a local site inside the human or animal body such as dermis layer of the skin tissue and volume of polymer solution deposited is less than 1.0E-02 ml. The injectable composition is loaded inside the injection device capable of injecting the composition at the rate of 10 to 12000 injections per minutes. During each injection, the device can deliver 1.0E-02 to 1.0E-16 ml of injectable composition. After injecting the composition, the solvent in the polymer is dissipated by the surrounding tissue leaving behind the polymer microparticle and the drug. The drug is released by the polymer in a sustained manner.

FIG. 4A shows a partial schematic representation of an injection device apparatus wherein 301 represents an oscillation apparatus that is used to oscillate the injection needle 305. 301 could be magnetic coils or electric motor shaft and other parts of the tattoo machine. 401 represents an injectable composition reservoir, which is connected to the temporary reservoir 304 via a flow control valve 303. The valve controls the flow of injectable composition to the needle 305 and which may the controlled by the user during its use. The oscillating needle delivers the composition from 304 via the needle 305 in the skin tissue. An epidermis layer 306 and dermis layers 307 along with injected composition droplets 402 are schematically shown in FIG. 4B. The solvent in the injected droplets is dissipated or dissolved in the surrounding tissue leaving behind or precipitating the polymer with entrapped drug or imaging agents 403 as depicted in FIG. 4C. The polymer particles 403 release the drug at the injection site in a sustained manner. The particle is removed by biodegradation process in few hours to several months depending on the polymer used.

Figure 4D:
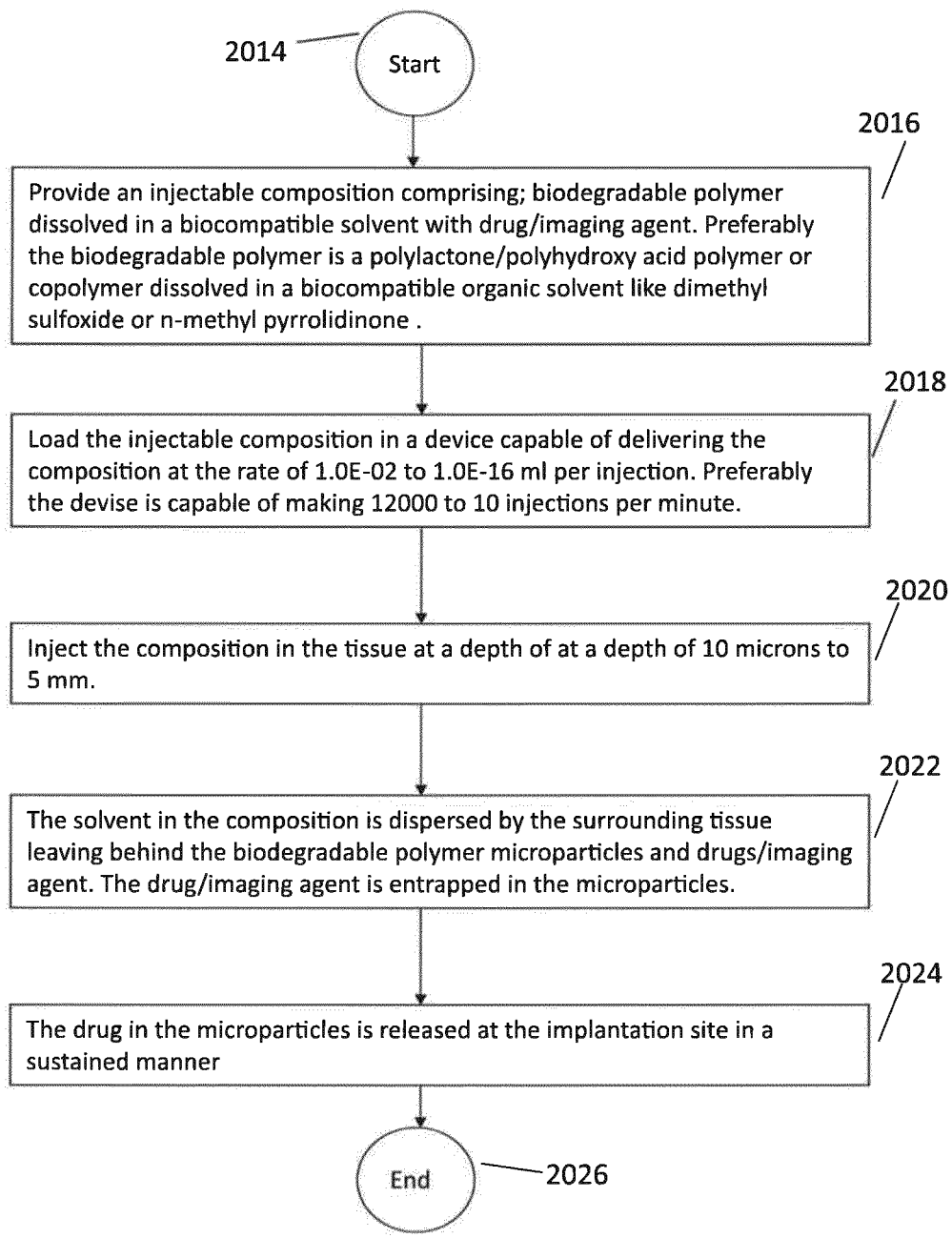
FIG. 4D denotes an illustrative flow chart depicting a method for injecting drug bearing microparticles in an alternate embodiment.

FIG. 4D denotes a flow chart depicting the sequence of steps followed in an embodiment wherein the injectable composition comprises of polymer preferably biodegradable polymer dissolved in a biocompatible solvent with a combination of drug and/or imaging agent. Preferably the biodegradable polymer is a polylactone or polyhydroxy acid polymer or copolymer dissolved in a biocompatible organic solvent like dimethyl sulfoxide or n-methyl pyrrolidinone.

At step 2016, an injectable composition as per predetermined concentration and formulation is provided. At step 2018, said composition is loaded in the device capable of delivering the composition at the rate of 1.0E-02 to 1.0E-16 ml per injection. Preferably the devise is capable of making 12000 to 10 injections per minute. At step 2020, the composition is injected in the tissue at a depth of at a depth of 10 microns to 5 mm. At step 2022, the fluid in the composition is dispersed by the tissue leaving behind the biodegradable microparticles and drugs and the imaging agent. The drug and the imaging agent are entrapped in the microparticles. At step 2024, the drug in the microparticles is released at the implantation site in a sustained manner.

Figures 5A, 5B:
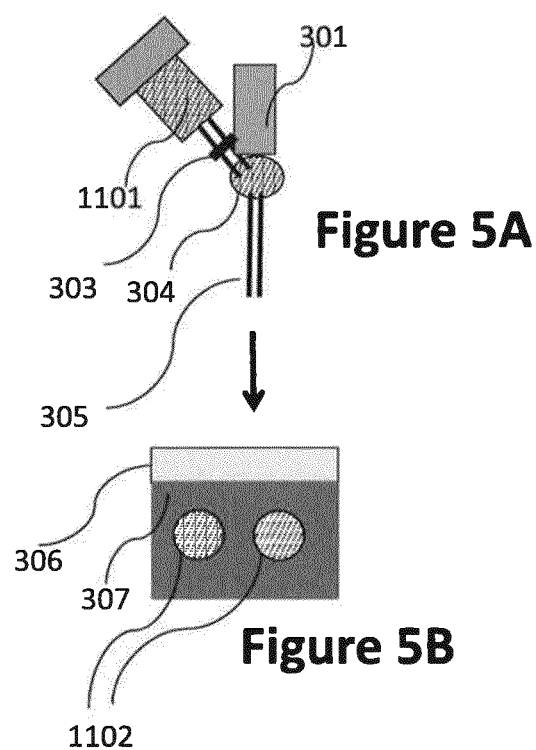
FIG. 5A shows a partial schematic representation of an injection device apparatus in an embodiment of the invention.
FIG. 5B is a schematic representation of the epidermis layer and dermis layers along with injected composition droplets.

FIGS. 5A through 5B show a partial schematic representation of a method for local delivery of injectable composition comprising; polymeric or non-polymeric liquid carrier and a combination of drug and an imaging agent, at a local site inside the human or animal body such as dermis layer of the skin tissue and the volume of liquid composition deposited is less than 1.0E-02 ml. The injectable composition is loaded inside the injection device capable of injecting the composition at 10 to 12000 injections per minute. During each injection the device can deliver 1.0E-02 to 1.0E-16 ml of injectable composition. After injecting the composition, the liquid droplets deliver the drug in a sustained manner.

FIG. 5A shows a partial schematic representation of the injection device apparatus wherein 301 represents an oscillation apparatus that is used to oscillate the injection needle 305. 301 could be magnetic coils and other parts of the tattoo machine. 1101 represent an injectable composition comprising; polymeric or non-polymeric liquid carrier and a combination of drug and/or imaging agent, which is connected to the temporary reservoir 304 via a flow control valve 303. The valve controls the flow of injectable composition to the needle 305. The oscillating needle 305 delivers the composition from 304 into the skin tissue. An epidermis layer 306 and dermis layers 307 along with injected composition droplets 1102 are schematically shown in FIG. 5B. The polymeric or non-polymeric liquid droplets release the drug at the injection site in a sustained manner.

Figure 5C:
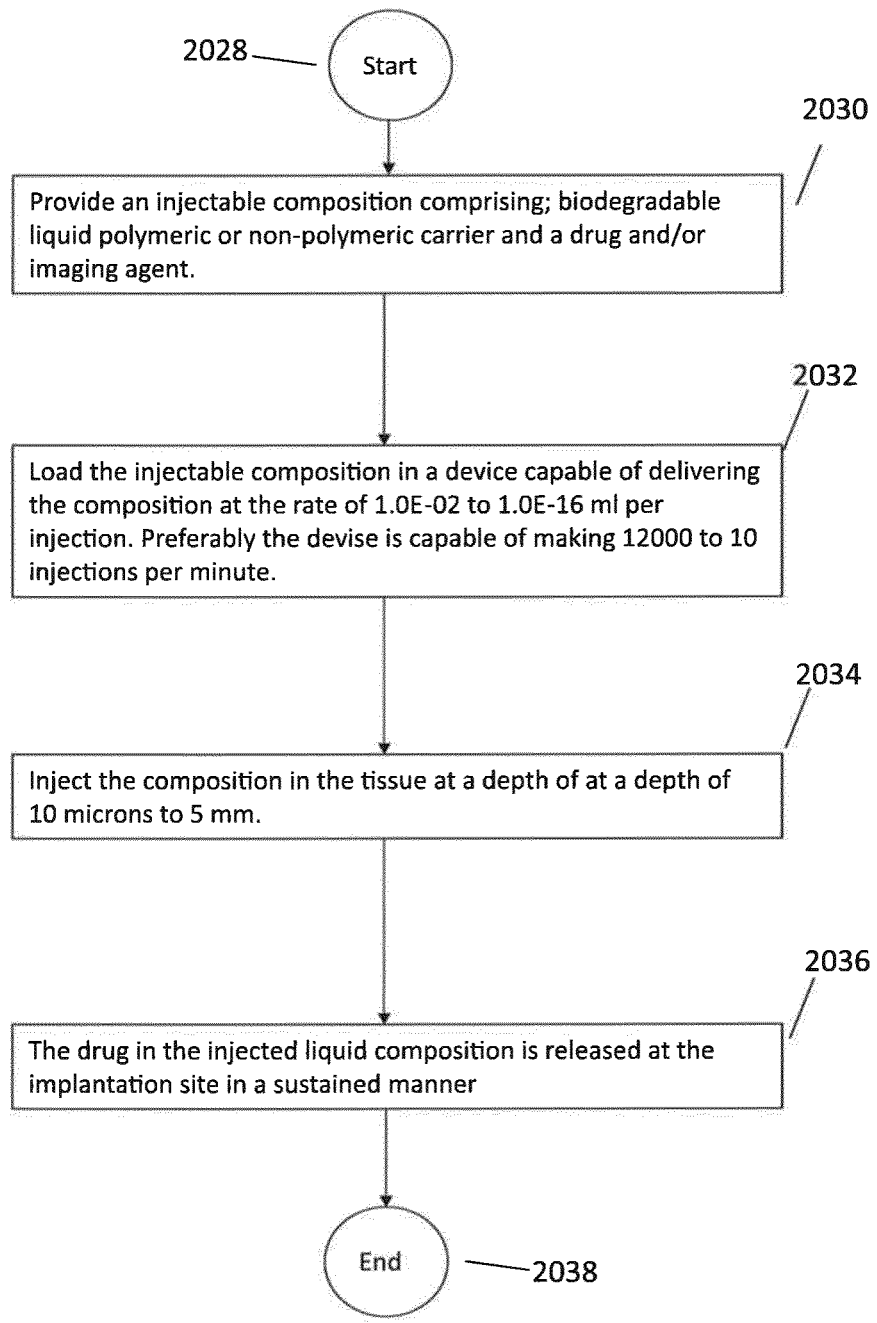
FIG. 5C denotes an illustrative flow chart depicting a method for injecting drug bearing microparticles in an alternate embodiment.

FIG. 5C denotes a flow chart depicting the sequence of steps followed in an embodiment wherein the injectable composition comprises of biodegradable liquid polymeric or non-polymeric carrier with a combination of drug and imaging agent. Preferably the biodegradable polymer is a polylactone or polyhydroxy acid polymer or copolymer dissolved in a biocompatible organic solvent like dimethyl sulfoxide or n-methylpyrrolidinone or ethanol.

At step 2030, an injectable composition as per predetermined concentration and formulation is provided. At step 2032, said composition is loaded in the device capable of delivering the composition at the rate of 1.0E-02 to 1.0E-16 ml per injection. Preferably the devise is capable of making 12000 to 10 injections per minute. At step 2034, the composition is injected in the tissue at a depth of at a depth of 10 microns to 5 mm. At step 2036, the drug in the injected liquid composition is released at the implantation site in a sustained manner.

Figure 6A:
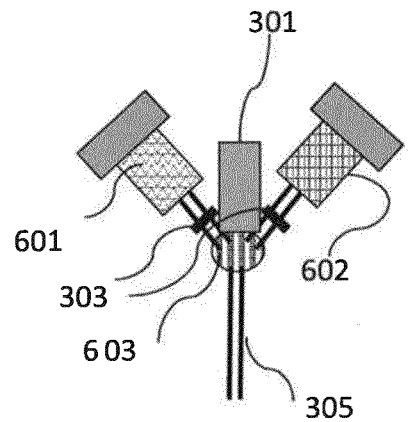
FIG. 6A shows a partial schematic representation of an injection device apparatus in an embodiment of the invention wherein the injectable composition comprises precursors that form crosslinked compositions.
Figure 6B:
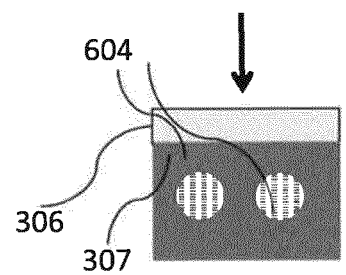
FIG. 6B is a schematic representation of the epidermis layer and dermis layers along with injected composition droplets.
Figure 6C:
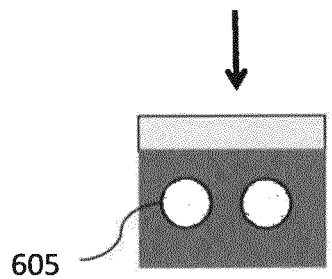
FIG. 6C shows a partial schematic representation of the epidermis layer and dermis layers along with injected composition retained at the implanted site for local sustained drug delivery. The injected composition has been crosslinked in situ via polymerization reaction.

FIGS. 6A through 6C show a partial schematic representation of a method for local delivery of injectable composition comprising; precursors that form crosslinked compositions in situ wherein the volume of crosslinked composition formed is less than 1.0E-02 ml. The crosslinked compositions may comprise of cells, drugs, or imaging agents. The injectable composition(s) are loaded inside the injection device capable of injecting the composition at 10 to 12000 injections per minute. During each injection the device can deliver 1.0E-02 to 1.0E-16 ml of injectable composition. After injecting the composition, the injected precursors undergo ionic or chemical or enzymatic reaction such as polymerization or crosslinking reaction forming a crosslinked material and entrapping the cells, drug or imaging agent. The entrapped drug is then released in a sustained manner. The crosslinked material could be hydrophobic or hydrophilic or hydrogel. The crosslinked material could be biostable or biodegradable.

FIG. 6A shows a partial schematic representation of the injection device apparatus wherein 301 schematically represents an oscillation apparatus that is used to oscillate the injection needle 305. 301 could be magnetic coils and other parts of the tattoo machine. 601 and 602 represent a duality of injectable composition reservoirs, which are connected to the temporary reservoir 603 via two flow control valves designated as 303. The components of 601 and 602 may be mixed in 603 prior to injecting. The valve 303 controls the flow of injectable composition to the needle. There could be more than two reservoirs in the device depending on the chemistry of the injectable composition. Two reservoirs shown in the figure are exemplary and should not construe to limit the scope of the invention. The oscillating device 301 delivers the premixed precursor composition from 603 in the skin tissue via oscillating needle 305. An epidermis layer 306 and dermis layers 307 along with injected composition droplets 604 are schematically shown in FIG. 6B. The injected droplets undergo crosslinking or polymerization reaction to form a crosslinked material with entrapped drug and imaging agents. The chemical reaction converts the liquid droplets into solid or hydrogels microparticles or microspheres designated as 605. The polymer particles release the drug at the injection site in a sustained manner.

Figure 6D:
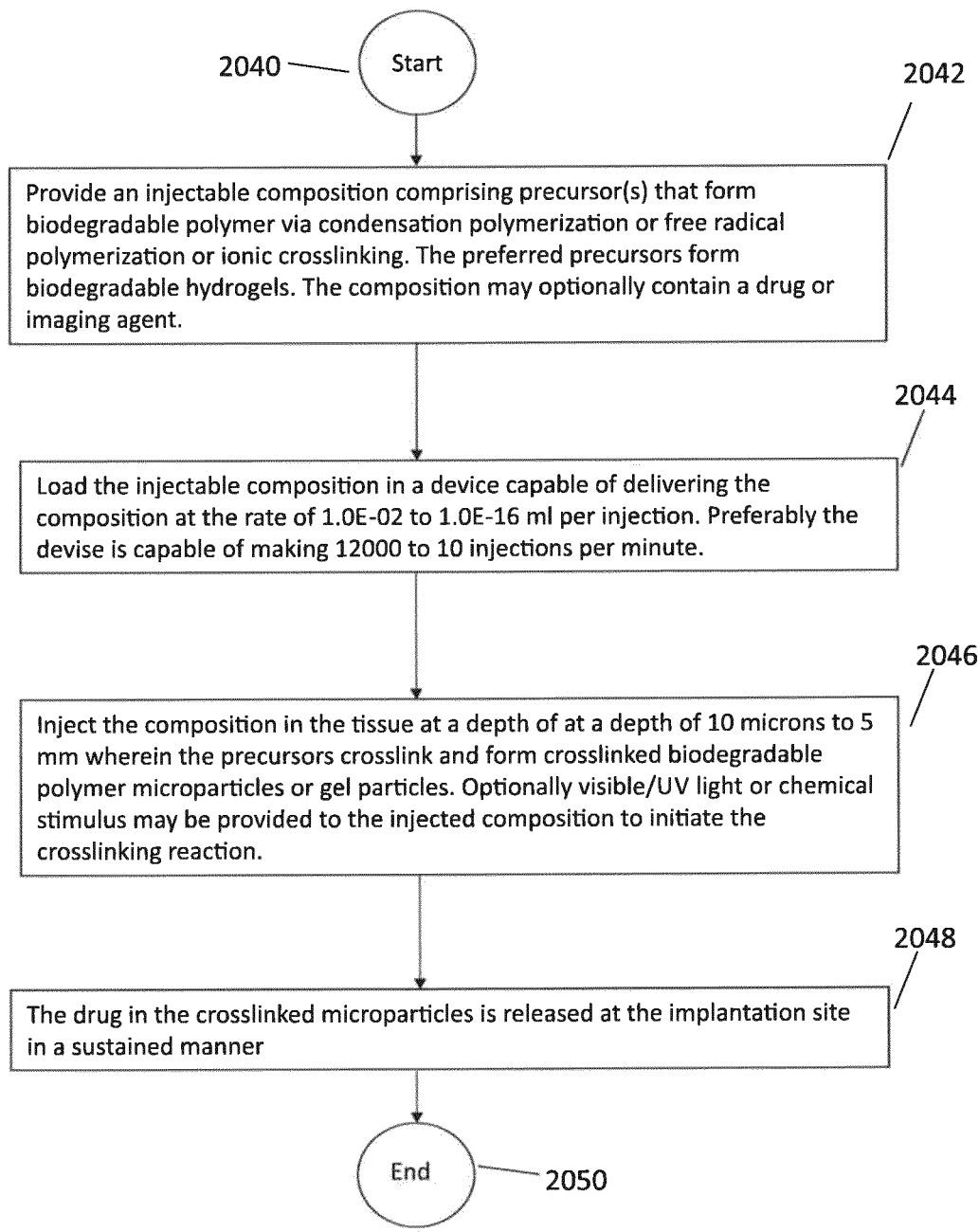
FIG. 6D denotes an illustrative flow chart depicting a method for injecting drug bearing microparticles in an alternate embodiment.

FIG. 6D denotes a flow chart depicting the sequence of steps followed in an embodiment wherein the injectable composition comprises of an injectable composition comprising precursor(s) that form biodegradable polymer via condensation polymerization or free radical polymerization or ionic crosslinking or enzymatic reaction. The preferred precursors form biodegradable hydrogels. The composition may optionally comprise of a combination of a drug or imaging agent.

At step 2042, an injectable composition as per predetermined concentration and formulation is provided. At step 2044, said composition is loaded in the device capable of delivering the composition at the rate of 1.0E-02 to 1.0E-16 ml per injection. Preferably the devise is capable of making 12000 to 10 injections per minute. At step 2046, the composition is injected in the tissue at a depth of at a depth of 10 microns to 5 mm wherein the precursors crosslink and form crosslinked biodegradable polymer microparticles or gel particles. Optionally visible/UV light or chemical stimulus may be provided to the injected composition to initiate the crosslinking reaction. At step 2048, the drug in the crosslinked microparticles is released at the implantation site in a sustained manner.

FIGS. 7A through 7D show a partial schematic representation of a method for local delivery of injectable composition comprising low melting non-polymer or polymer preferably low melting biodegradable polymer and a combination of drug and an imaging agent, at a local site inside the human or animal body such as dermis layer of the skin tissue. The injectable composition is loaded inside the injection device capable of injecting the composition at 10 to 12000 injections per minute. During each injection the device can deliver 1.0E-02 to 1.0E-16 ml of injectable composition. The polymer may be melted by heating the composition before loading it in the device or it could be melted inside the device. After injecting the composition in the tissue, the melted composition cools to body temperature, forming solid particles at the injection site.

Figure 7A:
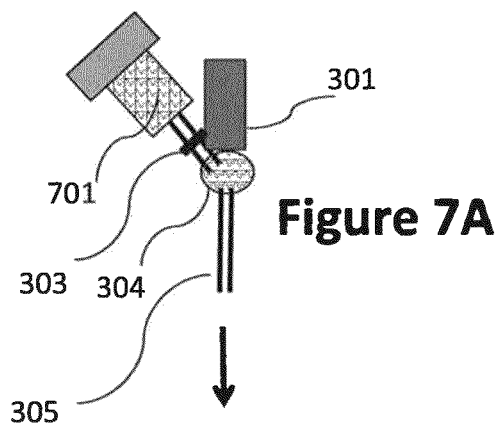
FIG. 7A shows a partial schematic representation of an injection device wherein the injectable composition comprising low melting non-polymer or polymer, low melting biodegradable polymer, drugs and imaging agents in an alternate embodiment of the invention.
Figure 7B:
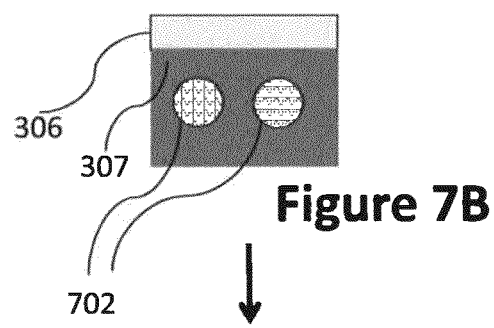
FIG. 7B is a schematic representation of the epidermis layer and dermis layers along with injected composition droplets.
Figure 7C:
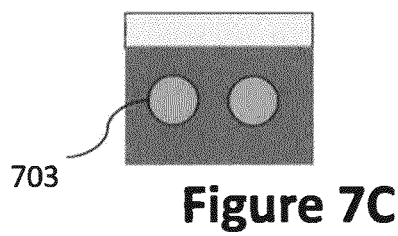
FIG. 7C shows a partial schematic representation of the epidermis layer and dermis layers along with injected composition retained at the implanted site for local sustained drug delivery. The injected composition is cooled and solidified to form microparticles in situ.

FIG. 7A shows a partial schematic representation of the injection device apparatus wherein 301 represents an oscillation apparatus that is used to oscillate the injection needle 305. 301 could be magnetic coils and other parts of the tattoo machine. 701 represents an injectable composition reservoir that could be melted by the electrical heating coil wrapped around the 701 reservoir. 701 is connected to the temporary reservoir 304 via a control valve 303, which controls the flow of melted injectable composition to the needle. The oscillating needle 305 delivers the melted composition from 304 in to skin tissue via 305. An epidermis layer 306 and dermis layers 307 along with injected melted composition droplets 702 as schematically shown in FIG. 7B. As shown in FIG. 7C, the cooled injected solid microparticles designated as 703, present in the tissue release the drug at the injection site in a sustained manner.

Figure 7D:
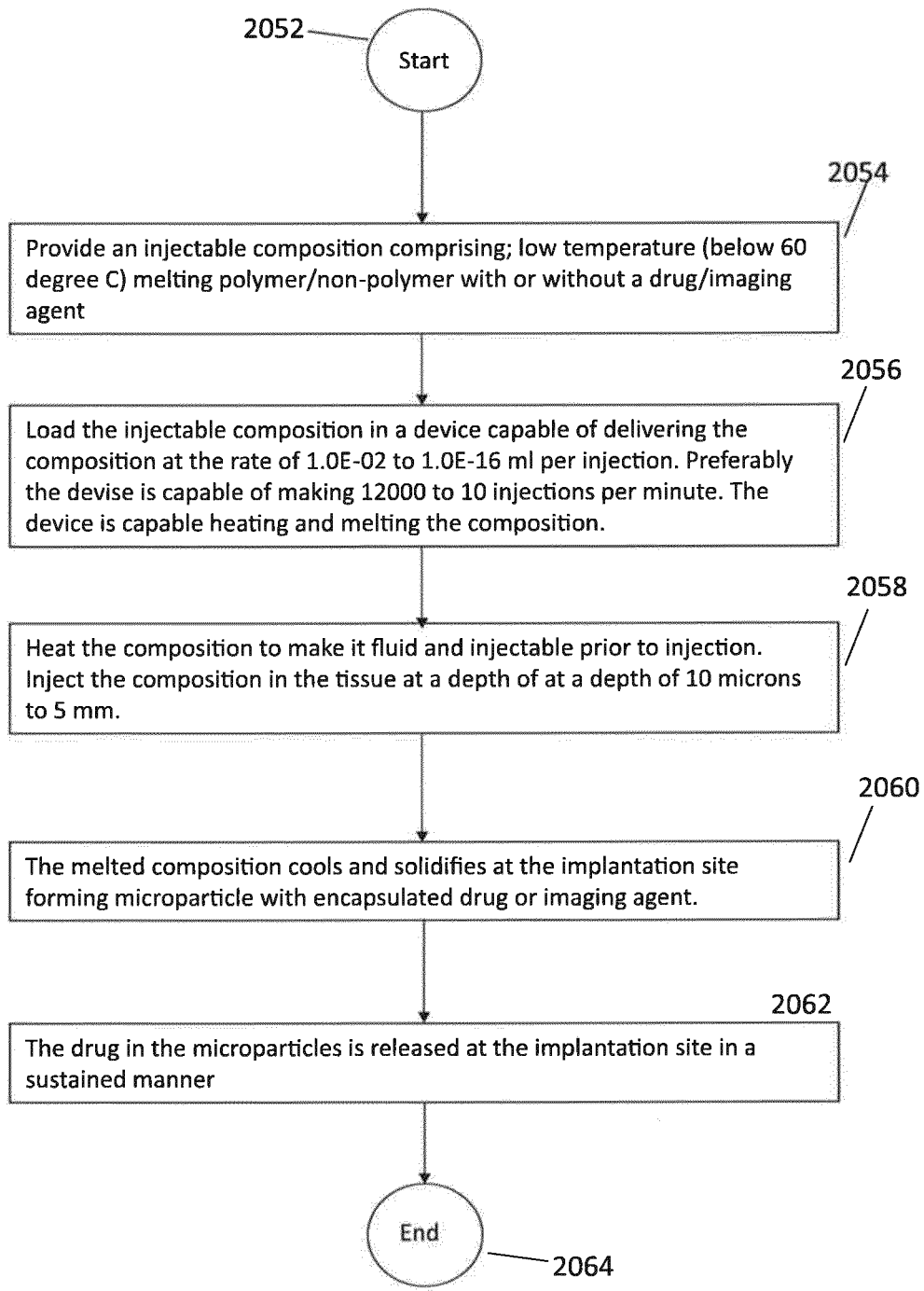
FIG. 7D denotes an illustrative flow chart depicting a method for injecting drug bearing microparticles in an alternate embodiment.

FIG. 7D denotes a flow chart depicting the sequence of steps followed in an embodiment wherein the injectable composition comprises of low temperature (below 60 degree C.) melting polymer or non-polymer with or without a combination of drug and an imaging agent.

At step 2054, an injectable composition as per predetermined concentration and formulation is provided. At step 2056, said composition is loaded in the device capable of delivering the composition at the rate of 1.0E-02 to 1.0E-16 ml per injection. Preferably the devise is capable of making 12000 to 10 injections per minute. At step 2058, the composition is heated to make it fluid and injectable prior to injection. The composition is injected in the tissue at a depth of 10 microns to 5 mm. At step 2060, the melted composition cools and solidifies at the implantation site forming microparticle with encapsulated drug or imaging agent. At step 2062, the drug in the microparticles is released at the implantation site in a sustained manner.

Figure 8A:
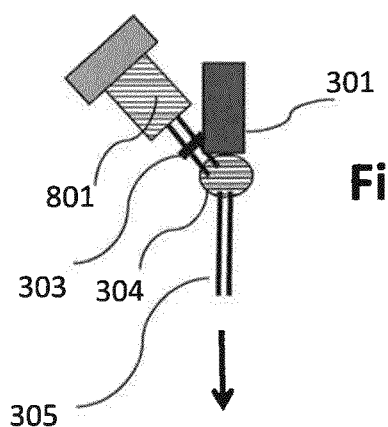
FIG. 8A shows a partial schematic representation of an injection device apparatus in an embodiment of the invention.
Figure 8B:
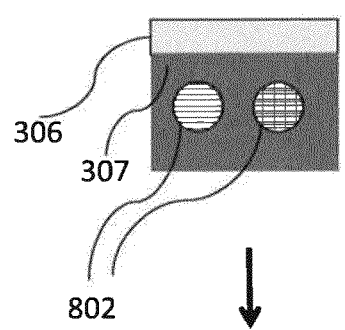
FIG. 8B is a schematic representation of the epidermis layer and dermis layers along with injected composition droplets.
Figure 8C:
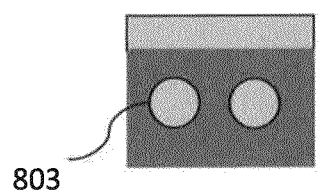
FIG. 8C shows a partial schematic representation of the epidermis layer and dermis layers along with injected composition retained at the implanted site for local sustained drug delivery. The injected composition is converted into gel particle via thermoreversible gel formation.

FIGS. 8A through 8C show a partial schematic representation of a method for local delivery of thermoreversible injectable fluid composition with or without drug and an imaging agent at a local site inside the human or animal body such as dermis layer of the skin tissue. The injectable composition is loaded inside the injection device capable of injecting the composition at 10 to 12000 injections per minute. During each injection the device can deliver 1.0E-02 to 1.0E-16 ml of injectable composition. The composition is either heated (below 60 degree C.) or cooled (0-20 degree C.) to make it in a fluid or injectable state prior to injection. After injecting the composition, the composition undergoes temperature induced gelation at the injection site.

FIG. 8A shows a partial schematic representation of the injection device apparatus wherein 301 schematically represents an oscillation apparatus that is used to oscillate the injection needle 305. 301 could be magnetic coils and other parts of the tattoo machine. 801 represents an injectable composition reservoir that could be cooled or heated to make the composition fluid and injectable. 801 is connected to the temporary reservoir 304 via a control valve 303 which controls the flow of the fluid composition to the needle. The oscillating needle delivers the fluid composition from the 304 in the skin tissue via 305. An epidermis layer 306 and dermis layers 307 along with injected composition droplets 802 are schematically shown in FIG. 8B. The body temperature induces the conversion of fluid 802 into a gel particle 803 entrapping the drug and imaging agent. 803 releases the drug in a sustained manner.

Figure 8D:
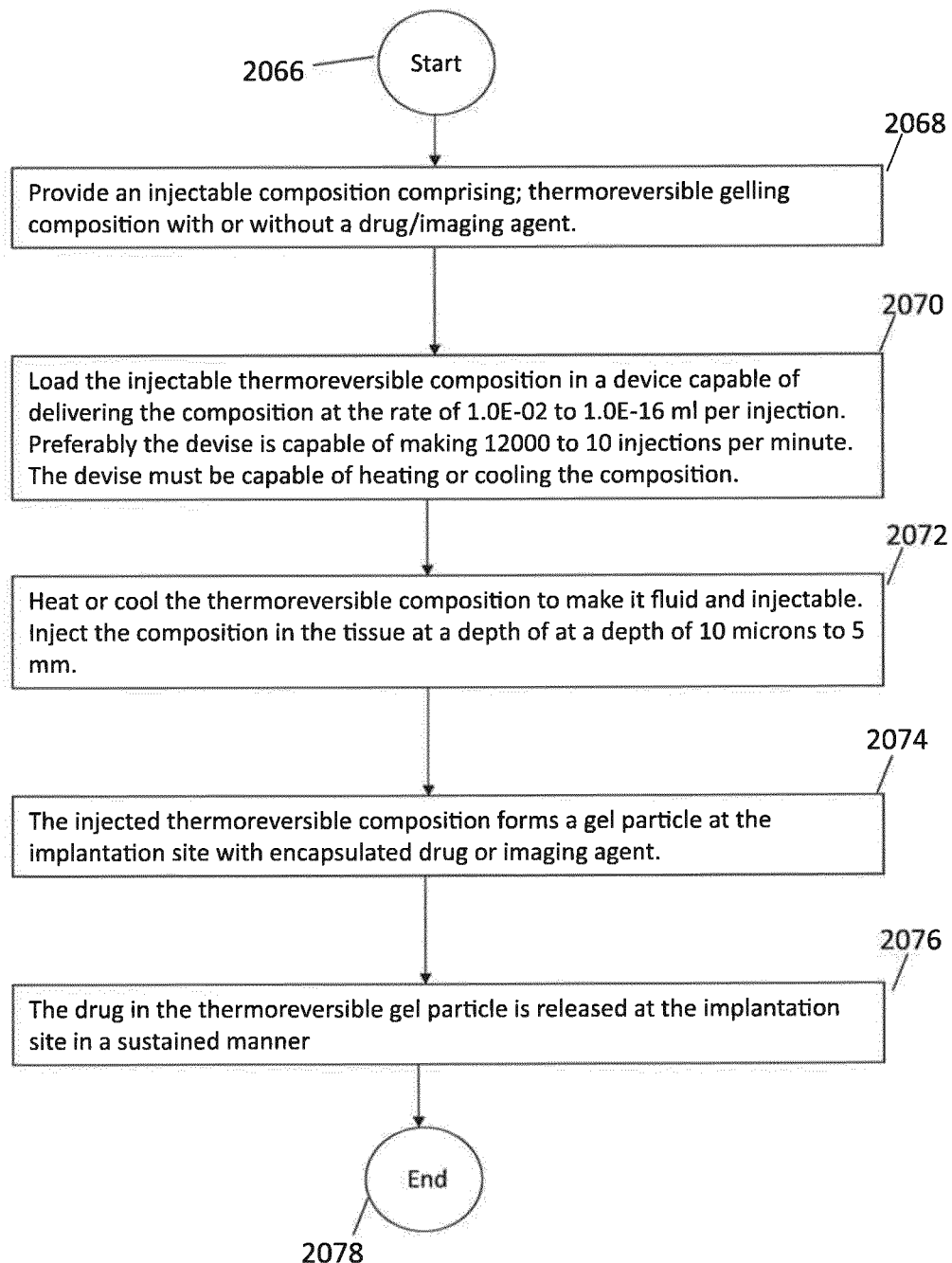
FIG. 8D denotes an illustrative flow chart depicting a method for injecting drug bearing microparticles in an alternate embodiment.

FIG. 8D denotes a flow chart depicting the sequence of steps followed in an embodiment wherein the injectable composition comprises of a thermoreversible gelling composition with or without a combination of drug and an imaging agent.

At step 2068, an injectable composition as per predetermined concentration and formulation is provided. At step 2070, said composition is loaded in the device capable of delivering the composition at the rate of 1.0E-02 to 1.0E-16 ml per injection. Preferably the devise is capable of making 12000 to 10 injections per minute. At step 2072, the thermoreversible composition is heated or cooled to make it fluid and injectable prior to injection. The composition is injected in the tissue at a depth of at a depth of 10 microns to 5 mm. At step 2074, injected thermoreversible composition forms a gel particle at the implantation site with encapsulated drug or imaging agent. At step 2076, the drug in the thermoreversible gel particles released at the implantation site in a sustained manner.

Figure 9A:
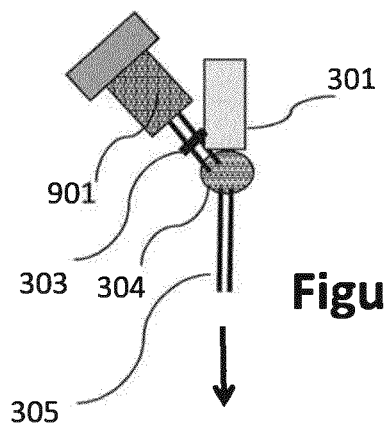
FIG. 9A shows a partial schematic representation of an injection device apparatus in an embodiment of the invention wherein the injectable composition comprises of a water insoluble drug dissolved in a biocompatible solvent.
Figure 9B:
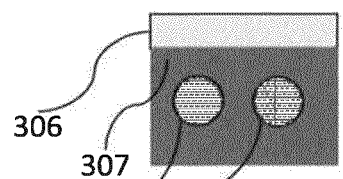
FIG. 9B is a schematic representation of the epidermis layer and dermis layers along with injected composition droplets.
Figure 9C:
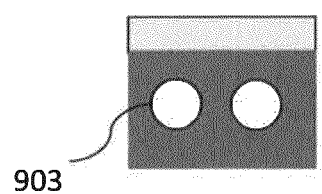
FIG. 9C shows a partial schematic representation of the epidermis layer and dermis layers along with injected composition retained at the implanted site for local sustained drug delivery. The solvent in the injected composition is dispersed in the tissue leaving behind drug crystals for sustained drug delivery.

FIGS. 9A through 9C show a partial schematic representation of a method for local delivery of injectable composition comprising water insoluble drug dissolved in a biocompatible solvent or solution at a local site inside the human or animal body such as dermis layer of the skin tissue. The injectable composition is loaded inside the injection device capable of injecting the composition at 10 to 12000 injections per minute. During each injection the device can deliver 1.0E-02 to 1.0E-16 ml of injectable composition.

After injecting the composition, the solvent in the composition is dissipated by the surrounding tissue precipitating the drug crystals at the injection site. The drug crystals slowly dissolve in the tissue and deliver the drug in a sustained manner.

FIG. 9A shows a partial schematic representation of the injection device apparatus wherein 301 represents an oscillation apparatus that is used to oscillate the injection needle 305. The 301 could be magnetic coils and other parts of the tattoo machine. 901 represents an injectable composition reservoir, which is connected to the temporary reservoir 304 via a flow control valve 303. The valve controls the flow of injectable composition to the needle. The oscillating needle delivers the injectable composition from 304 in the skin tissue. An epidermis layer 306 and dermis layers 307 along with injected composition droplets 902 are schematically shown in FIG. 9B. As shown in FIG. 9C, the solvent in the injected droplets is dissipated or dissolved in the tissue leaving behind or precipitating the drug particles designated as 903. The drug particles release the drug at the injection site in a sustained manner by slow dissolution of crystals.

Figure 9D:
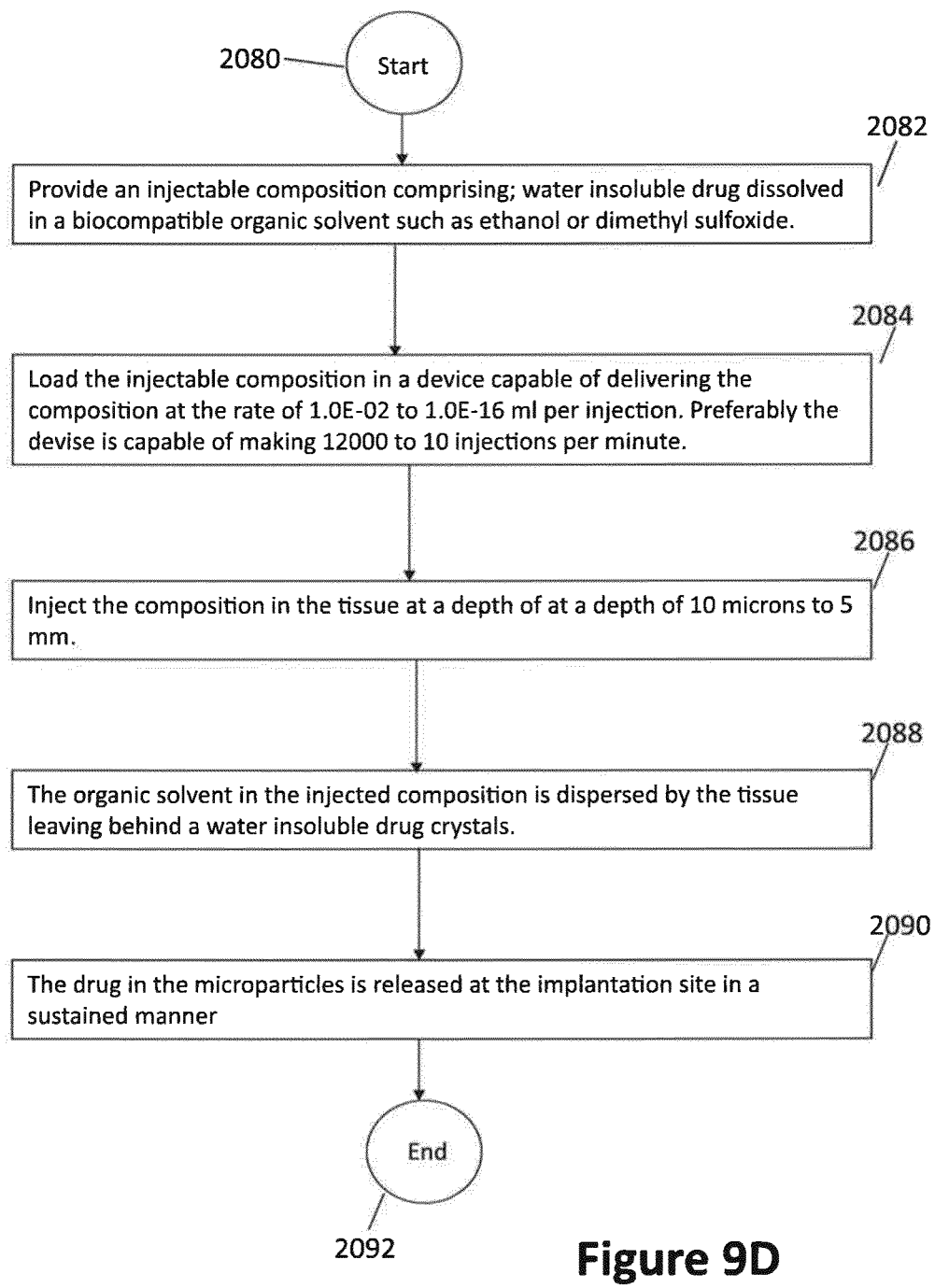
FIG. 9D denotes an illustrative flow chart depicting a method for injecting drug bearing microparticles in an alternate embodiment.

FIG. 9D denotes a flow chart depicting the sequence of steps followed in an embodiment wherein the injectable composition comprises of water insoluble drug dissolved in a biocompatible organic solvent such as ethanol or dimethyl sulfoxide.

At step 2082, an injectable composition as per predetermined concentration and formulation is provided. At step 2084, said composition is loaded in the device capable of delivering the composition at the rate of 1.0E-02 to 1.0E-16 ml per injection. Preferably the devise is capable of making 12000 to 10 injections per minute. At step 2086, the composition is injected in the tissue at a depth of at a depth of 10 microns to 5 mm. At step 2088, the organic solvent in the injected composition is dispersed by the tissue leaving behind a water insoluble drug crystals. At step 2090, the drug in the microparticles released at the implantation site in a sustained manner.

FIGS. 10A through 10C show a partial schematic representation of a method for local delivery of drug wherein the drug is synthesized in situ by a chemical reaction. The method also enables to carry out other useful chemical reactions such as tissue crosslinking or initiating chemical reactions (crosslinking reactions) initiated or catalyzed by tissue fluids. The exemplary compositions comprise metal salts dissolved in a biocompatible fluid such as water. Illustrative injectable composition such as silver nitrate solution in water is loaded inside the injection device capable of injecting the composition at 10 to 12000 injections per minutes. During each injection the device can deliver 1.0E-02 to 1.0E-16 ml of injectable composition. After injecting the composition, the silver ions in the injected solution react with chloride and other ions present naturally in the tissue forming silver chloride salt, or other silver salt which precipitates at the injection site. The precipitated silver chloride slowly dissolves and release silver ion in a sustained manner.

FIG. 10A shows a partial schematic representation of the injection device apparatus wherein 301 represents an oscillation apparatus that is used to oscillate the injection needle 305. 301 could be magnetic coils and other parts of the tattoo machine. 1001 represents an injectable composition reservoir, which is connected to a temporary reservoir 304 via a flow control valve 303. The valve controls the flow of injectable composition to the needle. The oscillating needle delivers the composition from the 304 in skin tissue. An epidermis layer 306 and dermis layers 307 along with injected composition droplets 1002 are schematically shown in FIG. 10B. As depicted in FIG. 10C, the silver nitrate reacts in situ with the natural tissue fluids present at the injection site forming silver chloride and other water insoluble silver salts 1003 which precipitate at the injection site. The newly formed silver salts release silver ion producing therapeutic and antimicrobial effect. The silver salt could be protected from the ambient light to prevent unwanted photo-decomposition by the visible or UV light.

Figure 10D:
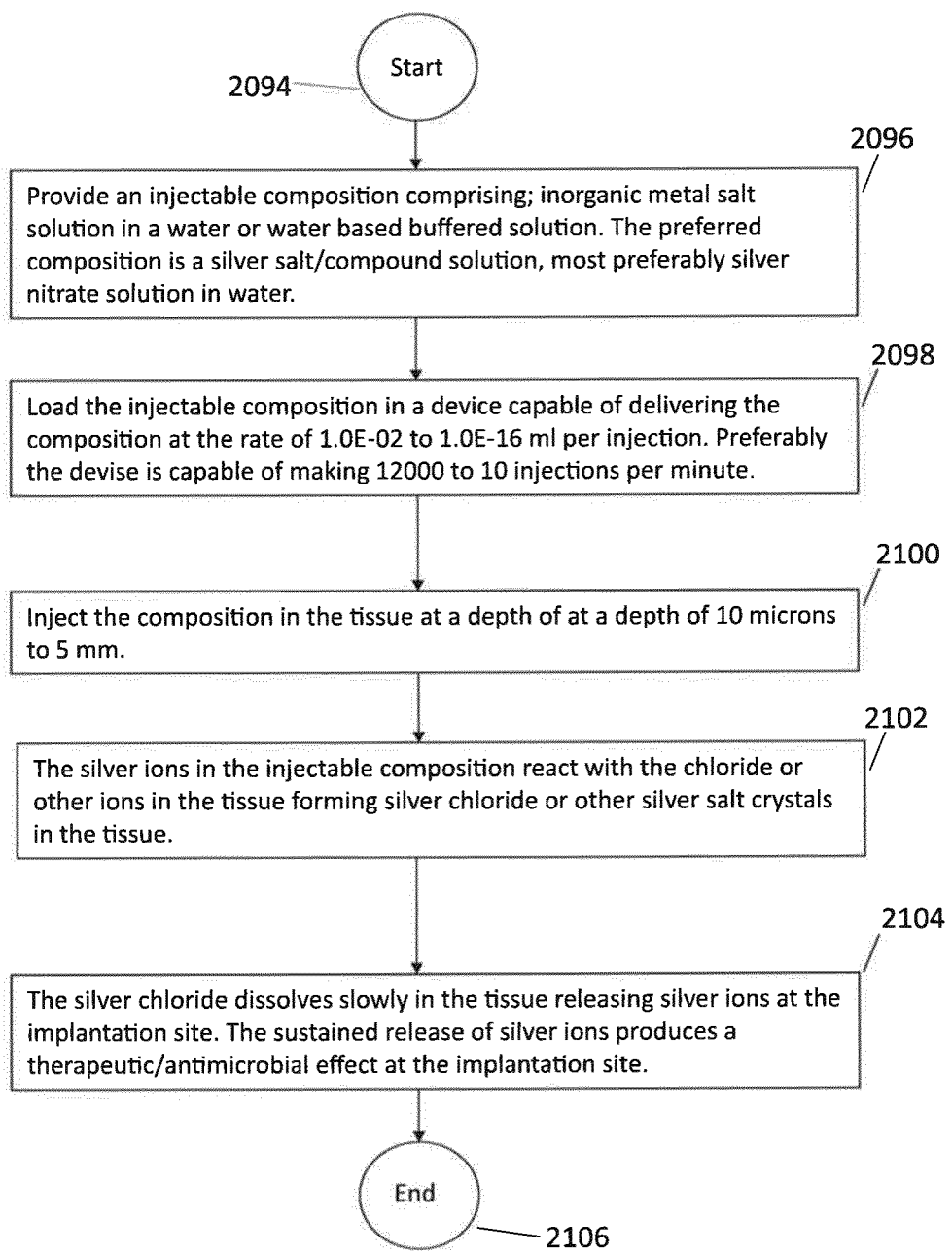
FIG. 10D denotes an illustrative flow chart depicting a method for injecting drug bearing microparticles in an alternate embodiment.

FIG. 10D denotes a flow chart depicting the sequence of steps followed in an embodiment wherein the injectable composition comprises of an inorganic metal salt solution in a water or water based buffered solution. The preferred composition is a silver salt solution, most preferably silver nitrate solution in water.

At step 2096, an injectable composition as per predetermined concentration and formulation is provided. At step 2098, said composition is loaded in the device capable of delivering the composition at the rate of 1.0E-02 to 1.0E-16 ml per injection. Preferably the devise is capable of making 12000 to 10 injections per minute. At step 2100, the composition is injected in the tissue at a depth of at a depth of 10 microns to 5 mm. At step 2102, the silver ions in the injectable composition react with the chloride or other ions in the tissue forming silver chloride or other silver salt crystals in the tissue. At step 2104, the silver chloride dissolves slowly in the tissue releasing silver ions at the implantation site. The sustained release of silver ions produces a therapeutic or antimicrobial effect at the implantation site.

Figure 11A:
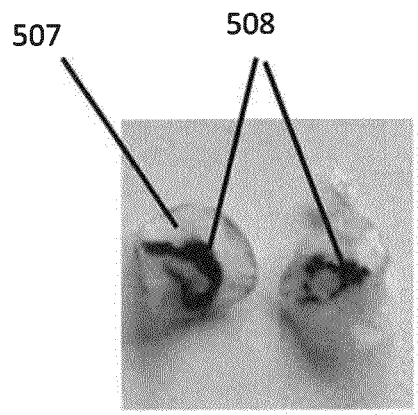
FIGS. 11A and 11B show colored compositions infused in a prosthetic tissue surface in embodiment of the invention.

FIG. 11A depicts illustrative images of a dehydrated uncrosslinked biodegradable pericardial tissue designated as 507 that is infused with colored particles of the liquid formulation. 508 shows infused particles, which cannot be removed by rubbing or washing indicating that it is embedded in the tissue.

Figure 11B:
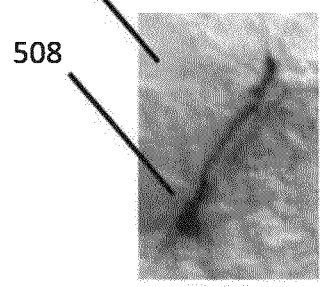

FIG. 11B shows illustrative images of a glutaraldehyde crosslinked porcine submucosa tissue infused with brown particles in the form of line wherein 508 refers to the infused particles. 509 denotes the tissue surface.

Figure 11C:
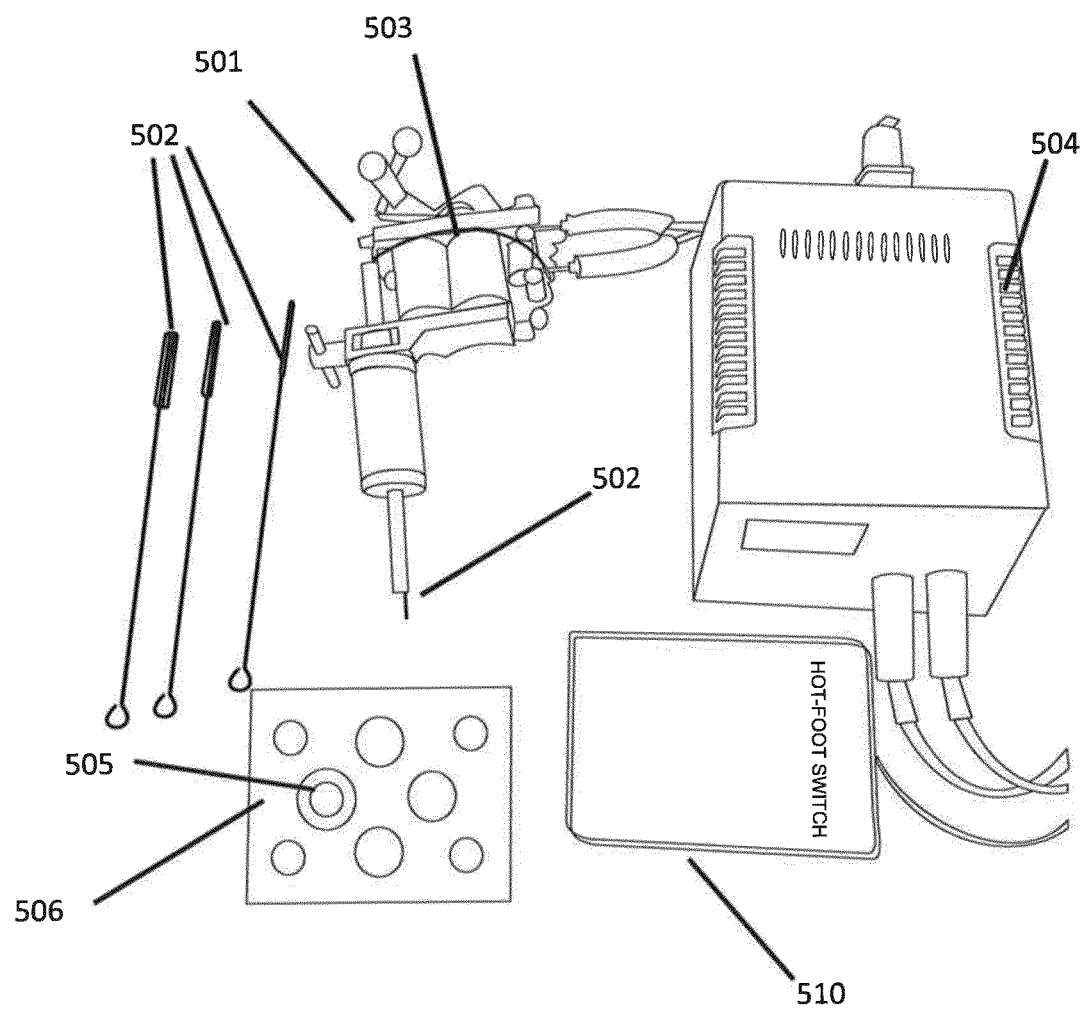
FIG. 11C shows a partial schematic representation of an injection device apparatus in an embodiment of the invention used to infuse colored compositions in a prosthetic tissue surface or live tissue surface.

FIG. 11C shows a partial sketch of an oscillating needle apparatus and system used to infuse compositions in a prosthetic tissue surface or live tissue surface. Preferably the oscillating needle apparatus is a commercially available tattoo machine. 501 shows an oscillating needle apparatus with an oscillating needle mounted inside the apparatus. Needles can be of different diameter size and shape with multiple openings and are designated as 502. 503 shows a coil which controls the oscillation of the needle. 504 shows a power supply source which controls the voltage and therefore oscillation speed or frequency of the needle 502. 510 shows a foot paddle which can turn the machine oscillation on or off by pressing the paddle. 506 is an injectable composition or ink holder stand and 505 shows a liquid color formulation with colored particles, which can be infused in the tissue. The oscillating needle machine shown above can also be used to infuse the particles inside the live tissue, pericardial and submucosa tissue. The oscillating needle machine shown above is used to infuse the particles inside the live rat skin tissue, pericardial and submucosa tissue.

Figure 12A:
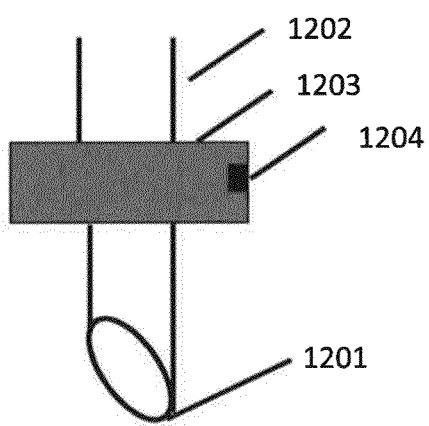
FIG. 12A shows a partial schematic representation of oscillating needle with built in injectable composition reservoir.
Figure 12B:
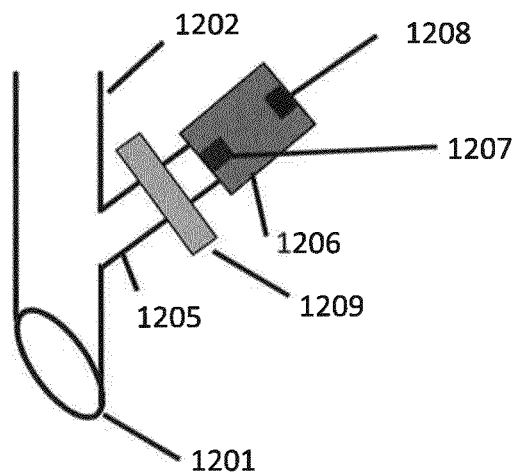
FIG. 12B shows oscillating needle with sidearm that serves as a reservoir for injectable composition.

FIGS. 12A through 12B show a partial schematic representation of an oscillating needle with injectable composition reservoir.

FIG. 12A is a partial schematic representation of oscillating needle with built in injectable composition reservoir designated as 1203. 1201 shows the edge of the needle that goes in and out of tissue and 1202 refers to the part of needle that can be attached to the oscillating mechanism apparatus. The reservoir 1203 may hold sterile injectable composition that may be gravity fed via 1201 for tissue deposition. The reservoir may have an opening or window 1204 which may be used to deposit or fill the injectable composition in the reservoir.

FIG. 12B shows oscillating needle with a sidearm or branch 1205 that serves as a reservoir for injectable composition. The sidearm may feed the injectable composition via gravity or other means to the oscillating needle edge 1201 for deposition inside the tissue. An optional control valve 1209 may be used to control the feed rate during deposition. A disposable reservoir 1206 may be attached to the needle arm via "press fit" type arrangement 1207. The reservoir may also have loading window 1208 to fill or refill the injectable composition.

FIGS. 13A through 13D show partial schematic representation of one of the drug deposition processes via oscillating needle injection. The injectable composition is deposited using oscillating needle described in this invention.

Figure 13A:
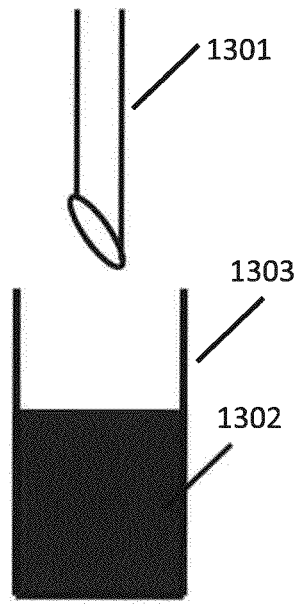
FIG. 13A shows oscillating needle used in this invention and a sterile injectable composition reservoir.
Figure 13B:
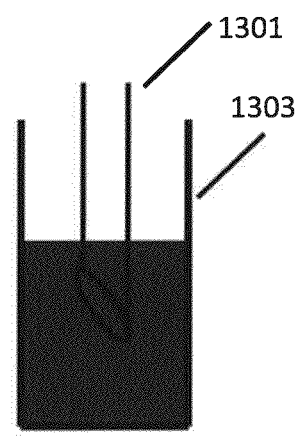
FIG. 13B shows the insertion of the needle in the liquid reservoir for filling the needle for tissue deposition.
Figure 13C:
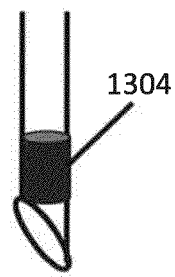
FIG. 13C shows the liquid being filled in the needle due to surface tension forces.
Figure 13D:
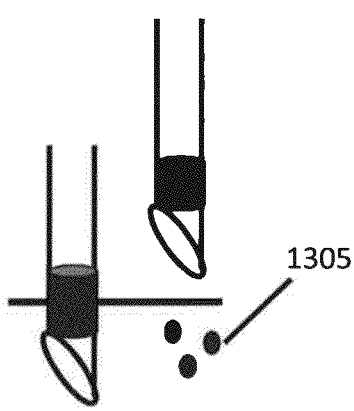
FIG. 13D shows the liquid composition filled needle (liquid held in place via capillary forces) while being inserted into tissue bed for local drug therapy.

FIG. 13A shows an oscillating needle 1301 used in this invention and a sterile injectable composition 1302 present in a reservoir 1303 in a fluid, injectable state. FIG. 13B shows the insertion of the needle 1301 in the fluid reservoir 1303 for filling the needle for deposition of the injectable composition in tissue. The liquid 1304 is filled i.e. sucked in the needle due to surface tension forces as shown in FIG. 13C. FIG. 13D shows the liquid composition filled needle (liquid held in place via capillary forces) inserted into tissue bed for local drug therapy. The liquid composition is deposited as small droplets in the tissue 1305. The droplets may undergo more changes (swelling, crosslinking, solidification, precipitation and the like) depending in the injectable composition used. The deposited droplets release the drug locally in the surrounding tissue for local or systemic therapeutic effect.

Figure 14:
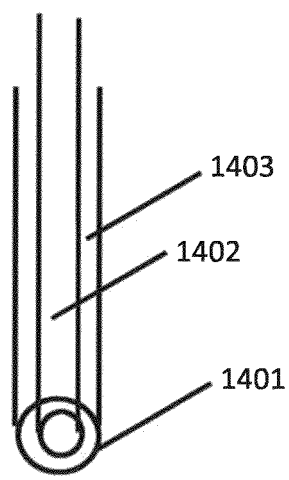
FIG. 14 shows partial schematic representation of oscillating needle with multiple lumens that may be used in this invention.

FIG. 14 shows partial schematic representation of oscillating needle with a plurality of lumens that may be used in an embodiment of this invention. The needle has a sharp edge 1401 for tissue insertion and multiple lumens, which may be used to deposit two or more injectable compositions using the same needle. The inner tube or lumen 1402 may be used to deposit an injectable composition (PLGA solution in DMSO along with drug as an example) and the outer lumen 1403 may used to deposit saline solution, which may help to accelerate the precipitation of PLGA polymer. The two lumens may also be used to deposit precursors of crosslinkable compositions, which upon deposition can react or crosslink to form crosslinked compositions.

FIGS. 15A through 15D show partial schematic representation of local drug therapy made using compositions and methods described in this invention.

Figure 15A:
FIG. 15A is a partial schematic representation of a closed surgical incision treated in an embodiment.
Figure 15B:
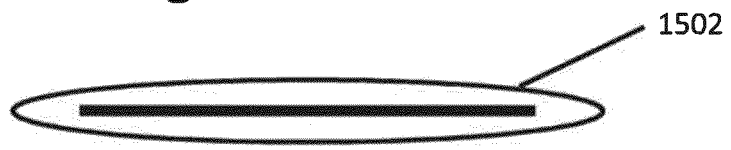
FIG. 15B is a partial schematic representation of an injectable composition deposited in the surface tissue surrounding the surgical incision in an embodiment of this invention wherein the deposition is visible to the naked human eye and can provide sustain release of therapeutically effective drug dose such as antibiotic to the surgical wound.
Figure 15C:
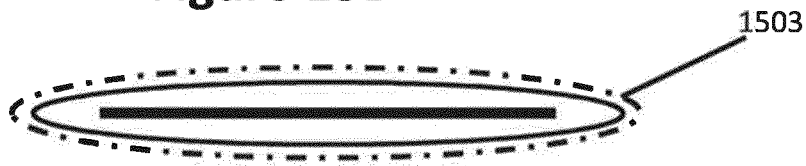
FIG. 15C is a partial schematic representation of an injectable composition deposited in the surface tissue surrounding the surgical incision in an embodiment of this invention wherein the deposition is used to reduce the scar tissue formation or other useful clinical effect.
Figure 15D:
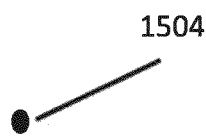
FIG. 15D schematically shows acne or mouth blister that needs to be treated using local drug therapy.
Figure 15E:
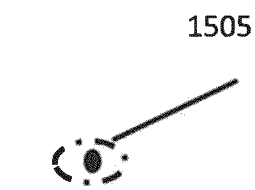
FIG. 15E shows the deposition of drug surrounding acne or blister that provide local sustained drug delivery to the acne or blister.

FIG. 15A schematically represents a closed surgical incision 1501 such as incision wound made during cesarean section operation. FIG. 15B shows the deposition of injectable composition in the surface tissue surrounding the surgical incision. The deposited composition is visible to the naked human eye (shown as a solid line designated as 1502 and can provide sustain release of therapeutically effective drug dose such as antibiotic to the surgical wound. If desired, another drug (shown as dotted line designated as 1503, represented in FIG. 15C. Solid line and dotted line may also represent sustained releasing compositions releasing the same drug at different rate of release. The solid line may be a fast release or burst release composition (1-3 days total release as an example) and dotted line may represent as slow release composition (1-30 days as an example). The composition can be deposited in the skin tissue surrounding the surgical wound using methods taught in the invention to reduce the scar tissue formation or other useful clinical effect. FIG. 15D schematically shows acne or mouth blister 1504 that needs to be treated using local drug therapy. FIG. 15E shows the deposition of drug 1505 surrounding acne or blister 1504 that provide local sustained drug delivery to the acene or blister.

Figure 16A:
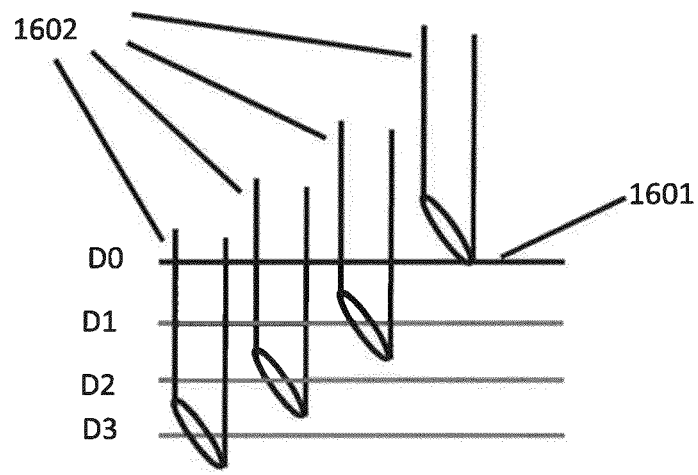
FIGS. 16A, 16B, 16C are partial schematic representations of deposition of injectable compositions at various depths in the tissue and in various two or three dimensional shapes and patterns.
Figure 16B:
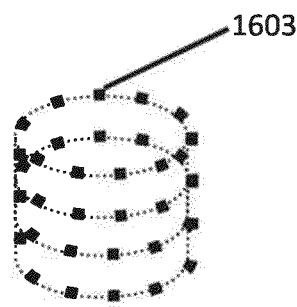
Figure 16C:
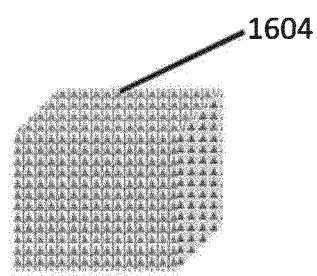

FIGS. 16A through 16C show a partial schematic representation of deposition of injectable compositions at various depths in the tissue and in various two or three dimensional shapes and patterns.

FIG. 16A shows the tip of an injectable needle 1602 of an oscillating needle device penetrating at various depths (D1, D2 and D3 for example). 1601 represents an imaginary tissue surface at zero depth of penetration (D0). The needle 1602 of an oscillating needle device can be tuned or "dialed in" to penetrate at predefined tissue depths (D1, D2 and D3). FIG. 16B shows a deposition pattern of eleven needle injectable device whose needles are arranged in a circular shape and can be dialed in to deposit at various depths. Upon deposition at various depths (D1, D2 and D3 as an example), a cylindrical pattern of deposited material is formed. The injected compositions in the shape of a hollow cylinder designated as 1603 will release the drug at a local site in the body in a sustained manner.

FIG. 16C shows a different deposition pattern of an injectable composition 1604 injected in a tissue in cubical pattern. A twenty four needle injectable device whose needles are arranged in a rectangular fashion (as shown in FIG. 16C) and is capable of injecting at various depths. Upon deposition at various depths, a cubical pattern of deposited materials is formed which can provide local drug delivery in the deposited area.

These embodiments show that the injectable composition can be injected in the tissue at predetermined depths which can be customized as per requirement.

Figure 17:
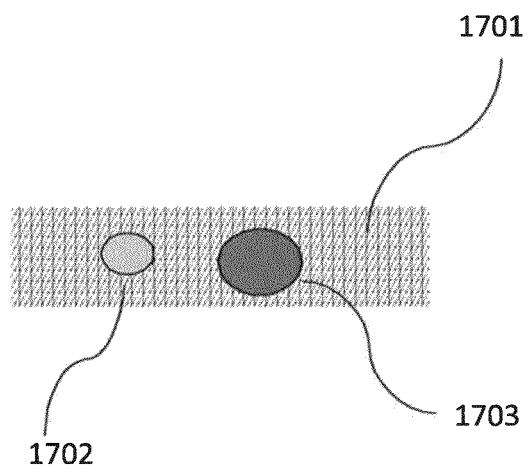
FIG. 17 represents two forms of an injected droplet in a tissue layer.

FIG. 17 denotes an injected droplet 1702 embedded in tissue layer 1701. In an embodiment of the invention the injected droplet may undergo further additional physical and chemical changes (swelling or increase in volume/size, polymerization, crosslinking, cooling/crystallization, gelling, precipitation of polymers or drugs, chemical reactions with tissue fluids and the like) that can enable sustained delivery of drugs. 1703 represents an injected droplet that has increased in volume.

Figures 18A, 18B, 18C:
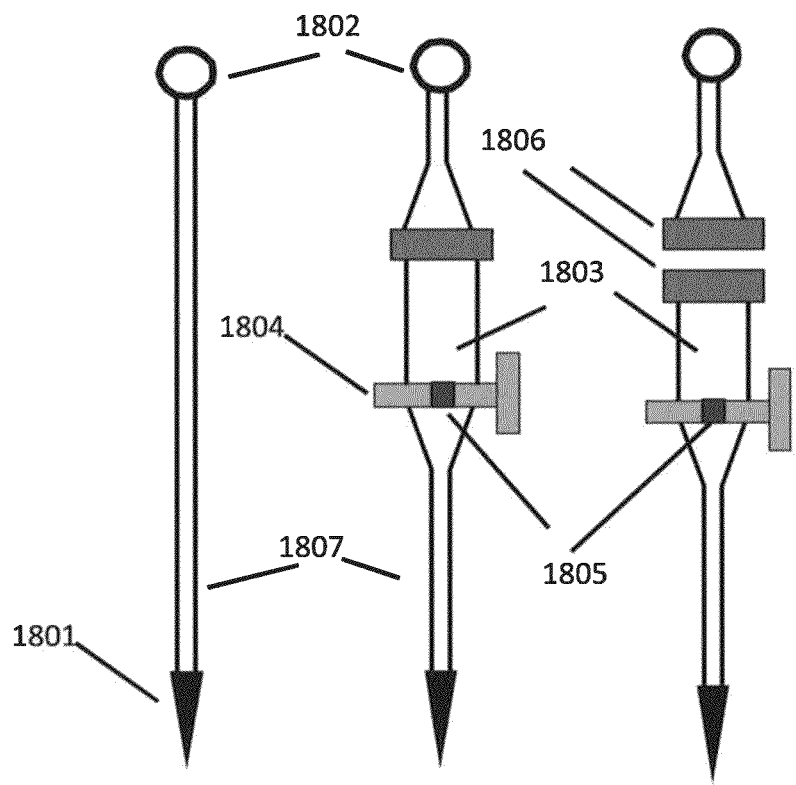
FIGS. 18A, 18B and 18C are partial schematic representations of a conventional tattoo needle and injection needle with reservoir and flow control valve as described in this invention.

FIGS. 18A through 18C are partial schematic representations of conventional tattoo needle and injection needle with reservoir and flow control valve described in this invention.

FIG. 18A shows conventional tattoo needle that is used in the tattoo art. The needle has circular metal ring 1802 which is generally used to attach to the tattoo machine and needle body 1807 which may be hollow or solid metal tube. The needle has an edge/tip 1801 which can be inserted in the tissue/skin and has small tip reservoir (not shown) that can hold small amount of tattoo ink which can be filled many times during tattooing process. FIG. 18B shows modified version of FIG. 18A needle wherein the needle has injectable composition reservoir 1803, a control valve 1804 and optional removable mechanism 1806. The injection needle composition is gravity fed to needle tip via control valve 1804 and through a valve opening 1805. The rotation of the valve 1804 can control the amount of composition fed to the needle tip. FIG. 18C is the same needle as FIG. 18B wherein the top portion of can be separated and reattached using snap fit or screw-top type mechanism to fill or refill the reservoir.

Figure 19:
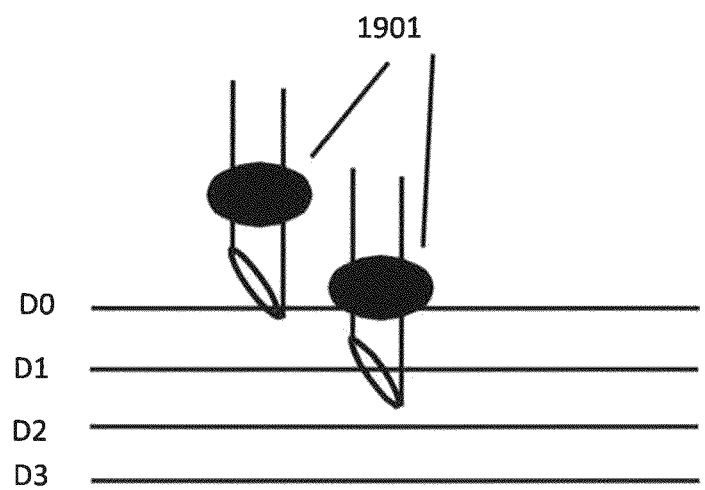
FIG. 19 represents an injection device wherein the needle is provided with stoppers at predetermined locations to control the depth of penetration in the tissue layer.

FIG. 19 represents an injection device wherein the needle is provided with stoppers on the needle outer surface at predetermined locations to control the depth of penetration in the tissue layer. Such an embodiment of the injection device allows precise and customized control over the depth the needle must travel into the tissue layer.

Figure 20:
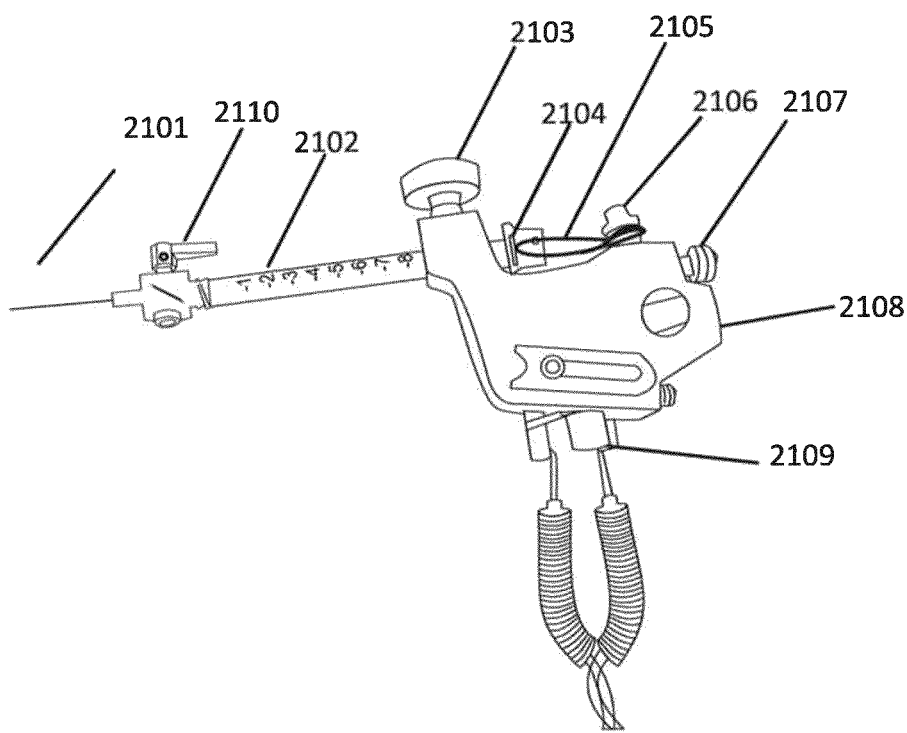
FIG. 20 represents an alternate embodiment, which uses an oscillatory injection device in an adaptation of a rotary tattoo machine.

FIG. 20 denotes an alternate injection device, which is a standard rotary tattoo machine modified/adopted so that it can be used in this invention. The adopted machine comprises an oscillating needle (syringe needle) 2101 which is connected to a syringe via flow control vale 2110, a 1 ml disposable syringe (functioning as an injectable composition reservoir) 2102, a screw that can help to immobilize the syringe 2103 which is loose enough to permit oscillations to the syringe, an opening 2104 in the syringe from where injectable liquid can be added in the syringe, a metal wire 2015 with a circular hook similar to standard tattoo needle that connects to the oscillating bar 2106 of the rotary tattoo machine. 2107 is screw that controls oscillation length (feature of the machine). 2108 is an electric motor and swash mechanism housing that oscillates the syringe needle and 2018 denotes 12 V electrical supply contacts for the electric motor inside the housing.

2101, 2110, 2102 and 2105 may be provided as a one unit assembly (oscillating needle with injection reservoir similar to described in FIGS. 18A through 18C).

Figure 21A:
Figure 21B:
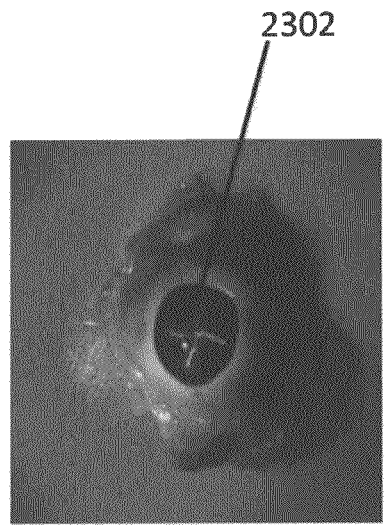
Figure 21C:
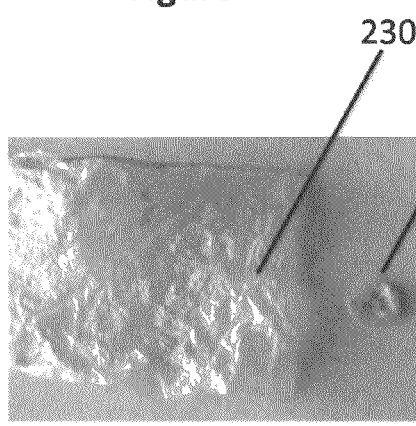
Figure 21D:
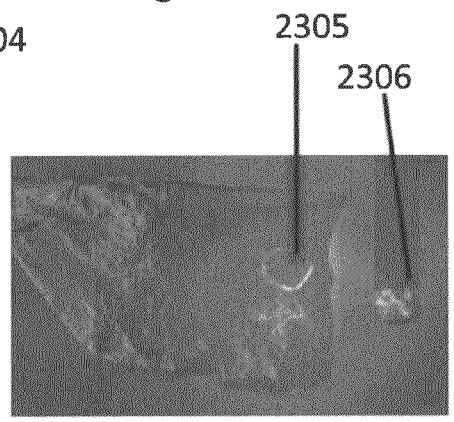

FIGS. 21A-21B represent exemplarity bioprosthesis tissue, ophthalmic tissue and a muscular tissue implanted with biodegradable microparticle composition with fluorescent dye as a visualization agent/model drug or sustained releasing rifampin composition. In FIG. 21A, 2301 shows an illustrative biodegradable polymer (PLGA) based biodegradable sustained drug delivery composition comprising rifampin as an exemplary drug encapsulated in PLGA and is injected using an oscillating needle in the chicken leg muscle. The implanted composition has faint red color of antibiotic rifampin and has a shape of a circular ring and solid square and is embedded in the surface layer of the muscle. The embedded rifampin composition cannot be removed by washing with PBS solution or cannot be rubbed off. 2302 is PLGA based sustained drug delivery composition injected in the porcine cornea tissue. The composition has coumarin 6 as a model drug and fluorescent compound encapsulated in a PLGA polymer. The composition is embedded in the cornea tissue and is fluorescent under blue light. The plus sign shape of injected composition is clearly visible under blue light. In FIG. 21C, 2303 and 2304 represent PLGA based biodegradable composition with coumarin 6 as model fluorescent drug embedded in a thin glutaraldehyde crosslinked porcine submucosa tissue and unfixed bovine pericardium tissue respectively. In FIG. 21D, 2305 and 2306 are same as 2303 and 2304 except viewed under blue light. The fluorescence of embedded microparticle composition in the bioprosthesis tissue is clearly seen.

Figures 22A, 22B, 22C:
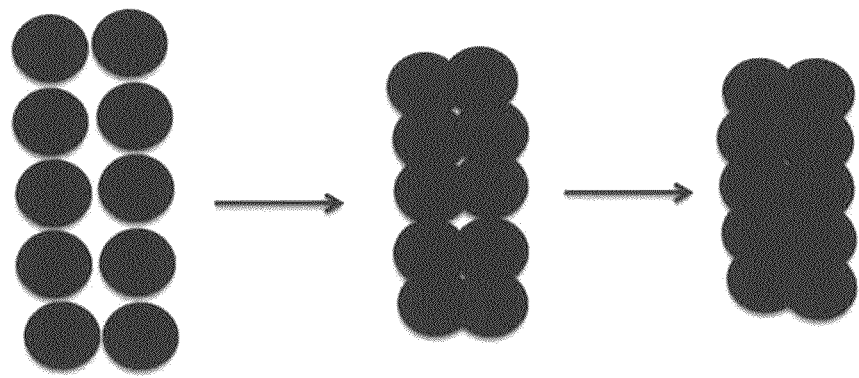
FIGS. 22A through 22C show a partial schematic representation of a method of delivering an injectable liquid composition wherein the films or implants are synthesized/made insitu by a fusion process to form a film or implant in situ. The film or implant may contain a drug.

FIG. 22A to 22C show partial schematic representation of injected liquid droplets fusing or coalescing to form a bigger droplet of desired shape and size. The fused liquid undergo additional changes such as precipitation of polymer, solidification of melted polymer or gelation of thermoreversible composition to form film or implant in situ. FIG. 22A schematically represents injected droplets inside the tissue, which are injected close to each other in manner such that the fusion of liquid particles is possible or can occur. FIG. 22B is same as FIG. 22A except a partial fusion of liquid droplets has occurred but the pattern is maintained. FIG. 22C shows almost complete fusion of injected droplets to form a bigger liquid droplet with the pattern maintained. The fused liquid droplet undergo further transformation such or precipitating the polymer and thus forming the polymer film or implant in situ. The device allows for small individual discrete depots that stay separate or that fuse to form a larger depot; where both small and large depots have the pattern of the injection, which may or may not be colored with an invisible ink.

The colored compositions and microspheres can include colorant that is finely divided into small particles on the sub-micron or nano size range or smaller sizes to single molecule. This allows for the colored injection to be biodegradable. It has been found that colorant smaller 1 micron may be capable of migrating from the side and being flushed from the biological system. However, it is thought that smaller particles such as 100 nm or smaller have more ability to migrate from the injection site and be flushed from the system. Thus, the scale of the colorant or visualization agent is small enough to form a temporary tattoo. This may be less than 100 nm, more preferably less than 50 nm, and most preferably less than 10 nm.

On the other hand, the microspheres can be of a size that stays localized and degrade at the site of injection. The size of the microspheres to stay localized can be inverse of the colorant. As such, the microspheres can be larger than 500 nm, more preferably larger than 1 micron, more preferably larger than 10 microns, more preferably larger than 100 microns, with the caveat of being less than 300 microns.

When the microspheres include the colorant, the degradation of the microspheres can be observed by the bioerosion of the tattoo by the colorant particles being released and migrating from the site of injection. This allows the colorant to be used as a marker for the amount of agent that is injected as well as the amount of agent that is escaping the microspheres and the rate of the release of the agent from the microspheres. The size of the injection region can provide a dose amount of the agent, and the rate of color fade can provide an agent release profile.

This invention teaches methods and compositions for infusing injectable compositions, preferably with drug or imaging agents in the body or skin or in the tissue of a bioprosthesis.

Different embodiments of the present invention are described by referring to various industrial applications and examples as provided.

I. Method of Infusion of Compositions Using Oscillating Needle Device

In this invention, the injectable compositions preferably comprising of drugs or imaging agents are infused inside the human body or bioprosthesis tissue using a surgical procedure or MIS surgical procedure by methods wherein the injectable compositions are delivered using an oscillating needle or using a needle that deposit extremely small volume of composition per injection.

In the conventional method as shown schematically in FIG. 2A, the syringe dumps the required amount of liquid 202 generally at one injection site forming a pool of liquid 203 at the injection site. Generally all the liquid is dispensed at once forming a blob of liquid. In the present invention as illustrated in FIGS. 2B and 2C, an oscillating needle 305 is used to dispense the liquid or injectable fluid composition 202 in the tissue. This oscillation process is generally repeated several times per minutes, preferably 10 to 12000 times per minute, even more preferably 3000 times to 9000 times per minute, dispensing several droplets with preferred droplet volume 1.0E-02 to 1.0E-16 ml, or from 1.0E-03 to 1.0E-15 ml, or from 1.0E-05 to 1.0E-10 ml, or from 1.0E-07 to 1.0E-08 ml. The oscillating needle is generally moved during insertion process in a large area of the skin or body to distribute the number of droplets in a larger area. Further, as disclosed in this invention, the droplets may also undergo further additional physical (increase it volume, phase change and the like) and/or chemical changes (polymerization, crosslinking, precipitation of polymers or drugs, chemical reactions with tissue fluids and the like) that enable sustained delivery of drugs. The comparison of injection methods described in this invention and conventional syringe injection method is provided in Table 1.

TABLE 1

COMPARISON OF DRUG DELIVERY USING CONVENTIONAL SYRINGE METHOD AND METHODS DESCRIBED IN THIS INVENTION.

| CATEGORY | CONVENTIONAL DELIVERY OF FLUIDS WITH DRUGS VIA SYRINGE | DELIVERY OF FLUIDS WITH DRUGS USING METHODS DESCRIBED IN THIS INVENTION |
| --- | --- | --- |
| Place of injection | Generally at one place | Several injections over a wider area (generally 2 sq. mm or larger) |

TABLE 1-continued

COMPARISON OF DRUG DELIVERY USING CONVENTIONAL SYRINGE
METHOD AND METHODS DESCRIBED IN THIS INVENTION.

| CATEGORY | CONVENTIONAL DELIVERY OF FLUIDS WITH DRUGS VIA SYRINGE | DELIVERY OF FLUIDS WITH DRUGS USING METHODS DESCRIBED IN THIS INVENTION |
|---|---|---|
| Injection rate | Generally 1-2 injections per minutes | Generally 10-12000 injections per minutes. |
| Volume of injectable liquid | Generally 0.1 ml to several per injection. | Generally 1.0E–02 to 1.0E–16 ml ml per injection. |
| Special device needed | No need for special device. A simple syringe can do the job. | May need specialized device to oscillate the needle at a controlled rate and deliver the fluid/drug. |
| Precise control over drug dose. | Possible but difficult | Generally possible. |
| Method of delivery | Generally continuous delivery of all fluids in one application. | Non-continuous or discrete way of delivery. |
| Visual control of drug delivery composition | Generally not possible unless composition is colored. | Composition is intentionally made colored so that human eye with or without the use of imaging machine can detect the amount injected. |
| Surface area of microparticles | Generally low surface area. | Generally with high surface area. |

It is clear from the Table 1 that the methods proposed in this invention have several unique advantages. The inventive method dispenses a very small volume of injectable composition per injection. This enables to dispense precise amount of drug delivered at a local site inside the body. It is especially useful when drug has a high toxicity (Botox for example). Another advantage of this process is that the microparticles capable of releasing drugs can be made "in situ" inside the tissue. This potentially eliminates the complicated process of making sustain drug delivery microparticles in a factory setting and using them for sustained drug delivery. The elimination of microspheres or microparticles manufacturing in a factory setting can potentially save significant costs for the consumer.

The microspheres or microparticles made in a factory setting have large surface area, which makes them susceptible for viral, bacterial or fungal or other contamination when exposed to air. In this invention, microspheres or microparticles can also be made "in situ" inside the tissue, and therefore the potential of bacterial contamination is significantly reduced.

II. Oscillating Needle Device Apparatus

The inventive oscillating needle injectable device apparatus described in this invention comprises two main parts; an injection needle and a device with oscillation mechanism that is attached to the needle, which provides controlled oscillations to the needle. Optionally, one or more injectable composition reservoirs may be attached to device and used to delver the injectable fluids/compositions inside the needle for deposition inside the body. In addition, a small mixing chamber may also be present in the device wherein injectable compositions can be mixed prior to injection. The composition from the mixing chamber may be added in the needle via a flow control valve. A fluid pump or other methods to pressurize the fluid may be attached to the reservoirs to control the flow rate of injectable composition in the needle. Gravity force may be preferably used to flow the compositions. The reservoir may have one or more controllable flow control valves that can control the flow of injectable composition to the needle.

FIGS. 12A and 12B show a partial schematic representation of an oscillating needle with injectable composition reservoir.

The needle used in the device is preferably made using a hollow metal tube. Other materials such a ceramics, polymer may also be used. Metals such as stainless steel, titanium are preferred to make the needle. The preferred diameter of the injection needle may vary from 10 gauge to 34 gauge, which generally corresponds to outside diameter (OD) of 3.404 mm to 0.19 to mm. The preferred internal diameter (ID) of needle may range from 2.693 to 0.051 mm. The preferred wall thickness of the needle may range from 0.11 to 0.71 mm. The syringe can hold 0.052 microliters/inch to 144.641 microliters/inch injectable liquid/fluid. The preferred dimensions are for illustration only and may be changed if desired. In general, 1 mm or less needle diameter is preferred. The needle diameter will generally depend on the size of injectable composition. For example, the injectable composition may contain microparticles or microspheres ranging from 10-600 micron, then a needle must have lager diameter than 600 microns to accommodate all size of particles. If the injectable composition is a homogeneous solution, then needle diameter smaller than 300 microns is preferred. The injectable device may have one, two, three, four, five or several needles per device. The micro fabrication techniques used in semiconductor industry generally enable to obtain several micro needles (with gauges/sizes smaller than 34 gauge if needed) per square mm area of the device and such devices could also be used. The shape of the injection needlepoint could be varied if needed. The needle point can have various shapes such as taper point, blunt taper point, cutting edge, reverse cutting edge, taper cut, spatula curved and the like. A sharp needle that is easy to penetrate is preferred. In some cases, the outer or inner surface of the needle may be coated to achieve desirable device performance. For example, the outer surface of the needle may be coated with silicone oil, vitamin E, or other biocompatible liquid or lubricant that can provide reduced frication during tissue insertion or device operation. The inner surface of the needle may be coated with a coating that can improve surface wetting (surface tension) of the injectable composition. The coating may be hydrophobic or hydrophobic depending on the injectable composition.

In some embodiments, needle with a plurality of lumens say, two, three, four or five lumens may be used to inject two or more injectable compositions at the same time. Generally 2-4 lumens in a needle may be preferred. The shape of the lumen may be cylindrical, elliptical, rectangular, triangular, pentagonal, or irregular and the like. The most preferred shape is cylindrical. If desired, each lumen may be connected to different injectable composition reservoirs or fluids.

FIG. 14 shows partial schematic representation of oscillating needle with multiple lumens that may be used in this invention. The needle has sharp edge 1401 for tissue insertion and multiple lumens, which may be used to deposit two or more injectable compositions using the same needle. The inner tube or lumen 1402 may be used to deposit injectable composition (PLGA solution in DMSO along with the drug as an example) and the outer lumen 1403 may be used to deposit saline solution, which may help to accelerate the precipitation of PLGA polymer. The two lumens may also be used to deposit precursors of crosslinkable compositions, which upon deposition can react/crosslink to form crosslinked compositions. Each lumen may be connected to different injectable composition reservoir and its feed in to the lumen may be controlled via a control valve. One lumen may be used for deposition of drug delivery composition and the other lumen may have various sensors such as pH, temperature, oxygen level, insulin concentration, injection depth, injection frequency, injection counts and the like. In addition, the lumen may house sensors that count the number of needle oscillation, which may help to "dial in" precise dosage of the drug, composition reservoir level and the like. One or more lumen may be used to deposit the same injectable composition wherein the additional lumen may serve as a temporary reservoir for the composition.

In a preferred embodiment of the present invention, as shown in FIGS. 18A-18C, the injection needle device comprises of a modification of a conventional tattoo needle. In this embodiment, the preferred injection volume of reservoir is greater than 0.05 ml, preferably between 0.1 ml and 100 ml, even most preferably between 0.15 ml to 10 ml. The reservoir may be connected to temporary reservoir on the tip via a flow control valve. Further the reservoir may be provided with level markings to control precise delivery of the injectable composition in the tissue.

The wall of needle inner surface may be textured to hold ink. The surface may be polished so that the composition can be dislodged easily during deposition process.

In one embodiment of the present invention as shown in FIG. 19, the injection needle is modified to have penetration stoppers designated as 1901 at fixed distances from the edge or the tissue insertion point. The stopper could be attached at 1 mm or 2 mm or any other suitable distance from the edge of the needle. The stoppers could be metal disks or beads that are attached/glued to the outer surface of the needle. The diameter of disk or stopper could be 10-10000 percent larger than needle diameter. The stopper offers substantially higher resistance to penetrate inside the tissue and hence the needle cannot penetrate beyond the stopper.

FIG. 19 describes the concept use of penetration stopper. The stoppers could also be made movable so that the depth of penetration can be changed on the same needle. Instead of gluing, the stoppers could be attached by mechanical means such as nut-bolt type arrangement and the like. The use of stopper is just one illustrative method to control depth of penetration. Other methods such as injection device parameters could be used in controlling the oscillation length or depth of penetration via electrical, mechanical or pneumatic means.

The needle can oscillate from one position to another (position A to position B) in a linear fashion but can also take a curved path or other shape path if desired. Linear displacement, going in and out of tissue is most preferred. The needle can oscillate between 5 microns to 10 mm distance (distance between point A and point B) preferably 10 microns to 5 mm, most preferably 20 microns to 3 mm. The needle oscillation enables it to deposit the injectable composition at a depth of 5 microns to 10 mm inside the tissue, preferably 10 micron to 5 mm, most preferably 20 microns to 3 mm depth. In one exemplary embodiment, the depth of needle penetration is controlled by adding or gluing a penetration stopper on the needle. A metal or plastic disk is glued or wielded to the outer surface of the needle at a distance of 1 mm from needle stage. When such needle is inserted inside the tissue, the needle is prevented from entering the tissue beyond the stopper (stopper being bulky cannot penetrate the tissue). Stoppers can be glued at various points (2 mm, 3 mm and the like distance) on the needle surface to achieve a desirable needle penetration depth (2 mm, 3 mm and the like). The needle is oscillated using number of mechanisms, which include electrical displacement, magnetic displacement, hydraulic displacement, ultrasonic displacement, mechanical displacement and the like. A human hand can also be used but is not preferred. One illustrative embodiment teaches use of human hand for multiple injections. In another illustrative embodiment, an electric coil is used to displace a needle (generally referred as tattoo machine needle displacement). Other displacement methods such as found in sewing machine (hand operated as well as electric motor operated) can also be used. In automobile engine, the crankshaft converts or translates reciprocating linear piston movement into rotational movement. Using a similar mechanism, a rotational motion of circulating disk can be converted into linear motion for the oscillating needle displacement. The two illustrative methods, namely hand method and electric coil method, have been used for illustration purpose only and uses of other methods of displacement are anticipated and are considered part of this invention. Any methods of oscillation can be used, provided precise control over number of injections per minute and injection depth is achieved. Electrical methods, mechanical methods, hydraulic, pneumatic and magnetic methods for providing reciprocating oscillation to the needle are most preferred. In some cases, in addition to oscillation, needle may be vibrated using ultrasonic piezoelectric crystals or using other mechanisms to provide additional control over delivery of liquids through the oscillating needle. The vibration helps to dislodge the injected composition from the needle. Other methods of dislodging such as controlled injection of carbon dioxide gas jet or fluid jet (saline solution) may be used to dislodge droplets from the needle. A compact pen like oscillation devices used in making permanent makeup are good examples of preferred devices for providing oscillating needle mechanisms.

In the commercial tattoo making process, colored pigments/particles are inserted under skin's dermis to lock them down in the tissue surface. This is usually done by electric tattoo machine, which has oscillating needle/needles (generally oscillating in the range 3000-9000 times per minutes). The needles moves in and out of tissue surface and insert the tattoo ink/particles in the dermis body about 10 to 2000 micron dip, preferably 100 to 1000 microns dip. The vibration methods used in the tattoo machine could be preferentially be used in this invention. U.S. Pat. Nos. 6,033,421, 6,550,356, 6,626,927, 7,340,980, 8,171,825 and US patent application 2010/0192730 and references therein; cited herein for reference only; describe various methods and designs to make a tattoo machine whose integral part is an oscillating needle.

Designs and mechanism used for needle vibration could also be used in this invention. Information provided in "Tattoo Machine" Tattoo machine—Wikipedia, web page accessed on May 4, 2013 and references therein; cited herein for reference only; could be used to make oscillating needle device described in this invention. Commercial tattoo machines/brands such as provided by TapTatDaddioNeoTat Tattoo Machines; Borg Tattoo Machines; LauroPaolini Italia Tattoo Machines; Pittsburgh Iron Tattoo Machines; Neuma Hybrid Tattoo Machine (Neuma Tattoo Machines, Inc., Granada Hills, Calif.) and the like could be used as oscillating needle delivery devices. Neuma Hybrid Tattoo Machine can vibrate the needle by conventional way using electrical coil as well as using a pneumatic method. The Neuma machine also enables to control the displacement length of the oscillating needle, which can help to control the depth of penetration/implantation using this machine. Tattoo machines, conventional or advanced can be purchased from many commercial vendors known in the tattoo industry art. Such machines may also be purchased from Amazon.com or Ebay.com. Artisans can understand that many variations and designs are possible for the injectable device described in this invention. Such variations are considered as part of this invention.

Many types of oscillating machines can be used in this invention. In a direct drive rotary tattoo machine, a cam wheel or bearing is directly placed on an electric motor shaft. The needle bar is attached to the cam wheel. The needle bar can be connected to the removable injection needle. The circular motion of the cam wheel makes the needle bar move up and down. By changing the average diameter of cam wheel, the up and down motion (oscillation length or depth of penetration) can be changed. In another type of rotary tattoo machine, generally referred as armature bar rotary machine, a cam wheel as described above is attached to the armature bar which is then attached to the needle bar. The cam wheel makes the armature bar move up and down. In this design, the up and down motion is believed to be more accurate as the armature bar is held in place by the frame of the machine. This also gives oscillating needle more stability which helps for accurate placement of injectable composition. In another variation of this design, the needle bar is attached to the slider mechanism, which is held in place by a channel. The electric motor shaft is attached to the slider mechanism. In the swash drive rotary tattoo machine, a swash plate is used to convert up and down motion instead of cam wheel.

One illustrative device for delivering injectable compositions using oscillating device is shown in FIG. 20. FIG. 20 denotes an alternate injection device, which is a standard rotary tattoo machine modified/adopted so that it can be used in this invention. The adopted machine comprises an oscillating needle (syringe needle) 2101 which is connected to a syringe via flow control vale 2110, a 1 ml disposable syringe (functioning as an injectable composition reservoir) 2102, a screw that can help to immobilize the syringe 2103 which is loose enough to permit oscillations to the syringe, an opening 2104 in the syringe from where injectable liquid can be added in the syringe, a metal wire 2015 with a circular hook similar to standard tattoo needle that connects to the oscillating bar 2106 of the rotary tattoo machine. 2107 is screw that controls oscillation length (feature of the machine). 2108 is an electric motor and swash mechanism housing that oscillates the syringe needle and 2018 denotes 12 V electrical supply contacts for the electric motor inside the housing. 2101, 2110, 2102 and 2105 may be provided as a one unit assembly (oscillating needle with injection reservoir similar to described in FIGS. 18A through 18C). The sterile one unit assembly with prefilled injectable composition can be attached to the oscillating device and used for injecting the composition as described in this invention.

III. Non Oscillating Needle Device Apparatus

This invention uses oscillating needle devise as a preferred method to deposit injectable compositions. Oscillating devise should not be considered as a limitation for this invention. In some situations, a non-oscillating device can also be used. As long as the device injects, tiny droplets, preferably 1.0E-02 to 1.0E-16 mL injectable composition per needle per injection. In one illustrative example, a multi-needle injection device (non-oscillating comprising 2-10000 or more needles per devise) capable of injecting 1.0E-02 to 1.0E-16 ml per needle may be used to deposit polymer solutions comprising drug for sustained drug delivery. The deposited tiny droplets can further undergo transformation from liquid to solid/gel via crosslinking/chemical reaction, precipitation, thermoreversible gelation and the like.

FIGS. 16A-16C illustrate the deposition patterns that can be generated by such device. If the device has 10-10000 needles per device, 10-10000 microparticles may be formed in situ per injection. Thus it is possible to possible to deposit precise number of particles formed in situ. In one embodiment, a PLGA solution is injected in situ to form microparticles in situ. 100-10000 particles may be formed in situ for sustained drug delivery using such non-oscillating device. The injected particles may be deposited in a two or three-dimensional pattern as illustrated in FIG. 16B and FIG. 16C. Additional patterns of deposition could also be made and may include but not limited to conical, platonic solids shape, torus shape, pyramid shape, irregular shape and the like and are considered as part of the invention. A preferred pattern provides a sustained release of drug in the affected local disease site.

In order to control the precise deposition in the tissue, mechanical or computer controlled devices can be designed and used. Needle of such devices will, for example, oscillate at 60 times per minute but will move or change its location of next injection/deposition to 1-1000 microns along x, y or z direction in the body or tissue to change the area of deposition. Thus each injection will occur at different point in the tissue and each droplet is deposited 1-1000 microns apart from each other. The 1-1000 micron value used herein is for example only and may vary higher or lower depending on each clinical location or desired outcome such microparticle formation or film/implant formation. Each deposited droplet can provide sustained drug delivery in the deposited area. A computer controlled machine-assisted deposition can be more precise if used properly.

The computer controlled deposition apparatus is especially useful for treatment of treatment of cancerous tumors. In general, a precise three dimensional map of the tumor can be obtained by medical imaging technique such as CAT scan or MRI machine. The coordinates of the tumor map can then be used to determine the various locations inside the tumor for injection of cancer drug containing injectable composition. As an example, each injection location can be 0.01 to 2 mm part from each other and each location can receive 1.0E-02 to 1.0E-16 ml of injectable composition. An injectable device can be then programmed to access the predetermined injection location and is then used to deposit the required amount of injectable composition at each predetermined point inside the tumor. If desired x-ray contrast or MRI contrast agents may be added in the composition to visualize and record the injected composition.

IV. Injectable Compositions

The preferred injectable compositions contain an imaging or a visualization agent wherein the composition of the agent is colored or fluorescent in nature. The depth of penetration is close to the surface and preferred depth of deposition is closer to the tissue surface. Preferred color of the injected composition is green, black, blue, yellow, brown, which show better contrast to the surgical environment or human flesh. Combination of primary colors (red, green and blue) in any proportion may also be used. Multiple depositions (preferable different colors) may be used to release therapeutic drugs. For example an antibiotic and wound healing enhancing growth factors may be deposited around a wound. Each deposition may represent a different color. Each deposition may have its own sustained release rate.

Alternate embodiments may comprise of injectable compositions which do not include the visualization agent. For example, in treatment of cornea tissue, which is transparent in nature, the preferred injectable composition may have similar refractive index as cornea and is not intentionally made colored.

The injectable compositions in accordance with the present invention are categorized as:
  (a) those which comprise of drug bearing compositions, preferably microparticles that are synthesized externally and injected in the tissue
  (b) those which are capable of synthesizing microparticles in situ in the tissue Both the categories of compositions may comprise of combinations of one or more drugs, one or more visualization agents, one or more carrier medium, one or more additives for therapeutic, cosmetic or analgesic effect, and macromolecules which may be biostable or biodegradable in nature. Further, both these categories of compositions may undergo either physical changes or chemical changes or a combination of both, once they have been injected inside the tissue layer for sustained delivery of specific constituents.

V. Method of Delivery of Microencapsulated, Colored Microparticles Using Oscillating Needle Delivery Device An embodiment of the invention as described in FIGS. 3A through 3D, shows a partial schematic representation of a method for local delivery of injectable composition comprising; biodegradable/drug microparticles and a biocompatible carrier fluid such as PBS buffer solution (pH 7.2), at a local site inside the human/animal body such as dermis layer of the skin tissue. The injectable composition is loaded inside the injection device capable of injecting the composition at 10 to 12000 injections per minute. During each injection the device can deliver 1.0E-02 to 1.0E-16 ml of injectable composition. After injecting the composition, the fluid in the composition is dissipated by the surrounding tissue leaving behind the microparticles entrapped in the tissue, which deliver the drug in a sustained manner.

FIG. 3A shows a partial schematic representation of the injection device wherein the 301 schematically represents an oscillation apparatus that is used to oscillate the injection needle 305. As an example, the 301 could be magnetic coils and other parts of the tattoo machine. The 302 represent an injectable composition reservoir, which is connected to the temporary reservoir 304 via a control valve 303, which controls the flow of injectable composition to the needle. The oscillating needle delivers the composition from the 304 in the skin tissue. An epidermis layer 306 and dermis layers 307 along with the injected composition droplets 308 are schematically shown in FIG. 3B. The fluid in the injected droplets is dissipated in the surrounding tissue leaving behind the microparticles 309 in the tissue, which release the drug at the injection site in a sustained manner. The imaging agent in the injectable composition or contained in the microparticles helps to visualize the injected composition during the infusion or tattooing process as well as after the process. Medical imaging techniques like x-ray imaging, MRI imaging and the like may also be used to see the infused composition. In some cases, addition of medical imaging components such as radioopaque agents, may be necessary if used in procedures such as catheter based delivery techniques.

Colored compositions help to be detected by the human eye and may help to control the precise dose of the drug to the tissue. For example, 1 cm deposition line or tattoo line on the skin tissue may represent an equivalent to 10 microgram of a therapeutic drug (1 microgram drug per mm of the tattoo line). By controlling the length/area of line drawn/injected area, a total dose of a drug for a given clinical condition can be determined and infused. If a total dose of 40 microgram is deemed necessary, then 4 cm length of tattoo line could be drawn/infused (assuming 10 mg of drug per cm of deposition/tattoo line). The 4 cm length could be drawn/tattooed in any shape such as circumference of a circle or perimeter of a rectangle and the like. It could also be an artistic figure such as an outline if smiley face or bird and the like Thus, it is possible to visually control the dose of a therapeutic drug using this inventive method. This is especially useful when delivering the drug using minimally invasive surgical techniques (MIS techniques). A fluorescent composition is even more useful as small amount of coloring composition is needed to provide a bright fluorescence. In another embodiment, an injection counter sensor is attached to the device. Knowing total number of injections and injection volume per injection can help to determine precise amount of composition/drug delivered in the body or tissue. In preferred methods, the microparticulate compositions are delivered in a discrete way, preferably 1.0E-02 to 1.0E-16 ml of injectable composition is delivered per injection. In one exemplary embodiment, an oscillating or pulsating needle is used to deliver precise dose of a drug delivery compositions in the bioprosthesis surface or in the live tissue surface wherein drugs or drug delivery compositions are deposited under the tissue surface such as in the dermis layer of human skin. After the delivery, the particles remain entrapped in tissue fibers for controlled/sustained drug delivery. It is preferred that the drugs and particles and the carrier used are biodegradable. The needle can oscillate (moves in and out of the tissue surface) from few injections per minute to 2000 injections per second, preferably 50 to 200 times per second. The oscillating needle injects the drug delivery composition in a non-continuous or discrete way. With each penetration, there is a small of amount of time gap wherein no drug is delivered (non-continuous). In the preferred embodiment, the tattoo machines or similar machines could be used in delivering microencapsulated drug compositions. Use of tattoo machine is for illustration only and other specialized devices that offer control over needle oscillation frequency, control over composition reservoir, control over flow of reservoir composition to the injection needle, temperature control of the reservoir and needle, control over needle penetration depth (oscillation) and the like could be designed and used. In one exemplary embodiment, 1 g of rifampin-loaded microspheres or other drug-loaded colored microspheres (particle size below 300 microns) are suspended 2-10 ml 30 percent glycerine solution. Preferably the mixing is done just prior to injection. A commerically available tattoo machine with oscillating needle is used. The machine is set up according to instructions provided by the manufacturer. The machine is attached with #12 size needle. The machine is turned on and the voltage of the power supply for the oscillating coils is set between 8.0 and 9.0 volt (at this voltage, it is believed that the needle oscillates between 50-200 times per second). 4 inch by 4 inch 1-2 mm thick bovine pericardium (unfixed tissue) is placed on a flat surface on top of a rubber pad for support. A small amount of lubricant grease (for reducing needle frication) is applied on the 2 cm by 2 cm area at the center of the tissue. The tattoo machine needle is dipped in the drug suspension and foot paddle of the machine is pressed to supply the composition to the machine. The oscillating needle is kept about 0.1 to 2 mm distance from the tissue surface. The oscillating needle is slowly moved to draw 1 cm diameter circle on lubricated side on the tissue. The needle penetration is adjusted in such a way that the drug particles are deposited at about 10 to 1000 micron dip inside the tissue surface and can be visually seen. The needle is dipped in the rifampin suspension several times to resupply the drug for infusion. It is possible to supply the suspension continuously by modifying the apparatus. As the needle moves up and down the tissue surface (reciprocating oscillations), a red line is seen on the tissue surface (drug loaded particles has mild red color and pericardium is white in color). The color helps to visually control the deposition of particles in the tissue. After the circle is drawn, the excess drug suspension is wiped out from the tissue surface. The infused particles are visible and cannot be wiped away indicating they are locked inside layers of tissue. Infused surface is washed with PBS. The infused particles cannot be removed by wiping or washing indicating that they are embedded in the tissue. The drug released from the embedded particles may be monitored in vitro. This invention is not limited to how the oscillating action is obtained. The size of the particles that can is delivered using oscillating needle may be formulated from 0.03 microns to 1000 microns range, which enables them to be delivered using tattoo machine needles. Generally standard tattoo machine needles come in variety of sizes, and range from #12 (diameter 0.35 mm) to #6 (diameter 0.20 mm) size. The drug particle size must be smaller than the needle diameter that is used for injection. Two, three, four, five or several needles may be fused together to obtain a variety of delivery/tattoo patterns. The commerically available tattoo needles can generally handle particles size below 350 microns. For other sizes, needles can be custom designed, built/fabricated and used. The drug particles to be infused must be formulated so that they can be delivered using tattoo machine oscillating needle apparatus. In general, the size of microparticle must be 80-90 percent or less than the internal diameter of the oscillating needle being used. This ensures smooth passage of microparticles via needle to the tissue. The preferred microparticles use color to visually detect the loading/dose of the drug being delivered. Some preferred compositions for obtaining colored microparticles are given in Table 2.

TABLE 2

COLORED MICROPARTICLES WITH DRUGS

| COMPOSITION CODE | COMPOSITION |
|---|---|
| A | Microparticles with color only. For example PLGA particles encapsulated with F D and C colors or coated with colored composition or stained with coloring stain. |
| B | Microparticles with therapeutic drug only. For example PLGA particles encapsulated with drug gentamycin. |
| C | Microparticles with color and therapeutic drug in the same particle. Color and drug exist separately in the same particle. For example PLGA particles encapsulated with drug gentamycin and F and D C blue color wherein gentamycin and F D and C blue color are in the same particle. |
| D | Microparticles with colored therapeutic. The drug itself has color. For example rifampin has mild red/yellowish color and is encapsulated in the microparticles. |
| E | Drug particles stained with color. No microencapsulation needed. Poorly water-soluble drug particles such as chlorhexidine acetate drug particles can be stained with biocompatible stains. |
| F | Compositions with code A and B can be combined to obtained a colored microparticle composition. They can be mixed in any proportion to obtain desired drug loading and color intensity. |

The preferred injectable device can inject the injectable compositions at various depths in the tissue or body. This can be achieved by controlling the depth of penetration of (controlling the oscillation length) which can be controlled by various ways (mechanical, pressure, electrical pulse and the like). Preferably the injectable device has a feature, which can enable the user to "dial in" or "tune in" the depth of needle penetration for a given clinical situation. For example, the needle can be dialed in for depth of 2 mm initially. Upon injection and deposition, the needle is then set to dial in for 1.5 mm penetration and the pattern can be repeated at 0.5 mm distance until tissue surface is reached. The desired depth of penetration can vary depending on clinical application. The deposited materials can form various two and three dimensional shapes or patterns. FIGS. 16A through 16C show partial schematic representation of deposition of injectable compositions at various depths in the tissue and in various two or three dimensional shapes and patterns. FIG. 16A shows tip of an injectable needle 1602 of an oscillating needle device penetrating at various depths (D1, D2 and D3 for example). 1601 represents an imaginary tissue surface at zero depth of penetration (D0). The needle 1602 of an oscillating needle device can be tuned or "dialed in" to penetrate at predefined tissue depths (D1, D2 and D3). FIG. 16B shows a deposition pattern of a eleven needle injectable device whose needles are arranged in a circular shape and can be dialed in to deposit at various depths. Upon deposition at various depths (D1, D2 and D3 as an example), a cylindrical pattern of deposited material is formed. The injected compositions 1603 in the shape of a hollow cylinder will release the drug at a local site in the body in a sustained manner. FIG. 16C shows deposition pattern of an injectable composition 1604 injected in a tissue in cubical pattern. A twenty four needle injectable device whose needles are arranged in a rectangular fashion (as shown in FIG. 16C) and is capable of injecting at various depths. Upon deposition at various depths, a cubical pattern of deposited materials is formed which can provide local drug delivery in the deposited area. Alternatively a separate multi-needle injectable device can be used for each deposition depth. For example one illustrative device with 100 micro needles that can only penetrate at a depth of 2 mm is used to deposit at a depth of 2 mm. Other similar device that can penetrate at a depth of 1 mm and is used to deposit at a depth of 1 mm and the like. Thus compositions can be delivered using multiple devices at various depths using different devices designed to deliver at certain specific depth. It is understood that many changes in shapes and patterns of deposition can be made and these include cylindrical, cubical, triangular, pentagonal, hexagonal heptagonal, irregular and the like. The preferred device has two, three, four, upto 10000 or more needles per device and preferably the needle is capable of changing the depth of penetration. The needles used may have two or more lumens. The depth of penetration may range from 10 microns to 15 mm preferably 300 microns to 5 mm. Each needle in a multi-needle device may be separated by 5 microns to 10 mm, preferably 50 mm to 5 mm. The injected materials and various patterns are especially useful for treatment of cancerous tissue for local drug delivery. Since cancerous tissue/tumor has various shapes and sizes, the inventive device and methods of drug delivery will be able to cover majority of tumor body for local drug delivery. Thus it is to be noted that depending on the desired pattern of local drug delivery, the oscillating needle device is provided with desired number of lumens.

It is preferred that drug particles are encapsulated in a microparticle, preferably in biodegradable microparticles or microspheres. Many methods are known in the art to make biodegradable particles. Example 4 teaches some preferred embodiments in obtaining drug-encapsulated microparticles. As mentioned in Table 2, colored microparticles can be obtained in many ways. Some preferred methods are given in Table 2. One embodiment teaches to encapsulate F D and C dye and drug in a same microparticle. Another embodiment teaches making colored and drug coated microparticles separately and using the mixture of these two particles in any proportion to obtain suitable drug loading and color depth. Drug and color compound loading in particles is controlled to obtain a suitable drug release or color depth. The drug/color compound loading in the biodegradable polymer used for encapsulation may range form 1 to 50 percent relative to the weight of polymer, preferably from 5 to 30 percent. Colored microparticles may also be obtained by staining the biodegradable polymer particle or may be obtained by encapsulating within the polymer. In one case the drug (rifampin) itself has a mild red/yellow color and serves as drug as well as coloring agent. In another embodiment, the drug particles are stained with staining compound and used without encapsulating in the polymeric carrier. Poorly water soluble drugs such as chlorhexidine, paclitaxel, silver chloride and the like which have water solubility less than 5 g/100 g water are especially useful for this application. The drug particles or colored drug particles are suspended in a fluid so that they can be delivered using the oscillating needle apparatus such as tattoo machine apparatus. The Tattoo ink with drugs, preferably drugs encapsulated in microparticles/microspheres and even more preferably with biodegradable polymer microspheres can be useful for local drug delivery applications. The definition of biodegradable polymer is included in the definition section. The preferred biodegradable polymers used for encapsulation of drug are: polyhydroxy acids, polyester, polylactones, PEG, polytrimethylene carbonate or their copolymers or blends. Hydrogels, biostable or biodegradable, could also be used as drug delivery vehicles. Some preferred embodiments provide methods and compositions for preparing hydrogel based drug delivery compositions. The local delivery of the drugs preferably under the skin or during a surgical procedure can be useful for treating variety of diseases. The drug particles must be properly formulated to enable them to be delivered using oscillating needle or tattoo machine apparatus. The drug particles must be suspended in the liquid medium such as PBS (pH 7.2). Other aqueous solutions include saline solution; water alcohol, water glycerine mixtures and the like may also be used. Water with biocompatible buffers is a preferred medium. Additives may be added to the particle formulations may be include but not limited to: wetting agent to remove air from particle surface; dispersing agent or surfactant to form a stable suspension; and a liquid medium that maintains the particles in a fluid form. An additive that improves the loading of drug suspension in the needle may also be used. The glycerine, isopropanol, propylene glycol, water and their mixtures in any proportion and the like may be used. In some situation the drug particles may be stirred using mechanical, magnetic or other types of stirring actions to keep them in suspension. The microspheres or microparticles used may be single walled or double walled or multi-walled. The microspheres or microparticles used may be hollow or solid in nature. The microspheres may have additives such as antioxidants; surface coating agents; plasticizer and the like. The microparticles used may be porous, partially porous or completely non-porous/solid in nature.

In another illustrative embodiment the tattoo making machine and its oscillating needle can be used to infuse drug particles at a local site during a surgical or MIS surgical procedure. For example if a local antibiotic needs to be delivered in a controlled manner at a surgical incision site (in situ delivery), the tissue in the surrounding the area may be "tattooed" or infused with drug particles or drug containing liquid droplets. Similarly localized tattooing can be used to manage pain by delivering a pain reliving medication via infusion of drug particles (tattooing with particles that have pain medication) under the dermis. The type of drug used will depend on the medical condition being treated. The list of drugs is clearly defined in the definition section including additional list drugs cited in the reference may be used. The list of drugs is not limited to drugs mentioned in the definition sections. Other drugs compounds cited in U.S. Pat. No. 8,067,031 cold also be used, cited herein for reference only. It is preferred that injectable compositions have a visualization agent such as D and C or FD and C dye that is safe to use under the body or dermis and is preferably biodegradable. It is also preferred that the particles injected are biodegradable. It is understood that the amount of drug and type of drug infused will depend on the clinical need. In one exemplary embodiment, a tattoo ink particles (titanium dioxide as a model particle) are first coated/incubated using drugs/bioactive compounds and then the tattooed/embedded in the skin surface of the subject. The titanium dioxide particles surface can be coated with protein like drugs by simply adsorbing the protein in its surface (incubating with 1 to 10 percent insulin or albumin solution in PBS pH 7.2 for 2 to 24 hours and adsorbing insulin/albumin on particle surface is one illustrative example). The white color of titanium dioxide acts a visualization indicator. Other types of coatings such as PEG-polylactone or polylactones along with drugs may also be used to coat the tattoo ink particles. Inorganic or organic solids/salts that have low water solubility are biocompatible and biodegradable may also especially useful as a carrier of drugs. The coated tattoo particles release the drug under the dermis. Variety of dyes and pigments can be used as a carrier for drug particles these include but not limited to titanium oxide, carbon black, azo dyes, acridine dyes, quinoline and phthalocyanin, iron oxide and the like. Certain metal alloys such as magnesium metal alloys are known to be biodegradable and can be formed into microparticles or microspheres and used as a carrier for drugs. Certain inorganic glass biodegradable materials are known in the art such materials also can be formed into microparticles and used as a carrier for drugs. The low water soluble drug such as chlorhexidine as mentioned earlier may be first stained with coloring dye to make them colored and then implanted under the skin. For example the chlorhexidine gluconate particles may be suspended in one percent Eosin Y or turmeric staining solution in water to impart red color or yellow color to the particles. Those skilled in the art will understand that many types of coloring agents can be used. Coloring agents with primary colors or black, blue, red, yellow and green colors or combinations thereof are preferred due to their easy detection with by the human eye. Among these, particles that interfere with MRI imaging or other medical imaging techniques are least preferred. Certain tattoo inks have paramagnetic impurities or have paramagnetic properties and cause adverse effects while MRI imaging and therefore are least preferred. The color of tattoo ink particle serves as visual clue, which helps visually to control the amount of drug delivered as well as targeting the location of the drug delivery. If the delivery of drug is done using tattoo ink and under the dermis, then using tattoo removal methods such laser ablation, the tattoo/drug particles can be used to remove the tattoos and this may be useful if the drug has adverse reaction to the patient and implants needed to be removed. The particles used herein could also be liposomes, emulsified drug particles and the like.

Biodegradable microspheres can be fabricated using variety of methods and can be formulated to release drugs at a certain rate (kinetics of drug release). The drug release may be by achieved by diffusion and/or biodegradation mechanism or combination of both. The preferred rate of release is a zero order release where a constant or nearly constant rate of drug release over a long period of time is obtained. Polymer molecular weight, type of polymer used, microparticle size and shape, double or single walled particle, drug loading in the microparticle, porosity of the particles are some of the variables that can be used to obtain desired rate of release for a given therapeutic or bioactive compound. If needed, combination or two or more microparticles may be used to obtain burst release and/or zero order release of drugs. Please refer to U.S. Pat. No. 6,599,627 and cited art and cross references therein to make biodegradable microspheres, cited herein for reference only.

Example 1A and 1B teach methods to obtain biostable tissues for bioprosthesis applications. Two preferred methods for obtaining biostable tissues are given. Other methods known in the art may also be used to obtain biostable tissues for bioprosthesis application.

Example 2 teaches many embodiments for obtaining biodegradable tissues suitable for many biodegradable bioprosthesis applications. The methods used include use of uncrosslinked tissue, tissue that has been decellularized, tissues that are crosslinked with carbodiimide or tissues that has been crosslinked using biodegradable crosslinkers. Other methods to obtain biodegradable tissue may also be used, but preferred embodiments are given in Example 2A-2D.

Example 3 provided illustrative embodiments for obtaining colored biodegradable particles. In one embodiment, a colored and radio-opaque microparticle is obtained from PLGA biodegradable polymers. The colored, radio-opaque compounds are mixed in solvent, the solvent is removed and the cast polymer is ground to obtain colored and radio-opaque particles. In another embodiment, commerically available biodegradable sutures are purchased, cryogenically ground, sieved and a fraction suitable for injectable formulation (size less than 300 microns) is used for the application. A commercially available degradable catgut suture is also ground in a similar way and used. A spray drying method is used to prepare colored microspheres using PLGA. One embodiment teaches staining methods to induce color to the commercially available PLGA materials. The particles are colored by staining with variety of stains available for biomedical use. Alternatively many commercial companies/entities provide biodegradable microspheres for a given clinical application, such companies may be contracted to provide a encapsulated microparticle compositions. Companies like OctoPlus N.V. Netherlands, Nanomi B.V, Netherlands; Polysciences, Inc. Warrington Pa., Alkermes plc Waltham Mass., Ramannco Inc., and the like could be used to make custom based sustained release microparticle compositions, preferably biodegradable microspheres for a given application.

There may be other methods known in the art to make biodegradable microspheres, such methods could be used or methods yet to be developed could also be used. By mixing two or more colored particles, preferably primary color particles, a desired color shade may be created. Many types of biodegradable polymers could be used to make color particles. The list is exhaustive but preferred polymer include polymer, copolymers of polylactones or polyhydroxyacids, and polytrimethylene carbonate. PEG-polylactone PEG-polycarbonate polymers are also preferred. Among hydrogel polymers, the PEG based crosslinked hydrogels and protein based hydrogels are preferred carriers for colored substances. In some applications hydrogels may be preferred because hydrogels in dry state can form a very small size particles and once injected can absorb upto 0.1 to 20 times to its original weight water which increases their size and therefor are unlikely move away from injection site. Hydrogels that absorb 10 to 10000 percent water upon injection are most preferred. Some embodiments in this example illustrate methods to obtain hydrogel microspheres. Such microspheres may be dried or dehydrated and used. PEG based hydrogels are prepared by crosslinking PEG based macromonomers or crosslinking reactive precursors. Methods of preparing biodegradable hydrogels are known in the art (please refer to U.S. Pat. Nos. 5,410,016 and 6,566,406 and references cited therein, cited herein for reference only) may also be used. Methods described in the cited patents can be used be to obtain biodegradable hydrogels with different amount of in vivo degradation time. Methods described in these patents could also be adopted to make hydrogels microspheres. Methods provided in U.S. Pat. No. 6,599,627 and cited art and cross references therein, cited herein for reference only may also be used to make colored biodegradable microspheres.

Example 4 teaches several illustrative methods to make drug encapsulated microparticles. One method teaches the use of solvent evaporation technique to create drug-loaded microspheres. Another method uses emulsion method to make drug encapsulated microspheres. Methods such as spray drying method, frees-drying method, melt method can also be used. Artisans can understand that many modifications can be done to these methods to obtain drug loaded microparticles, preferably microspheres that have desired size and drug loading. In addition, compounds such as coloring agent may be added during particle preparation to obtain a drug loaded microparticle with color. Example 5-6 teaches one illustrative method for obtaining colored and drug encapsulated composition in the same particle. Microparticles with drugs and microparticles with coloring agent can be mixed together to obtain a desirable color as well as release profile. The mixing can be done in any proportion to obtain desirable color and drug loading. Two or more colored particles may be mixed to obtain a desirable color shade. One embodiment teaches the preparation colored hydrogel based composition. In some application, it is preferred that the color and drug is encapsulated in a same microparticle. Preferably drug is encapsulated for sustained drug release and the particle is coated/stained with a coloring composition to make it colored.

VI. Method for Delivery of Polymer Solutions Using Oscillating Needle Delivery Device for In Situ Formation of Biodegradable Microparticles This invention also discloses in situ formation of biodegradable microparticles or microspheres at the implantation site or in the bioprosthesis tissue. This embodiment is disclosed in FIGS. 4A through 4C. The solvent in the injected droplets is dissipated or dissolved in the surrounding tissue leaving behind or precipitating the polymer with entrapped drug or imaging agents 403. Preferred polymers used are water insoluble or substantially insoluble. The polymer particles 403 release the drug at the injection site in a sustained manner. The particle is removed by biodegradation process in few hours to several months depending on the polymer used. In one illustrative embodiment, PLGA, polylactide-co-glycolide) (lactide:glycolide (50:50), molecular weight 30000 to 60000 g/mole an exemplary synthetic biodegradable polymer that is water insoluble is used as a carrier for the drugs. The polymer is dissolved in dimethyl sulfoxide, an illustrative biocompatible water miscible solvent along with Gentamycin or rifampin or coumarin 6 as fluorescent as exemplary therapeutic drug and ethyl eosin or methylene blue as a colorant. The polymer solution at 10 percent drug loading (relative to polymer weight) is sterile filtered using an inert syringe filter. The filtered sterile solution is injected in the skin tissue or in the bioprosthetic tissue using a tattoo machine as oscillating needle machine device. Briefly, a lubricant is applied and the oscillating needle is filled with the sterile polymer solution along with drug and colorant and the skin or prosthetic tissue is tattooed or infused with the polymer solution. The live skin has physiological fluids (free water in the tissue), which extracts water soluble solvent (DMSO) from the injected solution thereby precipitating the water insoluble polymer. The PLGA polymer is insoluble in water. The removal of water from the infused liquid droplets form PLGA microparticles in situ. The drug and colorant remain entrapped in the polymer particle. The polymer undergoes biodegradation process and release the drug as result of diffusion and/or biodegradation process. The polymer is completely digested by the tissue after a certain period of implantation. Thus a temporary therapeutic tattoo is created by the infusion of polymer solution. FIG. 21A (2301) shows an illustrative biodegradable polymer (PLGA) dissolved in DMSO solvent and comprising rifampin as an exemplary drug is injected using an oscillating needle in the chicken leg muscle. The implanted composition has faint red color of antibiotic rifampin and has a shape of a circular ring and solid square and is embedded in the surface layer of the muscle. The infused composition is embedded in the tissue and cannot be removed with saline wash and mechanical peeling. In another embodiment, 30 percent drug loading is used instead of 10 percent. Yet in another embodiment, polycaprolactone (PCL) is used as a biodegradable polymer. This polymer degrades at a slower than PLGA polymer and generally degrades in few months to few years. In another embodiment, several PEG-polylactone copolymers are synthesized and used for sustained drug delivery and formation of microparticles in situ inside the tissue. The incorporation of PEG inside the polymers is generally known to improve the biocompatibility of the polymer. The PEG in the copolymer may also provide solubility in alcohol based solution or in water depending on the PEG molecular weight used and amount of polylactone copolymer in the copolymer. In one illustrative embodiment, a Pluronic copolymer is used to initiate the polymerization of dl lactide and the PEO-PPO-PEO-polylactate copolymer is dissolved in n-methylpyrrolidinone and used for delivery using oscillating needle. In another embodiment, a PEG based copolymer, PEG-polylactate-10 that dissolves in water is used for tattooing and drug delivery. The polymer forms micelles in water and thus the emulsion in water (nano size particles in water) can dissolve/emulsify hydrophobic small molecular weighted drugs and can release the drug in a sustained manner. Some compositions, especially PEG or Pluronic based polymers or copolymer may undergo swelling (absorption of water) after the solvent has been extracted. The amount of water absorption will depend upon the amount of PEG or Pluronic in the copolymer. In general, as percentage of PEG in the copolymer is increased, the copolymer will absorb more water. The amount of water absorbed by in situ formed particle may range from 0.1 percent upto 10000 percent, generally 0.5 to 200 percent, depending on hydrophilic nature of the polymer used.

Several biodegradable polymers are known in the art and can be used for sustained delivery. A partial list of preferred biodegradable polymers is provided in the definition section. The preferred polymers are synthetic biodegradable polymers which include, but are not limited to, polymers, dendramers, copolymers or oligomers of glycolide, dl-lactide, d-lactide, l-lactide, caprolactone, dioxanone and trimethylene carbonate; degradable polyurethanes; polyamides; polyesters; polypeptides; polyhydroxyacids; polylactic acid; polyglycolic acid; polyanhydrides; and polylactones; polyethylene glycol-polyhydroxy acid or polyethylene glycol-polylactone copolymers (PEG-PL copolymers); polyvinyl alcohol co-polylactone copolymers are among the hydrophilic synthetic polymers could also be used. These polymers can be dissolved in biocompatible organic solvents. Each polymer used can have its own set of organic and water based solvents. List of solvents that can be used for a given polymer can be found in Polymer Handbook. In general, water miscible solvents are most preferred. Among these solvent that can be tolerated by live tissue are mostly preferred. The partial list of solvents that can be used include but not limited to: dimethyl sulfoxide, n-methylpyrrolidinone, acetone, acetic acid, ethanol, isopropanol, glycerol, ethyl acetate, polyethylene glycol (low molecular weight), 1,3 propane diol, 1,4 butane diol, 1-6-hexane diol, tetrahydrofurane, triethanol amine, water, buffered water solutions with pH ranging from 6 to 8, preferably pH around 7 and their mixture in any proportions and the like. If water based solutions are used, it is preferred that the solutions are osmotically balanced. Among these, ethanol, dimethyl sulfoxide, water and n-methyl pyrrolidine and their mixtures in any proportion are most preferred. The polymers concentration in the solvent may range from 0.1 to 60 percent depending the molecular weight of the polymer, the structure of the polymer and the solvent used. In general, polymer-solvent systems that provide low viscosity solutions are preferred. High viscosity solution are difficult inject and therefore may be less preferred. The list of drugs that can be used is given in definition section of this document. The drug may be dissolved, suspended or emulsified before injecting. The drug polymer mixture should be able to be delivered by oscillating needle device or other injectable device. The concentration of the drug in the polymer (relative to polymer weight) may range from 0.1 percent 50 percent, preferably 1 to 40 percent and most preferably 10 to 30 percent. The drug may be dissolved or dispersed or emulsified in the polymer solution. If drug is insoluble in the polymer solvent system, fine particulates (particle size 0.1 microns to 500 microns) may be used. The particle size chosen should be less than the needle size of the injecting device. The polymer may be added a medical imaging agent or colorant to help the delivery/deposition process. The colorant may be dissolved or suspended in the polymer solution, preferably dissolved in the polymer solution. Many biocompatible colorants can be used and these include but not limited to: many FD and C dyes or D and C dyes that FDA has permitted to be used in approved medical devices. Colorants that have been used in absorbable surgical sutures or contact lens materials are most preferred. Partial list of coloring agents or coloring compositions is given in the definition section of this document. The size of the precipitated polymer inside the tissue may range from 0.1 microns to 1 mm, preferably 1 micron to 900 microns, even more preferably 10 to 800 microns. The preferred shape of the injected particle that is formed after removal/dissipation of solvent by the tissue include but not limited: spherical, semispherical, elliptical, circular disk, or irregular shaped. The in vivo biodegradation time for the polymer may be from few hours to few years, preferably few days to 6 months. The deposited particle may release the drug in a sustained manner. The delivery of the drug may last for few hours to several months, preferably 3 days to 120 days. The release rate of the drug may follow zero order rate release (constant release over a period of time) or may follow standard diffusion model or combination of both. The drug may be released via diffusion and/or erosion mechanism of the carrier.

In some embodiments, some or all deposited droplets are placed at new injection site. There could be a separation of 5 microns or more preferably 10-2000 microns between each deposited composition. The separation of each injected fluid deposition can prevent fusion/agglomeration or coalescing of neighboring droplets. The injected polymer solutions, melts, thermoreversible compositions, may be separated during deposition process. The reduction in agglomeration can potentially help to attain uniform size deposited microparticles. A separate discussion of preventing droplet fusion is done separately in another section.

VII. Neat Liquid Based Delivery Systems Delivered Using Oscillating Needle Device for Delivery of Drugs Via Biocompatible Liquid Droplets Formed In Situ.

This invention discloses novel compositions wherein a polymeric or non-polymer liquid carrier is used for sustained release of drugs. FIGS. 5A through 5C show a partial schematic representation of a method for local delivery of injectable composition comprising; polymeric or non-polymeric liquid carrier and drug or imaging agent, at a local site inside the human or animal body such as dermis layer of the skin tissue.

In some embodiments, tattoo machine with oscillating needle and its delivery methods (delivery of particles via oscillating needle) may be used to deliver liquid droplets as a drug delivery carrier along with drugs. The fluid carrier may be oil or other polymeric or non-polymeric liquids. The carrier liquid may be water soluble or water insoluble. The liquid carrier is substantially liquid at room temperature or around body temperature. Biocompatible liquid carriers may be hydrophobic or hydrophilic. The liquid can be oils such as sucrose acetate isobutyrate, vitamin E and its derivatives; fatty acids like oleic acids and its derivatives; fatty alcohols; liquid non-ionic surfactants like polysorbate, Tween® 40 or Tween® 80; polymers like liquid polylactones, liquid polyhydroxyacids, liquid PEG-polylactone copolymers, PEO-PPO-polylactone copolymers, polytrimethylene carbonate, liquid polyorthocarbonates, and its copolymers or combinations thereof and the like are preferred. Biodegradable liquids are most preferred. The liquid carriers along with drugs (either dissolved or suspended or emulsified) are delivered under the skin in the dermis or at a surgical site for a local therapeutic effect using oscillating needles similar to the used in tattoo machines. The liquid carriers may also be infused in bioprosthesis tissue surface using the same methods as above. The biodegradable liquids/microparticles used in this invention may last in the body from 3 hours to few years, preferably from 24 hours to 360 days, even more preferably from 24 h to 90 days. The drug loading in liquid carriers may range from 0.01 percent to 50 percent, most preferably 0.1 percent to 40 percent, even more preferably from 1 to 30 percent. In one illustrative embodiment, vitamin E acetate is used a biocompatible liquid carrier and rifampin as a model drug. The mild color of rifampin is used as a visual aid to deposit the liquid in a tissue using an oscillating needle device such as tattoo machine. The oscillating needle of a tattoo machine is filled with the liquid carrier and applied on the tissue surface. The needle penetrates the surface, deposits the liquid underneath the tissue and pulls out. The pulling out action dislodges the liquid droplet from the needle and is therefor stays backs at the injection site. The liquid droplet delivers the drug in a sustained manner. In one embodiment, a herbal therapeutic like turmeric is loaded in a vitamin E (loading 1-10 percent concentration) and deposited under the facial skin as treatment for dry skin condition and/or acne treatment. Since turmeric has antimicrobial properties, the deposition can be useful for acne treatment. The turmeric composition is deposited around the acne pimples to have a therapeutic effect. Other drugs suitable for acne treatment may also be used and deposited using methods described in this invention. Ingredients that provide facial cosmetic benefits may also be deposited using the methods and compositions described in this invention.

In another embodiment, non-polymeric liquid sucrose acetate isobutyrate is used as a liquid carrier. In some cases, viscosity-modifying agents such as biocompatible organic solvents like ethanol, DMSO and the like may be added in any proportion (generally 1 to 99 percent, preferably 5-90 percent) to adjust the viscosity of the non-polymeric liquid carrier like sucrose acetate isobutyrate. The lower or higher viscosity can help the liquid carrier injectable from the chosen injectable devise. Other additives such as antioxidants, UV stabilizers, generally found in pharmaceutical preparations may also be added.

In one embodiment, a liquid biodegradable polymer like polycaprolactone is used as a liquid carrier. Liquid polymeric carriers are especially useful for sustained delivery of therapeutic drugs. Many liquid polymeric carriers are known in the art and could be used. For example, U.S. Pat. Nos. 5,631,015 and 5,411,554 and references therein, cited herein for reference only, disclose various biodegradable liquid polymer compositions and methods of their preparation. Such compositions could be deposited locally using methods described in this invention. The viscosity of the liquid polymers may be adjusted using biocompatible water miscible solvents such as dimethyl sulfoxide, n-methylpyrrolidinone, ethanol, glycerol, polyethylene glycol, acetone and the like. Biocompatible polymers, preferably biodegradable polymers may also be added to increase the viscosity if needed. The list of preferred biocompatible solvents is given in earlier section. The solvent could be added in any proportions; preferably at a concentration of 1-99 percent preferably 10-90 percent. After deposition in the tissue, the solvent is dispersed by the tissue (if water soluble) leaving behind the liquid polymer droplet. The liquid polymers comprising polyethylene glycol are most preferred in many applications. One embodiment teaches synthesis of PEG polylactone polymer synthesis. By changing the molar ratio of PEG hydroxy group and cyclic lactone during synthesis, the degree of polymerization lactone in the PEG-polylactone polymer is changed. The molar ratio is adjusted in such a way that the polymerized product is liquid at ambient or body temperature. Some PEO-PPO copolymers, preferably PEO-PPO-PEO copolymers (Pluronic® or reverse Pluronic® or Tetronic® polymers from BASF or there reaction products with cyclic lactones that are liquid at room temperature could be used.

The liquid carrier described in this application can be useful for local delivery of anesthetic and pain medication. A sustained delivery of pain medication or anesthetic may be useful in pain management.

VIII. Method for In Situ Formation of Microparticles by Melting, Depositing and Cooling In Situ the Delivery of Drugs Via In Situ Formed Biodegradable Microparticles Formed from Low Melting Polymers and Non-Polymers This invention discloses in situ formation of microparticles, preferably biodegradable microparticles or microspheres at the local tissue implantation site or in the bioprosthesis tissue. FIGS. 7A through 7D disclose an embodiment for local delivery of injectable composition comprising low melting polymer preferably low melting biodegradable polymer and drug/imaging agent, at a local site inside the human/animal body such as dermis layer of the skin tissue. The composition can first be melted and then loaded in the device and injected before cooling (slow cooling composition). The composition can also be melted inside the device using local heating. After injecting the composition in the tissue using an oscillating needle, the melted composition cools at body temperature forming solid particles at the injection site.

In one embodiment, an exemplary low melting polymer, a low molecular weight polycaprolactone (PCL, molecular weight 2000 g/mole) is used. The polymer is melted by heating and delivered in situ under the skin or in bioprosthetic tissue surface using oscillating needle of a tattoo machine. For local drug delivery, the PCL polymer is first mixed with rifampin and an organic solvent that dissolves both the polymer and the drug. The solvent is removed and the mixture is melted by heating around 50-60 degree C. The melted polymer is filled inside the tattoo machine needle and deposited inside the pericardial tissue surface or in the live tissue in the shape of a 1 cm dia circle (tattooed area circle). The excess polymer on the tissue surface is wiped of. The deposited liquid polymer cools in situ inside the tissue and forms solid microparticles inside the tissue. The drug is released from the solidified particle via diffusion and/or erosion mechanism. In another embodiment, a Pluronic F127, F108 or F68 polymer, which melts around 50 to 60 degree C., is used along with a drug and colorant. The melted polymer is injected using oscillating needle under the skin. This polymer droplet cools and forms solid/gel particle and release the drug from a period of few hours to 7 days depending on the size particle and implantation site. This polymer is suitable for sustained release of drugs from few hours to 7 days. PCL is suitable for long term release of drugs generally for more than 2 months. The injected Pluronic F127 or F68 or F108 absorbs significant amount of water and swells in situ. The increase in size can potentially help to prevent migration from the implant site.

Also, compositions that are solutions at less than physiological temperature and then gel when heated to physiological temperature are known and can be used in the compositions and methods described herein.

In another embodiment, a bone wax is melted and injected in situ. Bone wax is generally considered as a biostable material. Bone wax generally melts around 50-60 degree depending the wax source and the drug and colorant loading in the wax.

In another embodiment, a non-polymeric material, steric acid is used as a carrier material. Steric acid melts around 70 degree C., however addition of drug and other components can bring down the melting temperature to 60 degree C. or lower.

In general many biocompatible or biodegradable polymers that melt below 60 degree C., preferably below 50 degree C. can be used. Many polymers and melted material do not immediately crystallized upon cooling (slow crystallization). The slow crystallization provides sufficient time in liquid state to load and infuse in the tissue. Alternatively the composition can be melted inside the delivery apparatus and then injected. Low melting polymers (melting point below 60 degree C.) that can be used include but not limited to are: polycaprolactone, polyanhydrides, Peg-polylactone copolymers, Pluronics, Tetronics, PEO-PPO-PEO block copolymers, PEO-PPO-PEO polylactones, D-α-Tocopherol polyethylene glycol 1000 succinate, fatty acids based polymers such as fatty based anhydrides and the like. Among the non-polymers that can be used include but not limited to are: wax, bone wax, fatty acids, steric acid and the like. The low melting injectable composition may be added with coloring or medical imaging agents to improve tissue infusion. The coloring compound may be added at 0.01 percent to 10 percent, preferably 0.1 percent to 5 percent range. Many bioactive compounds or drugs can be added in the low melting injectable compositions described in this invention. The drugs that tolerate heat or melting process (without loosing biological activity or with chemical decomposition) should only be used. The list of bioactive compounds or drugs is given in the definition section of this document. The compounds may be loaded at 0.1 percent to 50 percent loading level, preferably 2 to 40, percent loading level, even more preferably 5 to 30 percent loading level (relative to low melting polymer weight). The drug can be delivered from the melted polymer via diffusion and/or erosion/biodegradation mechanism. The drug can be released from few hours to few years. The average size (diameter) of melted polymer after deposition in the tissue may range from 0.1 microns to 1000 microns, preferably 10-900 microns. The shape of cooled melted polymer is spherical, elliptical, disk, plate or irregular shape. Many melted polymers could have high viscosity upon melting. Additives like plasticizers may be added to reduce the viscosity of the melted compositions. Preferred polymers or formulations will have viscosity low enough to be dispensed using the injectable device described in this invention.

IX. Method for In Situ Formation of Thermoreversible Gel Particles and Delivery of Drugs Via In Situ Thermoreversible Gel Particles This invention discloses formation of thermoreversible gels in situ wherein the thermoreversible gel particles are made inside the tissue. The preferred injectable thermoreversible compositions are injected in a fluid state (either hot or cold) in discrete way wherein more than 5 injections per minutes, preferably 10-12000 injections per minute are made inside the tissue. The injected compositions undergo in situ gelation due to thermoreversible gelation property of the composition. The gelled particles release a drug or drugs in a sustained manner. This embodiment is described in FIGS. 8A through 8D. The injectable composition is loaded inside the injection device capable of injecting the composition at 10 to 12000 injections per minute. During each injection the device can deliver 1.0E-02 to 1.0E-16 ml of injectable composition. The composition is either heated (below 60 degree C.) or cooled (0-20 degree C.) to make it fluid prior to injection. After injecting the composition, the composition undergoes temperature induced gelation at the injection site at body temperature (around 37 degree C.).

The injectable composition reservoir of the oscillating needle device can be cooled or heated to make the composition fluid and injectable. The temporary reservoir may be thermally insulated to keep the injectable composition in the fluid state.

In one extemporary embodiment, a solution or liquid that shows thermosensitive gelation behavior may also be used to infuse under the skin or in the dermis or in the bioprosthesis surface. The thermosensitive composition is delivered using oscillating needle apparatus or tattoo machine apparatus as described before. Such liquids may be preferentially colored prior to the infusion as described earlier. The thermosensitive liquids normally are fluid during injection but undergo gelation as a result of change in temperature. For example Pluronic F127 copolymer (a PEO-PPO-PEO copolymer with molecular weight of 12000 g/mole) dissolves in cold PBS (below 10 degree C.) at concentration of 20 to 50 percent. At 20 percent or higher (w/v) concentration and at warm temperature (37-45 degree C.), the F-127 solution forms a physically crosslinked hydrogel from a cold solution. This process of gelation is called as thermoreversible gelation because when the gel is cooled, it reverts back to Pluronic liquid solution. Pluronic F-127 solution (30 percent W/V in PBS along with eosin Y as red dye for visualization (0.01 percent) along with drug Rifampin (one percent, w/v) is injected as a cold liquid (0-10 degree C.) using tattoo machine apparatus as described before. The Pluronic liquid undergoes thermosensitive gelation at body temperature and forms a gel, which releases rifampin in a controlled manner. If necessary, the machine may be modified to keep the needle and machine cold during injection. The injecting machine may be kept cooled by blowing cool air on the needle to prevent premature gelation inside the needle. The color of Rifampin and Eosin Y serve as coloring agents which helps to see the injected liquid or polymer. In another embodiment, Pluronic F127, chlorhexidine acetate an antibacterial and methylene blue as a coloring agent are dissolved in cold PBS wherein Pluronic F127 concentration in the PBS is around 33 percent. At this concentration, Pluronic F127 is liquid at 0-15 degree C. but forms a gel at body temperature. The cold liquid is injected in the tissue where a change in temperature (0-15 degree C. to 37 degree C.) causes F127 solution droplets to from gel particles. The gelled particles deliver the drug compound in a sustained manner. Pluronic F127 is generally useful to deliver the compound from few hours to few days. F127 shows thermoreversible gel property at certain concentration range, generally around 15-45 percent w/v concentration range. The gelation temperature can vary depending on the solutes and drug added, drug concentration, pH and buffers used and polymer concentration. Artisans can understand that a formulation must be developed for a given drug and thermosensitive polymer wherein the polymer will show gelation property at body temperature upon implantation. It is important that many water based compositions described in this invention are osmotically balanced wherein such solution does not create any osmotic imbalance when injected inside the body.

Some polymers such as some gelatin grades or PEO-polylactone copolymers undergo gelation when injected as a hot solution (less than 65 degree C., preferably less than 50 degree C.) and cooled as to body temperature (37 degree C.) or ambient temperature may also be used. Many other types of thermosensitive polymers are known in the art. Among these biodegradable or bio-dissolvable polymers (polymers that dissolve in the human body and removed safely from the body without harmful effect) are preferred. The thermosensitive polymers that can be used include but not limited to are: Pluronic or PEO-PPO copolymers; reverse Pluronics; polyacrylamides such as poly-isopropyl acrylamide and their copolymers; gelatin (various grades); cellulose derivatives, various PEG-polylactone copolymers, PEG-PLA, PEG-PLHA, PEG-polyhydroxy copolymers, and the like. U.S. Pat. Nos. 6,004,573 and 7,740,877 and references therein, cited herein for reference only, disclose PEG based reverse thermosensitive gel compositions. Such composition may also be used for deposition inside the body using oscillating needle based device as described before.

The thermosensitive compositions described herein can deliver variety of drugs, especially protein drugs. The detailed list of drugs is given in the definition section of this document. Upto 0.1 percent 10 percent may be loaded in the thermosensitive composition. Actual loading will depend upon the type of drug used, drug solubility, type of thermosensitive polymer used and the like. As stated before, coloring or medical imaging agent may be added to thermosensitive composition to assist in the delivery of the composition and to follow its degradation after implantation. U.S. Pat. No. 7,790,141, cited herein for reference only, discloses radio-opaque compositions and such compositions may be added and used for local delivery as described before.

X. Method for In Situ Precipitation of Drug Microparticles Inside the Tissue.

XI. Method for Delivery of Drug and Water Miscible Solvents Using Oscillating Needle Apparatus This invention discloses formation of drug crystals or drug precipitates in situ inside the tissue wherein precipitated drug dissolve in the tissue/body releasing the drug in the sustained manner. The preferred drugs are water insoluble (solubility below 5 percent preferably below 1 percent) but are soluble in organic biocompatible solvents or other aqueous buffers. Such an embodiment is disclosed in FIGS. 9A through 9D.

In one illustrative embodiment, chlorhexidine diacetate salt hydrate ethanol solution is used for injection. The chlorhexidine diacetate salt hydrate has about 5 to 6 percent solubility in ethanol and 1.9 percent solubility in water. The concentrated solution of chlorhexidine diacetate salt hydrate in ethanol (saturated solution or 5-6 percent chlorhexidine solution) along with colorant are deposited inside the tissue bed or in dermis layer using oscillating needle apparatus. The ethanol in the deposited drug droplets is dispersed by the tissue or tissue fluids. Since water has limited solubility for the drug, the excess drug in the droplet is precipitated or crystallized inside the tissue bed. The slow dissolution of drug precipitates/crystals provides sustained delivery of the drug to the surrounding local tissue. The deposited chlorhexidine diacetate crystals dissolve over a period or 1 to 10 days depending on the amount deposited, the concentration in ethanol used, the particle size and the implantation site. The release of chlorhexidine provides antimicrobial local effect.

In another illustrative embodiment paclitaxel is used as water insoluble drug. Paclitaxel is approved for use in the treatment of cancer as well prevention of restenosis when released locally via a coronary stent. The solubility of paclitaxel in water is around 0.1 mg/ml in water or PBS and 1-5 mg/per ml in DMSO or ethanol. Since paclitaxel has 10 times more solubility in ethanol or DMSO than water, the solution of the paclitaxel in ethanol or DMSO can be used for local delivery using methods described in this invention. Briefly 1 mg/ml solution of paclitaxel in DMSO is deposited using oscillating needle apparatus at various locations around the cancerous tissue. Upon deposition, and dissipation of DMSO or ethanol by the tissue, paclitaxel crystals are deposited inside the tissue. The deposited crystals release the drug by slow dissolution of drug crystals providing therapeutic local effect. The paclitaxel drug can be useful for local delivery of anticancer drug in or around the cancerous tissue during an open or MIS cancer surgery. In another modification of the above example, the DMSO or ethanol solution (0.2 to 5 mg/ml concentration) is deposited in the arterial tissue immediately after balloon angioplasty or plaque removal procedure. The deposition is done using a modified version of a tattoo machine apparatus that is suitable to be used in a MIS surgical or catheter based device or technique. The modified oscillating needle apparatus is inserted in the catheter delivery system and the oscillating needle is transported at a local (balloon angioplasty site) site. The oscillating needle delivers the drug in the disease area to prevent restenosis. The needle is moved around the tissue to inject all areas affected by balloon angioplasty. The deposited solution disperses DSMO or ethanol and deposit paclitaxel crystal in the arterial tissue. The deposition depth is limited to 5-100 microns from the lumen. Preferably the embedded crystals in the arterial wall should leak into blood circulation. The entrapped crystals slowly release the drug providing antirestenosis effect. Other antirestenosis drugs such as Rapamycin, Everolimus, Atrovastatin or their derivatives or analogs and the like or may also be used for local anti-restenosis effect.

Protein growth factors such as acidic growth factors or basic growth factors are soluble in acidic or basic solutions respectively but have very low solubility under physiological conditions such as pH 7.2. Bone growth factors (BMP 1 to BMP 7), which are generally soluble in acidic solutions may be first dissolved in acidic solution and then injected in situ in the body. The change in pH can cause precipitation of the growth factors. The precipitated growth factors releases the protein drug in a sustained manner at the implantation site. It is preferred that growth factors are generally used with a carrier polymer like collagen, fibrin glue and the like.

Other additives such as polymeric materials that enhance deposition and modulate sustained delivery rate, surfactant or wetting agent to lubricate catheter surface, antioxidants, stabilizer, radio-opaque contrast agent and the like may be added to the formulation and deposited using the oscillating needle apparatus.

XII. Method for In Situ Synthesis of Desired Therapeutic or Composition by Chemical Reaction Method for Synthesis of Silver Nitrate Salts In Situ In this invention, therapeutically useful compositions are synthesized in situ using an oscillating needle apparatus. In one illustrative embodiment, silver chloride is synthesized in situ by a chemical reaction of silver nitrate with chloride ions naturally present in the physiological fluids as disclosed in FIGS. 10A through 10D.

One embodiment provides a method to synthesize silver halide in situ. 0.89 percent sodium chloride generally represent physiological concentration of salts present in the tissue. The chloride ions present in the tissue can be used to synthesize silver chloride in situ. In this method, silver nitrate solution is injected using oscillating needle. Each droplet of silver nitrate solution injected by the oscillating needle interacts with the tissue fluids and chloride ions. The silver nitrate reacts almost instantaneously with chloride ions forming water insoluble silver chloride. Since silver chloride has very low solubility in water (generally about 520 microgram per 100 g water), it precipitates in situ inside the tissue. The precipitated silver chloride dissolves slowly releasing silver ions and producing therapeutic effect (antimicrobial effect).

Silver nitrate is only one example of in situ chemical reaction. Other examples of chemical reactions that could be useful include polymerization and crosslinking reaction triggered by water in the tissue. As an illustration, polyethylene glycol with terminal isocyanate group can react with water and produce primary amine and the primary amine can reacts with isocyanate groups to form polymeric products or crosslinking product. PEG derivatives such as PEG10K4ARM glutarate NHS ester (tetrafunctional, molecular weight 10000 g/mol with n-hydroxysuccinimide end groups) and peg amine (tetrafunctional, molecular weight 10000 g/mol with amine and groups), mixed in molar equivalent quantities) can be mixed in a melt state to form a homogenous mixture in absence of water or moisture. When this melted mixture is injected in situ using oscillating needle apparatus inside the tissue, the water in the tissue triggers reaction of n-hydroxysuccinimide groups and amine groups leading to condensation polymerization and crosslinking. Other chemical reactions such enzymatically induced reactions, water induced reaction salt induced reactions can be performed in situ by the injected droplets. Artisans can understand that the above examples are for illustration only and other chemical reaction that can be done in situ may be considered as an extension of this invention.

In some cases, needle with multiple lumens may be useful to deposit various inventive compositions. As mentioned above, a multilumen needle may be used to deposit silver nitrate and sodium chloride solution (PBS solution) delivered using two different lumens. The mixing of two solutions at the injection site can immediately precipitate the silver chloride.

Other examples of chemically synthesized drugs include prodrugs (drug derivatives) which undergo chemical reaction such as hydrolysis or decomplexation to regenerate the drug in situ. Other chemical reactions assisted by enzymes may also be used to regenerate the drug from prodrug after injecting at the site.

XIII. Method for Microparticles Made Using In Situ Polymerization

XIV. Method for Deposition of Polymer Precursors Using Oscillating Needle Device.

The invention discloses methods and compositions for making encapsulated microspheres/microspheres in situ inside the tissue or inside a bioprosthesis tissue. In one embodiment, precursors that form crosslinked polymer preferably crosslinked hydrogel structures with or without cells or cellular components or drugs are disclosed. The precursors are formulated as injectable compositions with or without cells or drugs are injected in the tissue using oscillating needle apparatus as small droplets. The precursors react with themselves or components in the tissue or with external stimulus such as light that trigger a chemical reaction or crosslinking reaction forming a crosslinked structures. The crosslinking reaction converts the injected droplets into solids or gels entrapping cells or drugs. The encapsulated cells or drug provide therapeutic benefit. Preferably the crosslinked structures are biodegradable. The crosslinked structure could be hydrophobic or hydrogels or hydrophilic. This is illustrated in FIGS. 6A through 6D.

In one illustrative embodiment, a biodegradable macromonomer is synthesized and then formulated to make an injectable composition which can be triggered by long UV light or visible light. A polyethylene glycol based water soluble biodegradable macromonomer (precursor) is prepared by initiating a cyclic lactone polymerization from the hydroxy group of PEG starting material. The PEG lactate polymer is then endcapped by with polymerizable acrylate group. This is achieved by reacting the PEG-lactate diol with acryloyl chloride using triethyl amine as a base. The PEG-lactate-acrylate is designed to be water soluble and can undergo polymerization at 10 percent or higher concentration (above its critical micelle concentration in water) in water or water based buffers such as PBS buffer. The PEG-lactate-acrylate solution is mixed with photoinitiator solution (either UV light photoinitiator or visible light photoinitiator). The precursor solution along with photoinitiator is sterile filtered and deposited using a tattoo machine or other oscillating needle apparatus. The machine deposits small droplets of mixture in the tissue (dermis tissue). The polymerization is triggered by illuminating the droplets with long UV light or with visible light (514 nm). The droplets can be irradiated with light during deposition process as long as liquid compositions in the device are protected from light. The illustrative composition undergoes polymerization and crosslinking triggered by light and photoinitiator in 10 to 120 seconds. The polymerization reaction converts the liquid droplets into solid hydrogel particles entrapping the drug or cells in the crosslinked hydrogel. The crosslinked hydrogel degrades in 2-9 months due to hydrolysis of lactate group. One advantage of photopolymerization systems is that the system can be used to deliver live cells for therapeutic use. The cells could be therapeutic cells or stem cells or any other cells. The cells also could be used for tissue engineering application. The degraded hydrogels are safely removed by the body. U.S. Pat. Nos. 5,529,914 and 5,410,016, cited herein for reference only, can provide additional compositions and methods for photopolymerizable biodegradable or biostable hydrogels and their use in cell encapsulation. Many polymerizable precursors are known in the prior art and can be deposited and crosslinked using the method described in this invention. Protein based macromonomers such as collagen, keratin or albumin can be modified with photopolymerizable groups and crosslinked in situ using methods described in this invention.

Another embodiment describes condensation polymerization of precursors, preferably PEG based precursors. In this illustrative embodiment, NHS ester of PEG and albumin or trilysine are mixed to form a precursor solution. The mixed solution is then deposited inside the tissue using tattoo machine like device or oscillating needle apparatus. The deposition is done prior to complete crosslinking or change in viscosity or gelling the solution. Premature crosslinking can prevent the deposition using the oscillating needle machine. It is preferred that the composition is mixed just prior to infusion and used immediately. In the preferred embodiment, the precursor solutions are mixed inside the oscillating needle apparatus in a mixing chamber and used immediately for the infusion inside the tissue. In one illustrative embodiment, PEG NHS ester and albumin solutions are mixed in PBS (pH 7.2) is used. The composition forms gel in 30-60 seconds and is injected using this apparatus before that. Many types of condensation polymerization systems are known in the art and such reaction can be used making gel particles in situ as described in this invention. U.S. Pat. Nos. 6,887,974, 7,592,418, and 6,323,278 and cited references therein, cited for reference only, can provide various compositions that can polymerized in situ using condensation polymerization. Other precursors that can be used for in situ polymerization used include but not limited to: precursors that form crosslinking by the reaction of isocyanate and alcohols or amine and epoxide or acrylate and amine, acrylate and thiol and the like may also be used. Ionic crosslinking such as crosslinking of sodium alginate solution (0.2 percent solution in deionized water) with calcium chloride solution (2 percent in distilled water) can also be used. In this case a two-needle delivery system is used or multilane needle is used. One needle or lumen delivers the 1 percent sodium alginate solution and another needle/lumen delivers calcium chloride solution. The interaction of two droplets triggers ionic crosslinking of sodium alginate forming crosslinked calcium hydrogel particle in situ.

In another embodiment, the precursors react via enzymatic pathway to form a crosslinked (physically and chemically crosslinked) compositions. Fibrin glue particles are used as an illustration of enzymatically formed microparticles. In this illustrative embodiment fibrin glue particles are formed in situ. Briefly fibrin glue precursors are deposited prior to gelation using tattoo machine inside the tissue. The precursors droplets react with each other forming fibrin glue hydrogel particles in situ. Fibrin glue formation is a complex enzymatic reaction. The solution of concentrated fibrinogen and factor XIII are combined with a solution of thrombin and calcium. Once the thrombin/calcium is combined with the fibrinogen/factor XIII, a fibrin clot forms in few seconds to few minutes, depending on the thrombin concentration, temperature, calcium ion concentration, fibrinogen concentration and the like. The fibrin glue components are mixed and deposited inside the tissue prior to gel or clot formation (within few seconds). The factor XIII in the formulation continue to act for several days leading to covalently crosslinked fibrin gel. If drugs are entrapped in the fibrin clot, it is released from the clot via diffusion and/or biodegradation process. In the preferred formulation, the fibrin glue is colored for improved visualization. Alternatively precursors of fibrin glue can be delivered using multilumen needle or bi-needle based oscillating machine similar to described for alginate gel making. Fibrin glue and PEG based biodegradable hydrogels described above are especially useful for delivery of protein drugs like growth factors or therapeutic cells. U.S. Pat. No. 8,557,535 and references and cross-references therein; describe some fibrin glue compositions, cited herein for reference only. Such compositions could also be used for local deliver of fibrin glue based compositions described above. The precursor solutions may be preferably deposited using a multilumen needle as described before. For example solution comprising fibrinogen may be fed via one lumen and the solution comprising thrombin may be fed by another lumen. Both the solutions may exit at the same time, mixed in situ and react to form a crosslinked material in situ. Fibrin glue may be especially suitable for delivery of cells. The therapeutic cells such as stem cells may be mixed with fibrinogen solution and the solution is crosslinked by reacting with thrombin as described above. The entrapped cells in the crosslinked network may provide therapeutic effect.

The amount of drug that can be injected may range from 0.1 percent to 30 percent, preferably 1 to 10 percent depending on the drug to be delivered and disease that has been addressed. The size of hydrogel particles will depend on the oscillating needle device used. The size of hydrogel may range from 1000 microns to 0.1 microns, preferably 1 micron to 900 microns.

XV. Method for Infusion of Particles in the Tissue by Bombardment

In one embodiment, drug particles are infused by bombarding the tissue of a bioprosthesis. The bombarded particles have predetermined level of kinetic energy or velocity so that they penetrate the tissue body and stay embedded inside the body. If the particles have drug encapsulated in them, then the drug is released from the particles for therapeutic action. In the preferred embodiments, the drug particles may be bombarded with sufficient high velocity so that they penetrate tissue surface and are physically embedded in the tissue body or surface. This can be achieved by providing sufficient kinetic energy to the drug particles or microencapsulated particles so that they can penetrate the tissue surface/body. The lesser kinetic energy will not achieve penetration and excessive energy will penetrate and pass through the tissue body completely. Both such situations must be avoided. FIG. 1A shows a partial representation of a method for infusing drug/microencapsulated particles in the bioprosthetic tissue. The drug particle are fed through a reservoir of a machine capable of providing high velocity to the particles where particles are given high kinetic energy/velocity using a gas pressure or other means and bombarded on the tissue surface. Exemplary machines such as sand blasting machine can be used in this application. The kinetic energy is controlled in a way that the particles are embedded in 10 to 2000 micron dip inside the surface, preferably 20-1000 micron dip. In the most preferred methods, the particles are embedded in surface layers and can be seen with the help of a human eye. In one exemplary embodiment, the drug particles (fine sugar powder or colored sand beads as model drug particles) are bombarded on a flat bioprosthesis tissue surface like bovine pericardium surface. Standard sandblasting equipment and pressurized air/nitrogen are used to provide kinetic energy to the drug particles. The compressed gas pressure is adjusted via a gas pressure regulator in a way to give sufficient energy to the particles, which will penetrate the prosthetic tissue surface about 10-1000 microns. It will be more advantage if the particles are colored so that the amount of particles can be visually controlled. Bovine pericardium is white or off-white in color, any color that can be easily detected against that background can be useful. Blue, green black colored particles are most preferred. The bovine pericardium tissue is used as an exemplary surface; other tissues may also be used. After sufficient loading of particles in the tissue body, the process is stopped. The drug particles are bombarded on the surface of pericardial tissue prior to fabrication into any bioprosthesis. The drug loaded pericardial tissue is then used in bioprosthesis fabrication as described in this invention. Many other methods for providing kinetic energy to the particles or bombardment known to the one skilled the art may be used. Kinetic energy provided to the particles by pressurized gas such as pressurized air or pressurized nitrogen gas is preferred. Explosive force, electromagnetic or magnetic methods may also be used to provide kinetic energy. Some or all parts of the tissue may be used for particle infusion; for example only ten percent of the pericardial surgical patch at the center may be infused with antibiotic or antirestenosis compound. The area of drug incorporation will depend on the bioprosthesis and the desired clinical outcome. The area covered by the particles may range from one percent to 99 percent. A tissue based small or medium graft, or stent bioprosthesis can be infused using drug particles. Anti-restenosis drugs particles such paclitaxel or microencapsulated rapamycin may be infused in the luminal wall of the bioprosthetic device. The tissue used in bioprosthesis may be crosslinked or biostable. The tissue may also be biodegradable such as uncrosslinked tissue or EDC crosslinked tissue or tissue that is crosslinked with biodegradable crosslinker. The particle infusion can be done before bioprosthesis fabrication, during intermediate stage of fabrication or after complete fabrication of the device. The preferred size of particles that can be infused may range from 0.01 micron to 1000 microns, preferably 0.1 micron to 500 microns. Even more preferably from 0.5 micron to 400 microns.

Method of Forming Microparticles In Situ

The method generally involves, providing an injectable composition-comprising polymer dissolved in water miscible biocompatible solvent, injecting the solution using oscillating needle oscillating at the rate of 30-12000 oscillations per minute in the tissue in a desired shape. The volume of the injected droplets is generally less than 1.0E-02 ml. The injected droplets are injected in such a manner that the injected particles generally cannot fuse with each other. In general, the distance between the two or more injected droplets is more than the average diameter of the injected droplet, typically 10 to 10000 percent more than average diameter of the droplet injected. If d is average diameter of the injected droplet and if D is the distance between two injected neighboring droplet, then generally D generally greater than d. The ratio of D/d may be 1.1 to 50 depending on the injectable composition used. The distance between injected droplets may vary form 10 microns to 1 cm depending on the injectable composition used, rate of chemical or physical change, size of injected droplets and the like. If large gap is used between the droplets, the unused tissue space between the droplets may be reused for injection of additional droplets after the chemical or physical change has taken place. This way more particles can be formed in a smaller space. The size of the droplet injected will depend on many factors such as that needle diameter, flow of injectable composition, oscillation rate and the like. The gap between two neighboring injected droplets provides a barrier for fusion or agglomeration of droplets. Generally 3 or more, preferably 5 or more injected droplets are prevented form fusing or coalescing to form big particles. The isolation of droplets provides sufficient time to diffuse the solvent out or to cool the injected melted composition or to complete a crosslinking reaction in situ or to undergo thermoreversible gel formation and the like. Once the polymer is precipitated or melted solid is cooled or the droplet is chemically crosslinked or transformed into a gel via thermoreversible gel formation, then fusion of injected droplets is generally not possible and microparticles can form in the tissue. The fusion of liquid droplets generally must not occur before desired chemical or physical change occurs. In case of polymer solution, it must not occur before the solvent diffusion and precipitation of the polymer. This generally happens in 1 to 30 minutes. In case of crosslinkable composition, the fusion must not occur before crosslinking reaction, which may take 30 seconds to 30 minutes. In case of melted composition, the fusion must not occur before cooling and solidifying the melted droplets. In case of thermoreversible composition, it must not occur, before the gelation is triggered by temperature change. In some cases, some fusion may be unavoidable and this can result into formation of particles with various sizes and shapes. The injected droplets may not be mechanically agitated to discourage fusion process. This is especially useful when injecting under the skin tissue. The skin tissue may not be pressed or rubbed or massaged in the injected area to discourage fusion of injected droplets especially before the chemical or physical change occurs. In one illustrative embodiment, the PLGA polymer solution in DMSO along with drug rifampin is hand injected in a chicken leg muscle and/or in the gelatin gel as a model tissue surface. The solution is hand injected to keep the distance 1-5 mm between the droplets. After the diffusion of the solvent DMSO or gelatin gel, the particles are isolated and observed under microscope for size and distribution measurement. The large gap between the injected droplets enables sufficient time for DMSO diffusion and precipitation of PLGA polymer without fusion. In general variables such polymer solution viscosity, diffusion of solvent in the tissue, polymer precipitation rate, droplet volume, spacing between each injected droplet and the like may be optimized to prevent fusion of injected particles and to encourage microparticle formation. It is preferred that robotic arm or machine assisted deposition process may be used to form high density of particles in a given tissue area.

Description of Forming In Situ Film or Implant

Accordingly, the present invention discloses methods and compositions for delivering implants of relatively larger size, such as having area greater than 5 mm square and that are formed in situ, preferably under the skin by fusion of polymer solution droplets. The method generally involves, providing an injectable composition comprising polymer dissolved in water miscible biocompatible solvent, injecting the solution using oscillating needle oscillating at the rate of 30-12000 oscillations per minute in the tissue in a desired shape; The volume of the injected droplets is generally less than 1.0E-02 ml. The injected droplets are injected in such a manner that the injected particles can fuse with each other. In general, the distance between the two or more injected droplets is leas than the average diameter of the injected droplet. The shorter distance between the injected droplets forces the overlapping of liquid droplets, which encourages fusion or agglomeration. If d is average diameter of the injected droplet and if D is the distance between two injected neighboring droplet, then generally D is less than d. The overlapping area between the two neighboring droplets is greater than 5 percent, preferably greater than 20 percent. The fusion of liquid droplets must occur before any chemical or physical change occurs. In case of polymer solution, it must occur before the solvent diffusion and precipitation of the polymer. This generally happens within 1 to 30 minutes. In case of crosslinkable composition, the fusion must occur before crosslinking reaction, which may take 30 seconds to 10 minutes depending on the crosslinking chemistry used. In case of melted composition, the fusion must occur before cooling and solidifying the melted droplets. In case of thermoreversible composition, fusion must occur, before the gelation is triggered by temperature change. The fusion of several injected particles, generally fusion of 10 or more droplets, generally more than 30 droplets or more can lead to larger mass with area greater than 5 mm square. The injected droplets may be mechanically agitated to encourage or accelerate fusion process. This is especially useful when injecting under the skin tissue. The skin tissue may be pressed or rubbed or massaged in the injected area to encourage/enhance fusion of injected droplets. In one illustrative embodiment, the PLGA polymer solution along with drug rifampin is injected in a chicken leg muscle and/or in the gelatin gel as a model tissue surface. The composition is injected using an oscillating needle device oscillating at 50-3000 minutes per seconds. The injection is placed close to each other around 1-20 microns apart wherein the size of injected volume is greater than 1.0E-02 ml. The composition is injected in an area 1 cm by 1 cm as a solid square. The injected composition is visible to the naked eye due to red color of the rifampin. The injected area is gently massaged by hand for 10 minutes. After 10-60 minutes of infusion wherein the solvent in the injected composition has diffused out, the precipitated composition is observed under microscope. The semi solid film of PLGA polymer is clearly seen. It is understood that many types of polymers (biodegradable or biostable) can be used to form films or implants in situ inside the body. The biodegradable polymers, especially polymer made of polyhydroxy acids or polylactones, or PEG-polylactone copolymers are useful for local sustained drug delivery. Biocompatible solvents such as water with various buffering agents, DMSO, NMP, acetone, ethanol and the may be used to dissolve biodegradable polymers. The polymer concentration the solution may range from 1 to 60 percent depending on the molecular weight of the polymer and type of solvent used. In general the viscosity of injectable composition must be such that it can be injected using oscillating device. The in situ formed films or implants may be used for sustained drug delivery. The type of drug used will depend on the desired clinical need. The drug concentration in the film relative to polymer weight may vary from 1 to 40 percent. The spacing between injections may be critical for forming film in situ. Close spacing between each injection will result in agglomeration or fusion of injected droplets leading to film or implant formation in situ. Several droplets may need to be fused to form film or implant in situ. The spacing between the injected liquid droplets will depend on the injectable composition or polymer solution used and droplet volume. In general variables such polymer solution viscosity, rate of diffusion of solvent in the tissue, polymer precipitation rate, droplet volume, spacing between each injected droplet and the like may be optimized to prevent or encourage fusion of injected particles. If objective is to form a film or implant formation in situ, the close injections of injected droplets and bigger droplet volume is preferred and the fusion or agglomeration of injected droplets is encouraged. The size and shape of the film or implant will depend on the injection pattern. The film or implant formed may be of regular shape such as circular disk or ring, a straight or crossed lines, rectangular, triangular, hexagonal, and pentagonal and the like or it may be of irregular shape. The shape of implant formed may be symmetrical or non-symmetrical. The shape of the implant or film may also be present as an artistic figure such as smiley face or shape of a star or flower and the like. A visualization agent or colorant may be added to assist in the deposition process. Large films or implants can be made of desirable size by injecting over a larger area of the tissue or skin. One advantage of this invention is that large films can be made in situ and such films do not have to be made outside and then implanted surgically.

Description of In Situ Crosslinking of Live or Bioprosthesis Tissues.

In another embodiment, a crosslinker that can react in situ with the live tissue or bioprosthesis tissue to crosslink the tissue is used. The composition, preferably colored or fluorescent composition is injected using oscillating device described in this invention. Upon injection, the injected composition reacts with the extracellular proteins in the tissue under effective crosslinking conditions and forms effective crosslinks with the tissue. The crosslinked tissue can have different physical and chemical properties than unmodified tissue. Generally drugs and crosslinking agents cannot penetrate inside the eye when applied topically in the eye. The diffusional barrier is a natural protection for the eye to protect it from unwanted chemicals found outside the eye. The inventive compositions break this diffusion barrier mechanically by injecting the sustained drug delivery or tissue crosslinking compassions using an oscillating needle or multiple needles like devices. The oscillation and deposition depth in the cornea can be varied depending on the device parameters used. In the cornea, the crosslinking or drug delivery compositions may be deposited at a depth of 5-500 microns, preferably at a depth of 10-300 microns. The deposited compositions undergo crosslinking reaction with the cornea tissue and thus help to stabilize the cornea tissue. The crosslinked tissue produced may be biodegradable or biostable. In cornea application, the crosslinker compositions comprising PEG or PEG-PPO copolymers or Pluronic polymers are highly preferred due to their low ophthalmic tissue toxicity. Activated acid crosslinkers, preferably short chain di-polyacid derivatives are more useful in producing biostable tissues. Among activated esters, n-hydroxysuccinimide, n-hydroxysulfosuccinimide, n-hydroxymaleimide derivatives are preferred. The n-hydroxysulfosuccinimide esters are most preferred because the sulfonate groups in the ester provide water solubility to the crosslinker. In the illustrative embodiment (Example 23 and 24), an activated di- or polyacid, such as PEG based crosslinker (Example 24) is used to crosslink live cornea tissue. The crosslinking of live cornea tissue can potentially help to treat certain medical conditions such as Keratoconus. Or Keratectasia. The infusion of crosslinking agent using an oscillating needle can help to infuse tissue crosslinker in the cornea, in particular corneal stroma, without removal of corneal epithelium and can crosslink the corneal tissue in situ. If needed only certain parts or the cornea tissue may be treated or crosslinked. In the illustrative example, PEG10K4ARM glutarate NHS ester is used as an exemplary non-toxic biocompatible crosslinker. Other crosslinkers that can be tolerated by live ophthalmic tissue in particular cornea tissue can also be used. The preferred crosslinkers that may be used include but not limited to: activated di-polyacid ester, especially n-hydroxysuccinimide, n-hydroxysulfosuccinimide, n-hydroxymaleimide derivatives. The bi or polyfunctional activated acids that can be used include but not limited to: ethanedioic acid, malonic acid, succinic acid, glutaric acid, adipic acid, pimelic acid, suberic acid, azelaic acid, sebacic acid, undecanedioic acid, dodecanedioic acid, maleic acid, fumaric acid, gluconic acid, traumatic acid, mucocin acid, itaconic acid, citric acid, butane tetracarboxylic acid, polymeric acids such polyvinyl pyrrolidinone-co-polyacrylic acid, acrylic acid copolymers, polyaspartic acid, hyaluronic acid, protein or peptide sequences comprising acid resides and the like.

In bioprosthesis applications, the infused compositions may be used to crosslink certain area of a bioprosthesis tissue. The injected part of the tissue area may be made biostable or crosslinked depending on the type of crosslinker used. If biodegradable crosslinker (PEG10K4ARM glutarate NHS ester as an example of biodegradable ester) is used, then the resultant tissue is considered as biodegradable. If the standard tissue crosslinker such as glutaraldehyde or diisocyanate is used, then the tissue may be considered as biostable. The un-injected or untreated part of the tissue is considered as biodegradable tissue. Example 23 illustrates one such example wherein a colored crosslinking composition is infused only in certain parts of tissue to crosslink only infused and surrounding area. It is preferred that diffusion of crosslinking agent is restricted to only area of infusion. Polymeric crosslinker, typically PEG based crosslinkers are especially useful in such applications. Polymeric crosslinkers that have bigger molecular size and therefor cannot diffuse into surrounding tissue by diffusion process. Small molecule crosslinking agents, generally with molecular weight below 2000 g/mole, like glutaraldehyde or 1-ethyl-3-(3-dimethylaminopropyl) carbodiimide (EDC) and the like are more prone to diffuse in the surrounding tissue and can crosslink the neighboring tissue. The infusion of injectable composition or tissue crosslinker solution can be done in any shape of pattern as described previously. The selective infusion can fix or crosslink specific parts of the tissue that needs to be crosslinked. The area where tissue is not infused can remain uncrosslinked. Thus a pattern of crosslinked and not-crosslinked tissue can be created in a bioprosthesis tissues like pericardium or submucosa tissue. The crosslinked tissue can be considered as biostable and not-crosslinked tissue is considered as biodegradable. Thus a pattern of biodegradable and biostable tissue can be created in the same tissue such as pericardium tissue.

Applications of Local Drug Delivery Described in this Invention

The compositions and methods described in this invention can be applied to variety of surgical situations. The surgical situations where the inventive compositions and methods could be applied include but not limited to: abdominal surgery, bariatric surgery, cardiac surgery, cardiothoracic surgery, colon & rectal surgery, general surgery, gynecologic surgery, maxillofacial surgery, neurosurgery, obstetrics surgery, oncology related surgery, ophthalmology related surgery, oral surgery, orthopedic surgery, otolaryngology related surgery (ear, nose and throat, ent surgery), pediatric surgery, plastic surgery, cosmetic & reconstructive surgery, podiatry surgery (podiatry), thoracic surgery, transplant surgery, trauma surgery, and vascular surgery and the like. The methods may be especially useful when used in open surgical procedures; MIS surgical procedures and catheter based surgical procedures such as balloon angioplasty procedures can also take advantage of the inventive methods and composition. The injection device need to be modified for each branch of MIS procedure.

The inventive compositions could be used in open surgical procedures to reduce incidence of bacterial or fungal infection. For example, major surgical incisions could be closed using conventional methods such as absorbable or non-absorbable sutures and tissues nearby closed incisions may be "tattooed" or infused with oscillating needle with compositions comprising antibiotics or antibacterial compounds. The infused antibiotics could release the antibiotic in a sustained manner. Major surgeries like knee or hip implant surgery, open heart surgery, childbirth surgery and the like wherein major surgical incisions are involved could benefit from this invention.

FIGS. 15A through 15E show partial schematic representation of local drug therapy made using compositions and methods described in this invention. FIG. 15A schematically represents a closed surgical incision 1501 such as incision wound made during cesarean section operation. FIG. 15B shows the deposition of injectable composition in the surface tissue surrounding the surgical incision. The deposited composition is visible to the naked human eye (solid line, 1502 and can provide sustain release of therapeutically effective drug dose such as antibiotic to the surgical wound. If desired, another drug (shown as dotted line 1503, FIG. 15C) can be deposited in the skin tissue surrounding the surgical wound using methods prescribed in the invention to reduce scar tissue formation or other useful effect.

Implant revision surgeries such hip, knee, heart valve, coronary bypass, hernia patch, weight loss surgery and the like can also benefit from this invention. Some medical device revision surgeries such as hip, knee, heat valve, coronary bypass, hernia patch revision surgeries involve bacterial infection. In such situations, the infected tissue area may be infused with sustained releasing antibiotic compositions described in this invention.

Pain management involves controlled dose of pain medication preferably at the pain site in the body. Many opium derivatives can have excellent pain management abilities, such derivatives could be delivered using compositions and methods described in this invention. Many sports injury require local pain managements and such injuries can be treated by inventive commotions and methods.

Periodontal infections could be managed by delivering the antibiotics in the periodontal pocket. Briefly under local anesthesia, the affected gum pockets are infused with the sustained releasing compositions described in this invention. The compositions could deliver antibiotics from 1 to 40 days for effective infection management. The polymer solutions such as PLGA solutions with antibiotics could be infused in the affected gum tissue using the oscillating needle based device described in this invention. Other dental procedures like tooth removal may benefit by infusing the affected area with antibiotics. The local anesthetic given during dental or other surgical procedures may especially benefit from this invention. If a colored or fluorescent composition is used, the precise area where anesthetic is delivered could be seen and managed. It is understood that oscillating needle size will vary depending on the application. Fine needle are used where small amount of anesthetic or drugs are needed. Larger size needle may be beneficial when large dose is delivered in a large area.

Acne is a skin condition that is formed when pores in skin are blocked. The blockage generally results into bacterial contamination, which leads to inflammatory response. The inflammatory response or acne lesions may be small and can have white or black head, or can appear red with a white/yellow. The local infusion of conventional medicines such as antibiotics or other drugs around the acne area using methods described in this invention can be used for acne treatment. Herbal remedies can be delivered at or around acne area using the methods and devices described in this invention. Mouth blisters also can be treated in a similar fashion as acne. In Acne treatment, a non-colored or transparent injectable composition may be preferred. Being a facial and temporary implant, the color of implant in the facial skin may not be preferred by the patient. If color is used in the acne treatment, it could only assist in making precise deposition and then dissolve or biodegrade in very short period of time preferably ranging from few minutes to 24-72 h. Transparent biodegradable hydrogel based compositions preferably PEG based hydrogels are most preferred. Such hydrogel may be deposited as dry particles and can absorb local fluids to swell in situ. A highly water soluble colorant such as indocyanine green or methylene blue may be used to visualize the hydrogel which can be eluted out in a short period of time leaving behind a transparent hydrogel for sustained drug delivery. Bioactive compounds like Doxycycline, Tetracycline, Minocycline, Isotretinoin (13-cis-retinoic acid), Benzoyl peroxide (BPO), Clindamycin, Erythromycin, Tetracycline, Tretinoin, Tazarotene, Green tea extracts, Laurie acid, Retinoic acid, Cyproterone acetate, Finasteride, Tea oil, Methylene blue Spironolactone, Prednisone, Dexamethasone, Cyproterone and the like may be used for sustained drug delivery and treatment of acne.

FIG. 15D schematically shows acne or mouth blister 1504 that needs to be treated using local drug therapy. FIG. 15E shows the deposition of drug 1505 surrounding acene or blister that provide local sustained drug delivery to the acene or blister.

Cosmetic ingredients such as fruit acids, Botox®, Dysport®, vitamin E or other oils, herbal or Aurvedic medicines (ancient medical practice in India) such as turmeric and the like may be infused in the skin using methods described in this invention. Botox and Dysport infusions could be especially benefited from this invention due to precise control over its infusion. Both Botox and Dysport could be infused as colored or fluorescent composition, which could help to manage the infusion process visually. One embodiment in this invention teaches the use of colored Botox formulation for cosmetic and other medical uses. The protein in the Botox drug could be made colored by covalently attaching dyes such as fluorscein and other dyes. The covalent bonds may be formed via amine, carboxylic acid, thiol, alcohol and other functional groups in the protein and the dye. Modification of protein therapeutics by PEG is well known in the art (Roberts M. J. et al), cited herein for references only. Such method could be adopted for protein modification with colorant or chromophore. Covalent boding that reduces or eliminates therapeutic properties of the protein should not be used. The color or chromophore may be ionically (cationic or anionic) bonded to the protein. Alternatively colorant such as fluorscein may be physically mixed with the Botox solution to make it colored or fluorescent. If physically mixed, it is preferred that the colorant used could have similar diffusion characteristics as the drug itself. Since Botox is a macromolecular drug, a macromolecular colored additive such as fluorscein modified with albumin, dextran or PEG could be preferentially used.

Tissues in the infected wounds could be infused with this procedure with or without the use of local anesthetic. Other wound management medicines such as growth factors may also be locally infused for wound management and scar tissue reduction.

In some embodiments, MIS devices like catheter balloons may be fitted with oscillating needles and used for local delivery of drug in the arterial, cardiovascular tissue or other tissue. The pen like injectable device can also be used during laparoscopic surgery can be useful for local drug therapy in the peritoneal cavity. A hole in the stomach wall is created during the laparoscopic surgery. Laparoscopic tools are inserted through the hole that has been created. An oscillating needle based device that can be used with laparoscopic instrumentation can be inserted through the hole and localized drug therapy is administered using such device. Briefly, sustained drug delivery compositions can be infused in the desired area in the stomach cavity. Upon infusion, the drug is released from the infused compositions in a sustained manner. Other MIS surgical techniques may also be used in a similar fashion.

One embodiment of this invention teaches the use of this invention for treatment of cancer. The cancerous tumors could be infused in a precise geometry and shape using cancer medicines such as paclitaxel and the like. The colored compositions can be especially useful to cover affected disease area. Compounds that are used in photodynamic therapy may also be infused using methods described in this invention and then irradiated with light for therapeutic effect.

Restenosis is a major complication associated with a balloon angioplasty procedure. The antirestenosis drugs could be delivered using catheter based infusing techniques described in this invention. Drugs like paclitaxel, everolimus, rapamycin could be delivered locally at the angioplasty site using catheter based techniques.

Medical devices or bioprostheses such as tissue based hernia patch, tissue based heart valve, wound covering, vascular grafts may be infused with drugs using methods and compositions described in this invention. A bovine pericardial based surgical patch or tissue based hernia patch or submucosa based devices like wound covering (Oasis Wound Matrix for example) could be infused with drugs such as antibiotics prior to implantation. The type of drug and the amount of drug used will depend on the final application and clinical need. For example, vascular graft or carotid patch application, antirestenosis drug could be infused into luminal surface of the vascular graft or carotid patch. In a wound healing application, a growth factor or an antibiotic releasing composition may be used.

The infusion solutions and supplies (needles) may be supplied as a surgical kit in the operating room. For example, a kit consisting of A) a sterile drug vial and colorant; B) a sterile biodegradable polymer solution in DMSO supplied as prefilled syringe and C) a disposable tattoo like needle can be attached to the device is supplied as a kit. The DMSO solution is injected in the drug vial where it dissolves the drug and colorant to form a solution/suspension. The tattoo needle is attached to a sterile oscillating needle device. The needle is filled with the DMSO-Drug-Polymer and the composition is infused in the tissue as described in this invention. The infused composition form drug encapsulated microparticles in situ. The polymer, drug and color are safely removed by biodegradation process. It is understood that many variations can be made to the kit. For example, colorant may be added in prefilled polymer solution and only drug vial is provided. In another variation, injectable colored composition along with drug may be supplied as a sterile "disposable ink like cartilage" which can be attached to the delivery device. Such variations and other combinations are considered as a part of this invention. In another variation of the kit, sterile drug loaded biodegradable microspheres/microparticles; preferably colored microspheres are provided in a vial. In another vial, sterile phosphate buffered solution along with additives such as glycerin, surfactant, viscosity modifier, and the like that is formulated specifically for the microspheres to form a stable suspension/emulsion is provided. The buffered solution is added to microsphere vial prior to use and mixed to form a stable injectable composition. The composition is injected using methods described in this invention for local sustained drug delivery.

In ophthalmic application, the ophthalmic tissue, preferably corneal tissue may be tattooed or infused with sustained drug releasing compositions described in this invention. Generally human cornea has a thickness of 400-600 microns. The surface of the cornea tissue could be used to deposit variety of sustained drug delivery compositions. Preferably such compositions could be preferably deposited at a depth of 10-300 micron depth in the ophthalmic tissue via surgical procedure. Drugs that treat medical conditions such as glaucoma, macular degeneration diseases, bacterial or viral infection, inflammation and the like may be infused in the ophthalmic tissue. The drugs that may be infused include but not limited to: tramadol, aproclonidine, brimonidine, ketoconazole, ofloxacin, ketorolac tromethamine, pyrimethamine, prednisolone sodium phosphate, tetracaine HCl, dexamethasone, timolol, tobramycin, rimexolone, sulfadiazine, bromocriptine, flucytosine, cyclopentolate HCl, ganciclovir sodium, epinastine HCl, physostigmine, echothiophate, carbonic anhydrase inhibitors, fluocinolone acetonide, valganciclovir HCl, antazoline phosphate, medrysone, acetaminophen and codeine, levobunolol, vitamins A, Vitamin E, ceftriaxone, gentamicin, ephedrine hydrochloride, gentamycin, rose begal, scopolamine HBr, suprofen, polymyxin B, norfloxacin, cephalexin, olopatadine HCl, antioxidants, azathioprine, lutein, diclofenac sodium, indocyanine green, doxycycline, carteolol, fluorescein, latanoprost, ibuprofen, acetaminophen, proparacaine HCl, uravoprost, sodium sulfacetamide, unoprostone cidofovir, dipivefrin, taurine, levocabastine HCl, fomivirsen sodium, homatropine, famciclovir, atropine sulfate, naphazoline hydrochloride, vancomycin, flurbiprofen sodium, bimatoprost, cromolyn sodium, fluconazole, emadastine difumerate, tropicamide, dexamethasone sodium phosphate, dorzolamide, prednisolone acetate, fluoromethalone acetate, sissamine green, ofloxacin, levofloxacin, ciprofloxacin, proparacaine HCl and fluorescein sodium, brinzolamide, phenylephrine HCl, tetrahydrozoline hydrochloride, lodoxamide tromethamine, sulfisoxazole diolamine, fluorometholone, trifluridine, ketotifen fumerate, gatifloxacin, loteprednol etabonate, foscarnet sodium, phenylephrine hydrochloride-ketorolac, erythromycin, amikacin, cyclosporine, acyclovir, dicloxacillin, itraconazole, zeaxanthin, azelastine HCl, betaxolol, nedocromil sodium, amphotericin B, methazolamide; prostoglandins, prostamides amoxicillin/clavulanate, rapamycin methotrexate, acetaminophen, hydrocodone, permirolast potassium, azithromycin, pheniramine maleate, benoxinate and fluorescein sodium, moxifloxacin, benoxinate, fluorexon disodium, sulfisoxazolone diolamine, epinephrines, acetazolamide, nutraceuticals, cefixime, glutathione, oxymetazoline, fluorexon, carbachol, pilocarpine, cholinesterase inhibitors, metipranolol, sodium sulfacetamide and tetracycline and the like. Ophthalmic bioprostheses such as donated human cornea or animal tissue based cornea may also be infused with sustained releasing composition. Cornea could be also crosslinked in situ as described previously. FIG. 21B shows a PLGA based biodegradable florescent composition embedded in the cornea tissue. The plus sign shape of the composition is clearly seen in the blue light. The embedded composition can provide sustained drug delivery. Alternatively porcine cornea tissue infused with drug delivery composition may be used us a temporary drug delivery contact lens for local delivery of ophthalmic drugs.

A multi-needle injectable device where 5 to 10000 micro needles or more are arranged in the shape of a circle (needles are placed on circumference of a circle) may be specially designed for delivering the sustained drug delivery compositions for ophthalmic or acne and other medical application. Each needle may be able to dispense 0.01 ml or less volume of injectable compositions comprising drugs, preferably ophthalmic drugs in the cornea tissue surface or skin surface simultaneously. The compositions may be deposited at a depth of 10 to 300 microns in cornea or skin. Upon deposition, the injected composition will release the ophthalmic drug in the cornea for treating conditions such as bacterial infection, pain, inflammation, glaucoma, age-related macular degeneration and the like. Circular shape mentioned above is for example only. Other shapes such a single line, two crossed lines like and the like may also be used.

The compositions and methods described in this invention could be used to make biodegradable tattoos. The colored biodegradable particles (without drugs) may be formed by injecting the colored biodegradable microspheres in the skin tissue using tattoo like device. Colored biodegradable microparticles may also be formed in situ at the implant site (in situ polymer precipitation). Many types of biodegradable polymers may be used to make biodegradable tattoos. Particles made using polyhydroxy acids or polylactone or its copolymers are especially useful. The biodegradation time may be varied by choosing type of biodegradable polymer used. For example, if 2-3 years of degradation time is desired, polycaprolactone based particles may be used. If 0.5 to 1 year biodegradation time is desired, polylactide based microparticles could be used. Polyglycolic based particles could be used for short duration tattoos (30-90) days. For intermediate biodegradation times, blends or copolymers such polymers may be used.

In biodegradable tattoo application, the colorant used is preferably stable to environmental conditions such as ambient light or sun light exposure.

The inventive applications and methods may be used to treat post-operative adhesions. Prevention of post-operative adhesions may be achieved by creating a temporary barrier between the two organs involved or localized sustained drug delivery. In one inventive approach, the oscillating needle device is used to infuse the PEG based crosslinker solution, preferably PEG based biodegradable crosslinker in the affected tissue using an oscillating needle device. The solution is infused only in the surface layers, preferably at the depth of 5-500 microns, preferably at a depth of 10-300 microns, even more preferably at 10-50 microns depth. It is believed that presence of PEG in surface layer can help in reducing protein adsorption and therefore unwanted cell growth and subsequent scar formation can be reduced. In another embodiment, a known coating agent, such as hyaluronic acid sodium salt, or Pluronic F127 polymer or other PEG based polymers and the like that are known in the postoperative prevention art may be infused in the tissue surface layers. The infusion in the tissue area is generally enhanced by addition of biocompatible colorant in the composition. In one illustrative embodiment, (Example 24), sodium hyaluronate along with colorant is infused in the surface layers of the tissue. The presence of biocompatible polymers locked in the surface layers of the tissue can potentially reduce incidence of postoperative adhesions. In another approach, drugs such as TPA which is known to reduce post operative adhesions in animal models may be infused using oscillating needle apparatus directly in the tissue surface layers. In another embodiment, sustained drug delivery compositions of TPA, in the form of a microspheres or microparticles may be used for local delivery of TPA in the affected area. In making microparticles or films/implants in situ, a multi-needle device with predefined/fixed distance between each needle may be used In one illustrative embodiment, a 5 needle device is used wherein each needle is separated by approximately 500-1000 microns. The multi-needle is used to deposit the injectable composition such PLGA solution in DMSO with Rifampin as a model drug in the skin or body. The well-defined distance between each injected droplet enables to undergo physical or chemical change such as precipitation in isolation. It is understood many changes in the illustrative embodiment may be made such changes are considered as part of this invention. The number of needles per device may vary from 5 to 10000. Each needle may be designed to inject at specific depth in the skin or body. The distance between each needle may vary depending on the desired outcome. A small distance between each needle may result into droplets with very close to each other and therefore may result into to fusion and film formation. A large distance between each needle may lead to formation of microparticles because fusion of injected droplets is not possible due to isolation of each injected droplet.

In one embodiment, the liquid compositions are injected in a manner such that they can be fused or coalesced together by a portion of each droplet merging with a portion of at least one adjacent droplet. Methods of fusing injected droplets together before physical or chemical transformation are described. 2 or more, preferably 10 or more, even more preferably 30 or more and even most preferably several hundred droplets may be fused together to create a larger droplet or a fused liquid mass in the tissue before undergoing physical or chemical transformation. The solvent in the fused mass dissipates in the surrounding tissue producing a polymer film or implant at the injection site. Preferably implant/film that is formed has area greater than 2 mm square and can have variety of shapes and sizes. The implant formed may be made using biostable polymers or biodegradable polymers.

In another embodiment, the injected liquid compositions are substantially prevented from fusing or coalescing together. The compositions are injected in such a manner that a portion of each droplet is substantially or completely prevented from merging with a portion of adjacent droplet. In general, during injection an effective gap is maintained between the two injected droplets so that the injected droplets cannot fuse or coalesce. The effective gap will depend on the droplet size and chemistry of the composition. Each injected droplet undergoes physical or chemical transformation in isolation from each other without partial or complete fusion with the neighboring injected droplet. The solvent in the individual droplet dissipates in the surrounding tissue producing a polymer microparticle in situ. The microparticles may be made using biostable polymers or biodegradable polymers.

In one embodiment, a composition includes PLGA 50:50, molecular weight 10000 as a biodegradable polymer (e.g., 10-30 day local release), Gentamycin is a generic well know antibiotic at 20 percent loading and Indocyanine green at 1-5 percent level as a water soluble FDA approved green colorant. Colorant and gentamycin can be encapsulated separately in separate microspheres or in the same microspheres. Both are entrapped in PLGA and cannot escape and both have high water solubility. Both are released in situ due to biodegradation/or diffusion mechanism. Indocyanine green being water soluble is immediately cleared by the tissue as it is released. Accordingly, the colorant can be a food dye.

Monomers, such as cyanoacrylates, can initiate polymerization when in contact with water or tissue fluids. Examples of such monomers include but not limited to ethyl cyanoacrylate, propyl cyanoacrylate, butyl cyanoacrylate and the like. Such monomers can also be deposited using methods described in this invention. The monomers can be deposited as a neat liquid or as a liquid solution and can be polymerized in situ to form microparticles. If needed such monomers may be added drug or visualization agent. Alternatively such monomers may be polymerized first as micro particles outside the body, with or without drug or visualization agent and such microparticles may be injected using compositions and methods described in this invention.

Hydrophobic biostable or biodegradable polymers that are generally easily precipitated in aqueous environment, preferably in physiological environment that is found inside the body or tissue are preferred for microparticle or film formation in situ using solvent dissipation method. Preferably such polymers have high molecular weight, generally higher than 2000 g/mole, preferably in the range of 10000-200000 g/mole. Information of polymer solubility can be found in the Polymer Handbook. Many hydrophobic polymers are known in the biomaterials art. Examples of hydrophobic polymers include but not limited to: polylacticacids; polycaprolactones; PLGA copolymers; polytrimethylene carbonate; polycaprolactone, polymathy methacrylate; polybutyl methacrylate; polycarbonate polyurethanes; polysilicone-polyurethanes and the like.

The following non-limiting examples are intended to illustrate the inventive concepts disclosed in this document. Those skilled in the art will appreciate that, in light of the teachings of the present invention, modifications can be made to these examples, drawings, illustrations and claims, which are contemplated to fall within the scope the present invention.

Materials and Methods

Tissues like bovine pericardium, porcine pericardium, porcine submucosa, porcine aortic root, porcine meniscus tissue, porcine cornea and bovine thoracic arterial tissue, bovine cornea are acquired or purchased from commercial sources such Animal Technologies, Tyler, Tex. or obtained from local abattoir or slaughter house. Submucosa tissue is obtained after cleaning and removal of tunica mucosa, muscular tissue and serous layers from the fresh porcine, sheep or bovine small or large intestinal tissue. Polyethylene glycol can be purchased form various sources such as, by way of example, and not limitation, Nektar Therapeutics (formerly Shearwater Polymers), Dow Chemicals (Union Carbide), Fluka and Polysciences. Various protein crosslinkers especially diacid or polyacid n-hydroxysuccinimide esters or n-hydroxysulfo- succinimide esters may be purchased form Sigma-Aldrich or Thermo Fisher Scientific (Pierce). Multifunctional hydroxyl and amine-terminated polyethylene glycol are purchased from Nektar Therapeutics, Dow Chemicals, Huntsman Corporation and Texaco. Amine-terminated polyethylene glycols also can be synthesized using methods known in the prior art or may be purchased from Aldrich (Jeffamine® ED-2003). PEG based monofunctional, difunctional, trifunctional, tetrafunctional and octafunctional NHS esters and other derivatives can also be purchased from commercial sources such as Creative PEGWorks, Winston Salem, N.C., USA; Laysan Bio, Inc. AL; Jenkem Technology USA, Allen, Tex., USA.; BOC Sciences, Shirley, N.Y. USA and Sigma Aldrich, USA. DL-lactide, glycolide, caprolactone and trimethylene carbonate can be obtained from commercial sources like Purac, DuPont, Polysciences, Aldrich, Fluka, Medisorb, Wako and Boehringer Ingelheim. N-hydroxysulfosuccinimide can be purchased from Pierce or Aldrich. All other reagents, solvents are of reagent grade and can be purchased from commercial sources such as, by way of example, and not limitation, Polysciences, Fluka, ICN, Aldrich and Sigma. Most of the reagents/solvents are purified/dried using standard laboratory procedures such as, by way of example, and not limitation, described by Perrin et al. Small laboratory equipment and medical supplies can be purchased from Fisher or Cole-Parmer. Cell culture experiments are performed using a standard mammalian tissue culture laboratory or microbiology laboratory capable of handling and growing mammalian and human cell cultures.

Shrink Temperature by Differential Scanning Calorimetry

Shrink temperature is evaluated by differential scanning calorimetry. Briefly, 10-20 mg of tissue sample is heated in a sealed aluminum sample pan and heated at 10 degree C. per minute up to 200 degree C. under nitrogen atmosphere. The onset of endotherm around 55 to 110 degree C. is attributed as shrink temperature.

Pepsin Digestion Assay-Gravimetric Analysis

In another assay, tissue samples of same size (⅝ inch dia) are cut and are incubated in 4 percent pepsin solution in 10 mM HCl at 37 degree C. for 48 h. At the end of 48 h, observations are noted if the tissue is completely digested, partially digested or completely intact. Untreated control tissue is generally completely digested in 48 h and glutaraldehyde fixed tissue generally stays completely intact in 48 h. The injected tissue samples may be digested using the procedure as described above to separate the microparticles for further analysis. Some microparticles, especially protein based hydrogels may not be able to tolerate the pepsin solution in HCl and therefore cannot be used.

Biodegradation and Biocompatibility of Tissue and Tissue-Biodegradable Polymer Composites In vitro degradation of the polymers is monitored gravimetrically at 37 degree C., in aqueous buffered medium such as, by way of example, and not limitation, phosphate buffered saline (pH 7.2). In vivo biocompatibility and degradation life times are assessed after subcutaneous implantation of tissue samples. The implant is surgically implanted in the animal body. The degradation of the implant over time is monitored gravimetrically or by chemical analysis. The biocompatibility of the implant is assessed by standard histological techniques.

General Analysis

Chemical analysis such as, by way of example, and not limitation, structural determination is done using nuclear magnetic resonance (proton and carbon-13) and infrared spectroscopy. High-pressure liquid chromatography or UV-visible spectrophotometry is used to determine drug elution profiles. Gel permeation chromatography is used for molecular weight determination. Thermal characterization such as, by way of example, and not limitation, melting point, shrink temperature and glass transition temperature is done by differential scanning calorimetric analysis. The aqueous solution properties such as, by way of example, and not limitation, self assembly, micelle formation, and gel formation are determined by fluorescence spectroscopy, UV-visible spectroscopy and laser light scattering instruments. Drug release studies are conducted in PBS under sink conditions at 37 degree C. and the drug elution is monitored by HPLC or UV-VIS spectrophotometer.

Example 1

Preparation of Biostable Tissue for Bioprosthesis Application

Example 1A

Crosslinking of Tissue Using Disuccinimidyl Glutarate or n-Hydroxysuccimide Ester of Glutaric Acid (DSG)

Fresh porcine pericardium tissue sac is obtained fresh from a local supplier. The tissue is cleaned to remove residual fat, blood and other matter. Five 2 cm by 2 cm pieces are cut and then used in subsequent crosslinking experiment. In a 15 ml glass vial, 200 mg of disuccinimidyl glutarate (DSG) is dissolved in 300 microliter dimethyl sulfoxide. After complete dissolution, 10 ml PBS (pH 7.2) is added to the DSG solution. The mixture is vigorously shaken for 5 minutes and the incubation continued at room temperature for 10 hours and then in refrigerator for 24 h. The tissue is taken out, washed with PBS several time and stored in cold 20-50 percent ethanol until further use. Untreated tissue stored in PBS is used as untreated control for comparison.

Example 1B

Tissue Crosslinking Using Glutaraldehyde

In a 250 ml glass beaker, 1 ml of 25 percent glutaraldehyde solution (25 percent stock solution from Sigma Aldrich) is mixed with 99 ml PBS. In two 50 ml beakers, 40 ml (0.25 percent in PBS, pH 7.2) glutaraldehyde solution is transferred. Twenty 2 cm by 2 cm porcine pericardium are transferred to one beaker. Twenty 5 cm by 5 cm pieces of submucosa tissue or natural sausage casing (porcine) are transferred to the other beaker and the solution is gently shaken. Both tissues are incubated at room temperature for 2 hours and then in refrigerator for 24 hours. The tissue is removed from the glutaraldehyde solution, washed with PBS for several times. The tissue may be lyophilized for further storage or may be stored in 25 percent ethanol or isopropanol until further use. Other small and larger sizes of tissue may be treated in same way, typically using excess of glutaraldehyde solution in PBS. Untreated tissue stored in PBS is used as untreated control for comparison.

In a similar procedure as above, disulfosuccinimidyl suberate (20 mg ml in PBS) is used as a crosslinking agent.

Briefly, 2 cm by 2 cm porcine pericardium tissues are incubated in disulfosuccinimidyl suberate solution (20 mg/ml PBS) at room temperature for 6 to 24 h. After 24 hours incubation, the treated tissue is washed with PBS several times and stored in 50 percent ethanol until use.

Example 2

Preparation of Biodegradable Tissue for Bioprosthesis

Tissues with Various Degradation Times In Vitro

Example 2A

Use of Uncrosslinked Tissue

Bovine pericardium tissue that is cleaned to remove blood, fat tissue and other cellular matter can be used. The tissue is washed and sterilized in 70 percent ethanol and used without additional treatment for fabrication of bioprosthesis.

Example 2B

Use of Uncrosslinked Decellularized Tissue

Five 1 cm dia circular tissue samples are cut from porcine pericardium tissue and transferred into 100 ml conical flask with stopper. 50 ml a 0.25% trypsin-EDTA solution in PBS is added in the flask for 30 minutes at 37 degree C. to loosen attached cells. The tissue is removed, washed with PBS and transferred into another flask containing 100 ml 20 percent sodium chloride solution and incubated for 24 hours followed by treatment with 100 ml 10% surfactant solution (Triton X-100) for 2 hours to remove cellular debris. The treated tissue is washed with distilled water, PBS and stored in 50 percent ethanol in refrigerator until used bioprosthesis manufacturer. The submucosa tissue is processed without crosslinking in a similar way as above. Literature procedure such as mentioned in U.S. Pat. No. 7,766,926 and cited references therein could also be used, cited herein for reference only, for making decellularized tissue.

Example 2C

Tissue Crosslinking of Tissue Using Zero Length Crosslinker

Tissue Crosslinking Using 1-Ethyl-3-3-Dimethylaminopropyl Carbodiimide-HCl (EDC)

In a 10 ml plastic centrifuge tube, 1 ml of HEPES or PBS buffer, pH 6 is added. To this solution 2 mg EDC and 1 mg n-hydroxysuccinimide (as a cocatalyst) is added. The mixture is stirred until complete dissolution. Ten 1 cm by 1 cm porcine pericardium pieces are added in the solution and the tube is cooled to zero degree in ice bath and maintained at ice temperature for 24 h. After 24 h, the tissue is washed with PBS several times and stored in 50 percent ethanol solution in water or 25 percent sodium chloride solution in refrigerator until further use.

Example 2D

Tissue Treatment Using Biodegradable Crosslinker

In a 250 ml glass beaker, 1 g PEG10K4ARM glutarate NHS ester purchased from commercial sources is dissolved in 10 ml PBS buffer. Ten 1 cm by 1 cm pieces of submucosa tissue or natural sausage casing (porcine) or porcine pericardium are transferred to the other beaker and the solution is gently shaken for 6 h. the tissue is removed and washed with PBS and stored.

The tissue takes longer time to digest in pepsin relative to untreated control indicating its improved stability in pepsin or in vivo relative to untreated tissue.

In a variation of above example, the PEG glutarate NHS ester may be changed to, PEG succinate NHS ester, PEG adipate NHS ester, PEG suberate NHS ester to obtain crosslinked tissue with various degradation time. The variation is hydrolysis rates of esters in crosslinking agents (succinate, glutarate, adipate, suberate) gives different degradation rates for the crosslinked tissue.

Example 3

Preparation of Biodegradable Colored Microparticles

Example 3A

Preparation of Colored and Radio-Opaque Microspheres

In a 500 beaker with magnetic stirrer, 200 mg F D and C Green number 6, 3 g Iopamidol, 7 g polylactide-co-polyglycolide copolymer (PLGA, 50:50; inherent viscosity 0.76) are dissolved/suspended in 100 ml dimethyl sulfoxide for 48 hours. The solution is warmed if necessary. The dimethyl sulfoxide solution is concentrated under vacuum and air dried to form a polymer film. The polymer film is cooled using liquid nitrogen and pulverized to make microparticles. The microparticles are sieved and the sieved fractions are used in future experiment. The microparticles appeared green to the necked eye due to presence of F D and C Green number 6. The presence of Iopamidol provides x-ray visibility presumably due to organic bound iodine. Using a similar procedure mentioned above, the Iopamidol concentration the microspheres is varied from 3 to 60 percent to provide varying degree of radio-opacity to the microparticles.

Example 3B

Colored Particles from Colored Biodegradable Materials

In a modification of above methods, colored biodegradable sutures such as Vicryl 910 Ethicon (synthetic absorbable polymer) or yellow catgut sutures (tissue based absorbable material) are used. About 1 g of both materials are cooled in a liquid nitrogen and cryogenically ground and sieved to obtain a suitable particle size fraction. Since the sutures are already colored, the resultant particles are colored in nature.

Example 3C

Preparation of Colored Biodegradable Microparticles by Spray Drying 0.9 g Poly(lactic-co-glycolic acid) (50:50) and 0.1 g F D and C green number 6 are dissolved in 10 ml dichloromethane. The mixture is sprayed using a standard air pressure spry gun and the sprayed droplets are collected in 1000 ml liquid nitrogen. The liquid nitrogen is evaporated and the frozen droplets are warmed in cold dimethyl ether solution (temperature below 0° C.) in such a manner that only solvent (dichloromethane) is extracted out in the ether solution. The microspheres are collected by filtration using 0.45 micron glass filter. The microspheres are dried in vacuum oven for 24 hours at ambient temperature. The microspheres appeared dark green colored, which can be easily distinguished in the blood/tissue environment.

Dyes like F and D dyes such as FD and C blue No 3, FD and C green No 6, eosin, ethyl eosin, Rose Bengal, erythrosine and the like may be added to prepare other colored biodegradable materials. The dye may be added from 0.1% to 20% weight/weight basis. The most preferred amount dye added is 0.1% to 5% w/w basis.

Example 3-D

Coloring by Staining the Microspheres 75 microns size polylactic acid-co-polyglycolic acid copolymer (50:50 lactic:glycolic) microspheres are purchased from Polysciences Inc., USA. In 20 ml glass vial, 50 mg ethyl eosin and 10 g ethanol are added and the solution is mixed until ethyl eosin dissolves in ethanol solution. 1 g of the microspheres are incubated ethanol solution for 24 h. Ethanol solution is removed and the microspheres are washed with water to remove loose dye. The red colored stained microspheres are used as biodegradable colored microspheres. In a similar experiment, 1 g microspheres are added to 5 percent solution/suspension of turmeric in water. The microspheres are incubated in water for 12 h and are removed and washed with distilled water to remove loose turmeric particles. The yellow colored particles are used as colored biodegradable microspheres.

Example 4

Biodegradable Microparticles with Drugs

Example 4A

Solvent Evaporation Method for Preparation of Microspheres

Approximately 100 mg rifampin or gentamycin, 900 mg of PLGA (50:50 lactide:glycolide 60000 g/mole) are dissolved in 7 mL of methylene chloride homogenous solution. Separately in a 1 L beaker, 6 g or polyvinyl alcohol (40000-50000 g/mol, 90 percent hydrolyzed) is dissolved in 300 ml distilled water. The drug solution is transferred to 10 ml glass syringe with 25-gauge needle and added polyvinyl alcohol solution while stirring vigorously using a magnetic stir bar. The solution is added over a 20-30 second period. The stirring continued for 24 h to remove methylene chloride. The microspheres are filtered, washed with distilled water several times and then vacuum dried for 48 h. If rifampin, the microspheres show mild yellow red color; if gentamycin is used, no color is visible. The mixing conditions and polymer concentration are changed to obtain a desired particle size.

Example 4B

Drug Encapsulated Microspheres by Emulsion Method 1.5 g of rifampin is dissolved in 1 ml distilled water containing 10 mg of bovine serum albumin. The resultant aqueous solution is added to 30 ml methylene chloride containing 3.5 grams of Polylactide-co-polyglycolide (50:50) and then emulsified by a brief sonification for 30 seconds. The water-in-oil (W/O) emulsion is reemulsified in 2000 ml 0.1% (w/v) polyvinyl alcohol (PVA) with stirring for 3 h at room temperature. The hardened microspheres are washed three times with water to remove unencapsulated rifampin. The microspheres are recovered by centrifugation and freeze-drying. The residual solvent is removed by drying the microspheres in vacuum oven at 37° C. for 48 h.

Example 4C

Preparation Drug Encapsulated Microspheres by Spray Drying Method

Biodegradable poly(lactic-co-glycolic acid) (PLGA, Boehringer Ingelheim, Germany, Type RG 502 H) based microspheres are prepared by a spray-dry method using dichloromethane as the solvent. In this method, drug such as rifampin or gentamycin and biodegradable polymer are dissolved in a low boiling solvent such as dichloromethane. Briefly, 4 g PLGA and 1 g gentamycin are dissolved in 40 ml dichloromethane. The mixture is then sprayed in a spry drying apparatus where solvent is rapidly evaporated and the resultant polymer particles are collected. Following parameters of the spray-dry process may be used: a) air temperature 45 degree C.; air flow 600 NLQ/h and 3 mL/min liquid infusion rate. The microparticles are collected, washed with water, dried under vacuum for 24 hours at ambient temperature. The size and size distribution of the microspheres is determined using low angle laser light scattering.

Example 4D

Preparation Drug Encapsulated Microspheres by Freeze Drying Method 0.7 g Poly(lactic-co-glycolic acid) (50:50) and 0.3 g gentamycin or rifampin are dissolved in 10 ml dichloromethane. The mixture is sprayed using a standard air pressure spry gun or using a fine needle syringe and the sprayed droplets are collected in 1000 ml liquid nitrogen. The liquid nitrogen is evaporated and the frozen droplets are warmed in cold dimethyl ether or methanol solution (temperature below −20-0° C.) in such a manner that only solvent (dichloromethane) is extracted out in the water or methanol or ether solution. The microspheres are collected by filtration using 0.45 micron glass filter. The microspheres are dried in vacuum oven for 24 hours at ambient temperature. The rifampin has red natural color therefore this preparation serves as biodegradable particles with color and drug in same composition.

Example 4E

Preparation Drug Encapsulated Microspheres by Melt Method

A low melting (melting point <80° C.) polyanhydride based biodegradable polymer is obtained by condensation polymerization of sebacic acid dianhydride and fatty acid based dianhydride. Alternatively, polycaprolactone may also be used as low melting polymer. 8 g polycaprolactone (low molecular weight, mol wt. around 2000 g/mole), 2 g rifampin and 100 ml dichloromethane are mixed in a 500 beaker until rifampin is completely dissolved or dispersed. The mixture is precipitated in 2000 ml cold hexane to precipitate the rifampin/polycaprolactone mixture. The precipitate is filtered and dried under vacuum until constant weight. The dried mixture is transferred to 1000 ml flask containing 300 ml silicone oil and mechanical stirrer. The silicone oil is heated to 60-90° C. The rifampin/Polycaprolactone mixture is added to the hot oil while stirring vigorously. If necessary, sonification may be used to obtain a fine suspension of melted polymer in the silicone oil. While stirring, the mixture is cooled to zero degree C. using ice bath and stirred at room temperature for 24 h. The solidified microspheres of drug/Polycaprolactone are separated by filtration. The silicone oil is washed using cold methanol.

Example 4F

Preparation of Low Water Soluble Colored Drugs Particles (Solubility Less than Five Percent in Water) for Drug Delivery 5 g chlorhexidine diacetate salt hydrate (Sigma C6143) or 5 g chlorhexidine gluconate is hand pulverized using laboratory mortar and pestle. The pulverized powder is sieved and only fine powder fraction is used in drug delivery application. The drug suspension may be incubated for 1 hour in one percent Eosin Y solution in PBS or one-three percent turmeric solution/suspension water to stain the particles red or yellow respectively. The colored stained particles are easy to visualize when infused in dermis using tattoo like machines. Other drugs such as paclitaxel may be colored using the same methods as descried above. Alternatively, color may be added in polymeric carrier such as collagen or gelatin and the coating may be applied on drug crystals.

Example 5

Preparation of Colored and Drug Encapsulated Microspheres

In a 50 ml polypropylene tube, 0.3 g bovine serum albumin is dissolved in 10 ml distilled water. In 100 ml round bottom flask with magnetic stirrer, 1 g polylactide-co-polyglycolide copolymer (PLGA 50:50, inherent viscosity 0.76, purchased from Alkermes Inc., Wilmington Ohio) and 100 mg Rifampin are dissolved in 10 ml dichloromethane. The solution is cooled to 0° C. over ice bath and albumin solution is added to the PLGA solution. The solution is emulsified using a 15 W sonicate probe for 20 seconds to form water in oil emulsion. The emulsion is gradually added to 250 ml aqueous 3% polyvinyl alcohol solution under constant stirring or sonication. The solution is stirred for 6 hours at ambient temperature to evaporate dichloromethane. After substantial evaporation, the solution is centrifuged to isolate the microspheres. Resultant microspheres are recovered, washed with cold distilled water 2 times and dried under vacuum until constant weight. Since rifampin has mild red yellow color, the drug serves as a colorant.

Example 6

Hydrogel Based Biodegradable Polymers

Protein Based Colored Biodegradable Microspheres 0.2 g gelatin was dissolved in 1.8 ml 0.1M MES buffer, PH 5.5. To this solution, 100 mg eosin Y, 0.3 g n-hydroxysuccinimide and 0.3 g EDC were added. After complete dissolution, the mixture is added to 100 ml mineral oil and the stirred vigorously. The crosslinking reaction and stirring was continued for 12 hours. The gelatin microspheres were separated by filtration and washed with hexane to remove traces of mineral oil. The eosin stains as well as covalent links to the albumin. Using a similar procedure, fluorescein (free acid form) can be chemically bound to the gelatin to make it fluorescent.

Example 7

Colored Thermosensitive Compositions with Drug for Injection 100 mg of gentamycin, 3 g Pluronic and 10 mg of F D and C blue or Eosin Y as a colorant and 4 g of PBS buffer (pH 7.2) are mixed in a glass vial. The vial is kept on ice (zero degree C.) as Pluronic F127 is soluble in cold (0-15 degree C.) water. The colored solution when warmed to 37 degree C. becomes a gel, which forms a fluid solution when cooled again between 0-15 degree C. This colored solution with thermosensitive properties is used as colored thermosensitive composition for infusing drug in the tissue.

Example 8

Preparation of Hydrogel Based Biodegradable Microspheres with Drugs 1 g bovine albumin is dissolved in 3 ml PBS. To this solution 100 mg of chlorhexidine is added. The solution/suspension is stirred and transferred to 10 ml syringe with 22 gauge needle. The albumin solution is dispensed from the syringe or sprayed from a sprayer into a 1000 ml liquid nitrogen. The frozen droplets are collected. Liquid nitrogen is evaporated. The frozen microspheres are exposed to 0.25 percent glutaraldehyde solution at zero degree C. for 30 minutes in PBS pH 7.2 to crosslink albumin. The crosslinked microspheres are washed with PBS 3 times and then lyophilized. The crosslinked hydrogel microspheres may be vacuum dried at room temperature to dehydrate them. The dehydrated microspheres can have smaller size or more relative to its hydrated size and can regain the original size by abortion of water. In a modification of above procedure, the albumin is crosslinked with 20 mg/ml in PBS pH 7.2 disulfosuccinimidyl suberate for 12 h.

In a similar experiment, chlorhexidine is replaced by 100 mg rifampin to make rifampin loaded colored microspheres.

Example 9

Injection of Microparticles into Bioprosthetic Tissue

Injection Using Oscillating/Pulsating Needle Machine

Injection Using Tattoo Machine

Injecting Colored Microparticles/Microspheres in the Bioprosthetic Tissue

Example 7A

Injecting Colored Biodegradable Microparticles with Drug in a Bioprosthetic Surgical Patch In one exemplary embodiment, 1 g of rifampin-loaded microspheres or other drug-loaded microspheres colored microspheres (particle size below 300 microns) are suspended 2-10 ml 30 percent glycerine solution. A commerically available tattoo machine with oscillating needle is used. The machine is set up according to instructions provided by the manufacturer. The machine is attached with #12 size needle. The machine is turned on and the voltage of the power supply for the oscillating coils is set between 8.0 and 9.0 volt (at this voltage, the needle oscillates between 50-200 times per second). 4 inch by 4 inch 1-2 mm thick bovine pericardium (glutaraldehyde fixed) is placed on a flat surface on top of a rubber pad for support. A small amount of lubricant grease (for reducing needle frication) is applied on the 2 cm by 2 cm area at the center. The tattoo machine is needle is dipped in the drug suspension and foot paddle of the machine, which can turn the power to the electric coil, is pressed to supply powder to the machine. The oscillating needle is kept about 1 mm distance from the tissue surface. The oscillating needle is slowly moved to draw 1 cm diameter circle on the tissue. The needle penetration is adjusted in such a way that the drug particles are deposited about 10 to 1000 micron dip from the surface and can be visually seen. The needle is dipped in the rifampin suspension several times to resupply the drug for infusion. As the needle moves, a red line is seen on the tissue surface (drug loaded particles has red color and pericardium is off whit in color). The color helps to visually control the deposition of particles in the tissue. After the circle is drawn, the excess drug suspension is wiped out from the tissue surface. The infused particles are visible and cannot be wiped away. Infused surface is washed with PBS. The particles cannot be removed by wiping or washing indicating that they are embedded in the tissue. The tattooed area of the tissue is cut and is incubated in 3 ml PBS for 60 days. The drug release from the tissue is monitored at 1 h, 3 h, 12 h, 24 h, 2 day, 5 day, 7 days, 14 day 28 day time period. PBS is changed at every time point. The eluted drug is monitored by UV-VIS spectrophotometer or HPLC. In an identical experiment as above, a standard tattoo ink is used as a control and the release from control is also monitored. As expected the tattoo ink sample does not show drug release.

In a modification of above experiment, vitamin E acetate oil with 2 percent rifampin is used as a tattoo ink. The vitamin E deposits and stay trapped in the tissue fibers as oil droplet along with the drug. Thus a liquid carrier can successfully be used to infuse in the tissue surface.

In another modification, chlorhexidine acetate suspension colored yellow due to yellow stain is used to infuse the suspension in the tissue matrix. The drug has low solubility in water and does not require a carrier. The drug slowly dissolves in water and is released as a result of dissolution. The staining of drug helps to visualize the placement of the drug.

A blue or red thermosensitive composition prepared per Example 7 is used in tissue, preferably a live tissue. The thermosensitive composition is kept at 0-10 degree C. during the use. The oscillating needle of the tattoo machine is filled with cold composition as described in Example 7 and then injected in bovine pericardium tissue maintained at 37 degree C. simulating human tissue. The composition is deposited and the drops of the deposited composition undergo thermosensitive gelation and form a gel particle inside the tissue. The gel particle releases drug over a period of time.

Example 10

In Vivo Deposition of Colored Composition Using Oscillating Needle

Briefly, a rat is anesthetized and its peritoneal cavity is opened surgically. On the peritoneal wall 5 mm by 4 mm area is infused with the colored rifampin encapsulated drug particles at a depth of 10 to 500 microns using the sterile tattoo machine needle as described before. After infusion, the excess drug fluid is wiped/washed off and the animal is closed. The deposition of ink is successfully achieved in a live animal during an experimental surgical procedure.

Example 11A

Delivery of Injectable Synthetic Biodegradable Polymer Solution Using Oscillating Needle Device Formation of In Situ Biodegradable Microparticles in the Live Tissue or Bioprosthesis Tissue Part 1: Preparation of Sterile Injectable Synthetic Biodegradable Polymer Solution with Drugs Suitable for Injection in the Live Tissue. Use of Water Miscible Organic Solvent In a 50 ml glass beaker, 20 ml dimethyl sulfoxide, 1.8 g Poly (PLGA, polylactide-co-glycolide) (lactide:glycolide (50:50), molecular weight 30000 to 60000 g/mole.) and 200 mg (approx. 10 percent loading relative to weight of the polymer) gentamycin and 20 mg of eosin Y as a colorant are mixed until homogeneous solution. The solution in the beaker is sterile filtered (filter has PTFE membrane and polypropylene housing which is not affected by the DMSO solvent). The sterile filtered solution is used as a tattoo ink for the tattoo machine.

Part 2: In Situ Delivery of the Polymer Drug Solution Using Oscillating Needle

About 2 cm by 2 cm portion rat back skin is shaved to remove hairs. Iodine solution is applied to sterilize the area. Sterile filtered vitamin E acetate oil is applied on the shaved skin area, which acts as a lubricant for the tattoo needle. Alternatively Redemption™ tattoo lubricant may also be used. A new sterile tattoo needle is attached on the tattoo machine. The machine is powered (needle oscillation started). The oscillating needle is dipped inside the sterile gentamycin solution, which fills the hollow needle tip, and the needle is used to draw two 1 cm tattoo lines crossing at right angles (plus sign shape). Excessive solution is wiped of from the skin. The DMSO in the injected liquid is dispersed/dissipated by the fluids in the skin tissue leaving behind PLGA polymer microparticles with gentamycin and eosin trapped (precipitation of PLGA polymer by water in the tissue). The PLGA polymer deposited under the skin tissue provides sustained delivery of gentamycin.

Bovine pericardium tissue (5 cm by 5 cm) is procured freshly and is decellularized as mentioned previously. The tissue is incubated for 24 hours in PBS to hydrate it completely. The pericardial tissue can be considered as exemplary surgical bioprosthesis patch or wound dressing. The sterile gentamycin solution is injected in the bovine pericardium tissue and tattooed two 1 cm crossing lines. After the injection, free solution on the tissue surface is wiped of. The tissue is incubated in PBS for 2 h. The water in the tissue precipitates the injected droplets entrapping the drug inside the precipitated PLGA. Eosin provides color, which helps during injection/tattooing. The infused portion is clearly visible on the white tissue background. The infused section is observed under scanning electron microscope and regular microscope to confirm the presence of polymer particles. The infused tissue section is cut from the tissue and sent for histology analysis to confirm the formation of microparticles. In another experiment the infused section is cut from the tissue is incubated in 10 ml PBS at 37 degree C. Fresh 10 ml PBS is exchanged at following time intervals: 30 minutes, 60 minutes, 12 h, 24 h, 2 day, 3 day, 5 day, 7 day, 14 day, 28 day time period. The drug eluted sample are protected from light and stored in refrigerator until HPLC analysis. The eluted gentamycin in PBS solution is analyzed using HPLC.

In another modification of this embodiment, 20 ml dimethyl sulfoxide, 1.4 g Poly (PLGA, lactide-co-glycolide) (lactide:glycolide (50:50), molecular weight 30000 to 60000 g/mole.) and 600 mg (approx. 30 percent loading relative to weight of the polymer) gentamycin is used and the solution is infused in pericardial tissue. The infused drug is eluted in PBS as mentioned above and is analyzed using UV visible spectrophotometer or HPLC.

In another modification of this embodiment, 20 ml dimethyl sulfoxide, 1.8 g polycaprolactone (molecular weight 70,000-90,000 g/mole.) and 200 mg (approx. 10 percent loading relative to weight of the polymer) rifampin is used and the solution is infused using oscillating needle in the pericardial tissue. The infused drug is eluted in PBS as mentioned above and is analyzed using UV visible spectrophotometer.

In another modification of above examples, gentamycin is replaced with rifampin, chlorhexidine diacetate salt hydrate. In another modification, gentamycin in the above examples is replaced with coumarin 6 a fluorescent additive and model drug.

Example 11B

Delivery of Injectable Synthetic Biodegradable Polymer Solution Using Oscillating Needle Device Formation of In Situ Biodegradable Microparticles in the Live Tissue Part 1: Synthesis of Polyethylene Oxide (PEO)-Polypropylene Oxide (PPO)-Polyethylene Oxide Lactate Copolymer (PEO-PPO-PEO Lactate Copolymer)

20 g of Pluronic F127 (PEO-PPO-PEO block copolymer) is dried under vacuum at 100 degree C. for 24 h. 20 g of dry Pluronic F127, 4.61 g of dl-lactide and 30 mg of stannous octoate are charged into 100 ml Pyrex pressure sealing tube. The tube is then connected to argon gas line and sealed under argon. The tube is then immersed in oil bath maintained at 140 degree C. and the reaction is carried out for 16 h at 140 degree C. The polymer from the tube is recovered by breaking the Pyrex tube. The polymer is then dissolved in 100 ml chloroform and precipitated in 2000 ml cold hexane or ether. The precipitated polymer is recovered by filtration and dried under vacuum for 1 day at 60 Degrees C.

Part 2: Injection of PEG Copolymer (PEO-PPO-PEO Lactate Copolymer) in the Prosthetic Tissue Using Oscillating Needle Device In a 50 ml beaker, 20 ml n-methylpyrrolidinone, 1.8 g PEO-PPO-PEO lactate copolymer and 200 mg (approx. 10 percent loading relative to weight of the polymer) rifampin are added until solution is formed. The solution is sterile filtered using PTFE based filter in a clean sterile polypropylene tube. A tattoo machine needle is dipped in the solution and the needle is used to tattoo the pericardial tissue (1 cm dia circle shape is drawn using the tattoo needle). The infused drug is eluted in PBS as mentioned above and is analyzed using UV visible spectrophotometer.

In another modification of above example in Part 1, 20 g of polyethylene glycol (molecular weight 20000) g/mole is reacted with 14.4 g lactide and 30 mg stannous octoate are reacted at 140 degree C. for 16 h to produce PEG-polylactide high molecular weight polymer (molecular weight 30000 to 40000 g/mole). A 10 percent of this polymer solution in acetone is used for infusion with tattoo machine.

In another embodiment of above example in Part 1, 2.00 g polyethylene glycol (molecular weight 2000 g/mole), 7.2 g of dl-lactide, 5.7 g caprolactone and 30 mg of stannous octoate are reacted at 140 degree C. for 16 h to produce PEG-co-polylactide-co-polycaprolactone copolymer. A 10 percent of this polymer solution in DMSO is used for infusion using oscillating needle in part 2.

The molar ratio of cyclic lactone and hydroxy groups in the PEG or Pluronic polymers is used to control the molecular weight (degree of polymerization) in the copolymer. The PEG-polylactone ratio may be changed 5-90 percent to obtain polymers with wide range of properties including thermoreversible properties.

In another modification of above examples, rifampin is replaced with gentamycin, chlorhexidine diacetate salt hydrate. In another modification, rifampin in the above examples is replaced with coumarin 6 as a fluorescent additive and model drug.

Example 11C

Delivery of Injectable Synthetic Biodegradable Polymer Solution Using Oscillating Needle Device Delivery of Water Soluble Synthetic Biodegradable Polymer Part 1: Synthesis of Water Soluble Polyethylene Glycol Lactate Copolymer (PEG-Polylactate-10)

In a 500 ml flask, 20.0 g of PEG 10000 (molecular weight 10000 g/mole), and 200 ml toluene is added. Approximately 80-100 ml toluene is distilled of and the solution is cooled. 5.4 g of dl-lactide and 30 mg of stannous octoate are added in the flask and the solution is refluxed for 24 h under nitrogen atmosphere. The flask is cooled and the solution is precipitated in 2000 ml cold hexane or ether. The precipitated polymer (PEG-LACTATE-10) is recovered by filtration and dried under vacuum for 1 day at 60 degree C.

Part 2: Injection of PEG Copolymer Lactate Copolymer (PEG-Polylactate-10) in the Tissue Using Oscillating Needle Device In a 50 ml beaker, 6 ml PBS, 2.0 g (PEG-polylactate-10) and 100 mg (approx. 5 percent loading relative to weight of the polymer) rifampin are added until complete solution. The solution is sterile filtered using PTFE based filter in a clean sterile polypropylene tube. A tattoo machine needle is dipped in the solution and the needle is used to tattoo the pericardial tissue (1 cm dia circle shape is drawn using the tattoo needle). The concentration of polymer in PBS is above its critical micelle concentration and therefore forms micelles in PBS, which can entrap hydrophobic drugs. The drugs in the micelles are released in a sustained manner. This example can be treated as micellar drug delivery system wherein drug is incorporated in the micelles and the micelles are then injected using oscillating needle in the tissue. Each micelle can be considered as nano size drug loaded microparticle.

In another modification, rifampin in the above examples is replaced with coumarin 6 as a fluorescent additive and model drug.

Example 12A

Delivery of In Situ Forming Crosslinkable Compositions Using Oscillating Needle Device Delivery of Composition that Crosslink Using Free Radical Polymerization Part 1: Synthesis of Polyethylene Glycol Lactate Copolymer In a 500 ml flask, 20.0 g of PEG 10000 (molecular weight 10000 g/mole), and 200 ml toluene is added. Approximately 80-100 ml toluene is distilled of and the solution is cooled.

2.68 g of dl-lactide and 30 mg of stannous octoate are added in the flask and the solution is refluxed for 24 h under nitrogen atmosphere. The flask is cooled and the solution is and precipitated in 2000 ml cold hexane or ether. The precipitated polymer (PEG-LACTATE-5) is recovered by filtration and dried under vacuum for 1 day at 60 degree C. It then immediately used in next reaction.

Part 2: End-Capping of PEG-LACTATE-5 with Polymerizable or Crosslinkable Group (PEG-LACTATE-5-Acrylate)

In a 500 ml reaction flask, 20 g of PEG-LACTATE-5 is dissolved in 300 ml dry toluene. About 50 ml of toluene is distilled out to remove traces of water from the reaction mixture. The warm solution is cooled to room temperature. 0.39 g of triethyl amine and 0.34 g acryloyl chloride are added. The reaction mixture is then stirred for 6 h at 50-60 degree C. and filtered. PEG-LACTATE-5-acrylate macromonomer is precipitated by adding the filtrate to 2000 ml cold hexane or ether. The precipitated polymer is recovered by filtration. It is then dried under vacuum for 12 h at 50 degree C.

Part 3: Polymerization and Crosslinking of Deposited Droplets

Separately 3 g of PEG-LACTATE-5-acrylate diacrylate prepared as above is dissolved in 9 g PBS. 300 mg Irgacure 2959 is dissolved in 700 mg n-vinyl pyrrolidinone. 50 microliter of Irgacure 2959 solution is added to the PEG-LACTATE-5-acrylate solution and 100 mg heparin as model water soluble drug is added to the solution. The solution is sterile filtered using 0.2 micron filter. The sterile solution (precursor solution) is filled inside an oscillating tattoo needle and the solution is injected inside a pericardial tissue or live skin tissue using oscillating needle of tattoo machine. The infused solution used then exposed to the long UV ultraviolet light (Black-Ray UV lamp, 360 nm light, 10000 mW/cm2 intensity) for 5 minutes to photopolymerize and crosslink the infused precursor solution in the tissue. The PEG-LACTATE-5-acrylate polymerizes and crosslinks to form biodegradable hydrogel particles. The entrapped hydrogel release the drug in sustained manner. The UV exposure may also be done using during infusion. The solution infusion is done at 10 to 30 micron depth as long UV light has low penetration in the tissue.

In another modification as above a visible light photopolymerization is used to crosslink the injected precursor solution droplets. In 100 ml beaker 3 g of PEG-LACTATE-5-acrylate diacrylate prepared as above is dissolved in 9 g PBS. In another 10 ml glass vial, 300 mg eosin Y is dissolved in 700 mg n-vinyl pyrrolidinone. 30 microliter of eosin y solution, 1 ml of 5 M triethanol amine in PBS are added to PEG-LACTATE-5-acrylate solution and the solution sterile filtered and protected from light using aluminum foil. The precursor solution is infused in the pericardial tissue using a tattoo machine like oscillating needle at a depth of 10-1000 microns. The infused solution droplets are crosslinked by photopolymerization by exposing it to 512 nm laser (argon laser) light or high intensity white floodlight. In some cases, the light may be used while infusion process is being done (the solution is the tattoo needle is protected by light.). The light polymerizes and crosslinks the PEG-LACTATE-5-acrylate monomer and forms gel particles in situ at the injection site.

In another modification of above embodiment, 100 mg tissue plasminogen activator (TPA) is added as an exemplary drug along with eosin solution. The TPA is entrapped in a hydrogel particle and is then released in a sustained manner when the crosslinked PEG-LACTATE-5-acrylate degrades in vivo.

Example 12B

Delivery of In Situ Forming Crosslinkable Compositions Using Oscillating Needle Device Delivery of Composition that Crosslink Using Condensation Polymerization 500 mg PEG10KARM glutarate NHS ester obtained from commercial sources; (Laysan Bio Inc., Arab, Ala.) is dissolved in 9.5 ml PBS (20 mM pH 7.2) until complete dissolution (precursor A solution). 1 g albumin and 10 mg methylene blue is dissolved in 9 ml PBS (precursor B solution). Both precursor solutions are sterile filtered. 1 ml of PEG10KARM glutarate NHS ester and 1 ml albumin are mixed. The gel time for this solution is about 20-180 seconds. The solution is infused into pericardial tissue surface using an oscillating tattoo needle of a tattoo machine. The infusion is done quickly before gelation occurs. If the solution gels before the infusion, a new solution is made and used. Alternatively, the solutions can be mixed in the modified tattoo machine device in a mixing chamber that is attached to a tattoo machine. The mixing chamber solution is infused in the tissue. The liquid infused precursor mixture undergoes condensation polymerization and crosslinking (total reactive functional groups in the precursors must be greater than 5 and each precursor must have greater than 2 functional groups) and forms gel particles at the injection site. If the precursors are loaded with drug, the drug is released in sustained manner. The drug should not have functional group capable of reacting with precursors under crosslinking conditions.

In another embodiment, PEG10KARM glutarate NHS ester and trilysine are mixed in molar equivalent quantities. The gel time of the precursors are adjusted using various buffers that provide pH 6 to 8 range. In general acidic pH are preferred. Some of the formulations gels in few seconds and therefore may be preferentially used by mixing in situ inside the device before injecting in the tissue or mixed just after exiting the needle if delivered using multilumen needle.

Another modification of above example, albumin is replaced with gelatin or collagen solution (1-5 percent in PBS or 0.1 M acetic acid) to form a crosslinked gelatin or collagen gels.

Example 12C

Delivery of In Situ Forming Crosslinkable Compositions Using Oscillating Needle Device Delivery of Composition that Crosslink Via Enzymatic Pathway Formation of Fibrin Gels Particles In Situ A commercially available EVICEL® from Ethicon or TISSEEL from Baxter may be used. The components of fibrin glue (fibrinogen, thrombin, factor 8, calcium ions and the like) are supplied as a two component mixture. The components of commercially available fibrin sealant are mixed in a sterile cup (total volume of mixed components 1-2 ml). To this solution 5 drops ophthalmic sodium fluorscein solution are added or 10 mg of indocyanine green dye added as a fluorescent/coloring agent or coloring agent. If no color is desired, the formulation can be used without the use of coloring agent or dye. The colored fibrin formulation is then loaded in the oscillating needle of the tattoo machine and injected (tattooed) into pericardial tissue or in live skin tissue.

The excess solution on the tissue surface is wiped of. The injected solution droplets undergo enzymatic polymerization/crosslinking and form fibrin glue/gel particles in situ inside the tissue. Care is taken to inject the formulation before the fibrin glue forms gel (usually 1-2 minutes). If components prematurely gel, then a new mixture is prepared and used quickly. The fibrinogen solution may be diluted using PBS to slow the gelation process. Alternatively a modified tattoo machine like device is used wherein the components are mixed inside the device just prior to injection and injected by an oscillating needle. The colorant or fluorescence of particles or droplets provides visual clue on the amount of injected solution at each injection site. A drug may be added to the composition. Drugs that interfere with the fibrin glue formation such as TPA or heparin cannot be used for local delivery using this method. Many drugs can be used with fibrin glue system. Live cell suspensions may be added to the fibrin glue components to deliver live cell based compositions. A multilumen needle may be used to deliver fibrin glue precursors (one lumen for fibrinogen solution) and another lumen for thrombin solution. The components are injected simultaneously and crosslinked in situ.

Example 13

In Situ Formation of Water Insoluble Drug Salts Using Oscillating Needle Device

Delivery of Water Insoluble Drugs in Water-Miscible Biocompatible Solvents Using Oscillating Device In a 50 ml glass baker, 1 g of chlorhexidine diacetate salt hydrate and 10 mg ethyl eosin or methylene blue as a colorant is dissolved in 20 ml ethanol. The solution is sterile filtered. The solution is deposited in the pericardial tissue patch or inside live tissue using a tattoo machine and oscillating needle apparatus. Briefly, a new sterile tattoo needle is attached to the tattoo machine and the machine is started/powered. The oscillating needle of the tattoo machine is dipped in the chlorhexidine diacetate solution. The needle sucks up the liquid. The needle with the solution is then used to deposit the solution in the tissue layers (dermis layer). The infused solution droplets disperse/dissipate ethanol in the tissue and deposits of chlorhexidine diacetate are formed (solubility of chlorhexidine diacetate is around 1.9 percent in water and 5-6 percent in ethanol). The deposited chlorhexidine diacetate crystals dissolve over a period or 1 to 10 days depending on the amount deposited and the implantation site. The release chlorhexidine provides antimicrobial local effect.

In another variation of above embodiment, 10 mg of paclitaxel, an anticancer drug is dissolved in 10 ml dimethyl sulfoxide or ethanol along with 10 mg of methylene blue or ethyl eosin or turmeric as a colorant. The DMSO solution is injected in the pericardial tissue or dermis layer of live tissue using oscillating needle as described above. Upon deposition, and dissipation of DMSO or ethanol by the tissue, paclitaxel crystals are deposited inside the tissue (solubility of paclitaxel is around 0.1 mg/ml or less in water or PBS). The deposited crystals release the drug by slow dissolution of drug crystals providing therapeutic local effect. The paclitaxel drug can be useful for local delivery of anticancer drug in or around the cancerous tissue during an open or MIS cancer surgery. In another modification of the above example, the DMSO or ethanol solution (1 mg/ml concentration) is deposited in the arterial tissue immediately after balloon angioplasty or plaque excision technology. The deposition is done using a modified version of a tattoo machine apparatus that is suitable to be used in a MIS surgical or catheter based device or technique. The modified oscillating needle apparatus is inserted in the catheter delivery system and transported at a local (balloon angioplasty site) site and deliver the drug using oscillating needle in the disease area to prevent restenosis. The needle is moved around the tissue to cover balloon angioplasty affected area. The deposited solution disperses DSMO or ethanol and deposit paclitaxel crystal in the arterial tissue. The entrapped crystals slowly release the drug providing anti-restenosis effect. Other anti-restenosis drugs such as Rapamycin, Everolimus, Atrovastatin or their derivatives or analogs and the like or may also be used for local anti-restenosis effect.

Example 14

Delivery of Thermosensitive Compositions Using Oscillating Needle Device

Delivery of Water Insoluble Drugs in Water Miscible Solvents

In a 250 ml glass beaker, 20 g of Pluronic F127 and 0.5 g of chlorhexidine acetate and 10 mg of methylene blue is dissolved is 40 g cold PBS solution (0-10 degree C.). The F127 is a PEO-PPO-PEO block copolymer that has thermoreversible gelation properties. The polymer solution is sterile filtered (temperature held at 0-10 degree C. during filtration). The cold solution is used for deposition with oscillating needle device (tattoo machine as an illustrative example). The solution is kept cold using an ice bath to maintain its fluid state. The solution is deposited in the pericardial tissue patch or lives tissue using a tattoo machine and oscillating tattoo needle. Briefly, a new sterile tattoo needle is attached to the tattoo machine and the machine is started/powered. The oscillating needle of the tattoo machine is dipped in the cold F127 solution. The needle sucks up the liquid. The pericardial tissue is placed on a hot plate maintained at 37-40 degree C. simulating live tissue temperature. The oscillating needle with the solution is then used to deposit the solution in the tissue maintained at 37 degree C. The infused solution droplets undergo thermoreversible gelation in the tissue due to change in temperature (temperature change from 0-10 degree C. to 37 degree). C). The thermoreversible Pluronic gel particle release the drug in a sustained manner. The needle may be kept cold by blowing cold air on the needle during insertion.

In another modification of the above example, a thermoreversible polymer that forms solution when warmed around 40-65 degree C. but forms gel when cooled to body temperature or room temperature is used. A gelatin grade that is soluble in hot water but not in cold or body temperature water is used. Briefly 2 g of gelatin, 98 g PBS and 10 mg indocyanine green as a green colorant is used. The hot gelatin solution (40-60 degree C.) of gelatin is deposited inside the tissue using oscillating needle of a tattoo machine as described before. The gelatin droplets undergo cooling and therefore gelation in the deposited tissue. If drug is added in the gelatin, it is released by the gelled particle in a sustained manner.

Some PEG-polylactone polymers (known in the prior art) also show thermoreversible gelation similar to gelatin and such polymer may also be used to deposit in the live tissue and for sustained drug delivery.

Example 15

Delivery of Low Melting Compositions Using Oscillating Needle Device

Delivery of Compositions that Form Microparticles In Situ

In a 250 ml glass beaker, 20 g of Pluronic F127 and 0.1 g of chlorhexidine acetate and 10 mg of ethyl eosin are added and mixed. The mixture is heated to 60-80 degree C. in an oil bath until F127 polymer melts. The melted polymers is mixed thoroughly with chlorhexidine diacetate salt hydrate and cooled and pulverized using mortar pastel. The melted drug polymer composition is re-melted in an oil bath maintained at 60 degree C. and used for deposition in the bioprosthesis tissue or in the live tissue using oscillating needle apparatus such as tattoo machine. Briefly, a new sterile tattoo needle is attached to the tattoo machine and the machine is started/powered. The oscillating needle of the tattoo machine is dipped in melted F127 composition and the hot liquid polymer is deposited in the pericardial tissue using the oscillating needle (tattooed the tissue). Care is taken to avoid premature cooling of the melted solid. If necessary hot air may be blown using a hair dryer on the machine/needle to prevent the premature solidification of the composition in the needle. The excess fluid on the surface of the tissue is wiped and the deposited liquid is allowed to cool. The deposited liquid cools and forms solid microparticles in situ. The drug is released from the solid particles in a sustained manner. In another modification of above example, Pluronic F127 is replaced with lower molecular weight Pluronic F68. In another modification, chlorhexidine acetate is replaced with rifampin or coumarin 6.

In another modification of the above example, polycaprolactone polymer (molecular weight 2000 g/mole) is used for drug delivery and deposition using oscillating needle apparatus. Briefly, in a 100 ml beaker, 9 g polycaprolactone polymer, 1 g rifampin and 10 ml dichlormethane are added until complete homogenous solution (drug weight percent is 10 relative to polymer weight). The methylene chloride is removed by air drying inside the hood leaving behind the polymer and drug. The polymer is vacuum dried over night at 40 degree C. The polymer is heated in oil bath to melt the polycaprolactone at 50-60 degree C. The liquid polymer is filled inside the tattoo machine needle and deposited inside the pericardial tissue surface or live tissue in the shape of a 1 cm diameter circle (tattooed area circle). The excess polymer on the tissue surface is wiped of. The deposited liquid polymer cools and forms solid microparticles inside the tissue.

In another modification of the above embodiment, a bone wax is used in place of polycaprolactone. The wax melts around 60 degree C. and can be injected and cooled to form wax particles. This is a biostable non-polymer or oligomeric composition.

In another modification of the above embodiment, a D-α-Tocopherol polyethylene glycol 1000 succinate is used as low melting polymer is used in place of polycaprolactone.

In another modification of the above embodiment, steric acid is used as a non-polymeric solid in place of polycaprolactone.

In another modification of the above embodiment, a low melting (below 60 degree C) PEG-polylactone or PEG-polycaprolactone polymer is used in place of polycaprolactone.

Example 16

Delivery of Biocompatible Liquid Compositions Using Oscillating Needle Device

Delivery of Compositions that Stay as Liquid Droplets after Deposition

In a 250 ml glass beaker, 20 g vitamin E acetate and 1 rifampin are added. The non-polymeric liquid carrier (vitamin E acetate) is injected in the bioprosthesis tissue or in the live tissue using oscillating needle apparatus such as tattoo machine. Briefly, a new sterile tattoo needle is attached to the tattoo machine and the machine is started/powered. The oscillating needle of the tattoo machine is dipped in the vitamin E acetate composition and deposited in the pericardial tissue using the oscillating needle (tattooed the tissue). The excess fluid on the surface is wiped off. The drug is released from the liquid droplets in a sustained manner.

In another modification of the above example, a biodegradable polymeric liquid (polycaprolactone polymer; molecular weight 520 g/mole) is used for drug delivery and deposition using oscillating needle apparatus. The polymer is liquid at ambient or body temperature. Briefly, in a 100 ml beaker 9 g polycaprolactone polymer and 500 mg rifampin are added until complete homogenous solution/suspension is formed (drug weight percent is 5 relative to polymer weight). The liquid polymer is filled inside the tattoo machine needle and deposited inside the pericardial tissue surface or live tissue in the shape of a 1 cm dia circle (tattooed area circle). The excess polymer liquid is wiped off from the tissue surface. The deposited liquid polymer delivers the drug in a sustained manner. The liquid polymer is removed from the tissue by the biodegradation process.

In another modification of the above embodiment, sucrose acetate isobutyrate solution ethanol or DMSO, a non-polymeric liquid is used in place of polycaprolactone. The solvent DMSO or ethanol is added to modify the viscosity of the sucrose acetate isobutyrate. Only small amount (1-20 percent) solvent is added to make it suitable for injection using the machine. The solvents used (DMSO, ethanol, NMP and the like) preferably are water miscible, biocompatible and biodegradable.

In another modification of the above embodiment, oleic acid, a non-polymeric liquid is used in place of polycaprolactone. This carrier also could also be used with water miscible solvents as described above to adjust its viscosity.

In another embodiment as above, rifampin is replaced with coumarin 6 as model hydrophobic and fluorescent drug and colorant.

Example 17

Delivery of Biocompatible Liquid Compositions that React with the Tissue Fluid Components to Form Water Insoluble Compounds Formation of Silver Halides In Situ In a 250 ml glass beaker, 1 g of silver nitrate solution is dissolved in 99 g distilled deionized water. The solution is sterile filtered. The solution is deposited in the pericardial tissue patch or in the live tissue using a tattoo machine and oscillating tattoo needle. Briefly, a new sterile tattoo needle is attached to the tattoo machine and the machine is started/powered. The oscillating needle of the tattoo machine is dipped in the silver nitrate solution. The needle sucks up the silver nitrate liquid. The needle with the solution is then used to deposit the solution in the tissue. The infused solution droplets react with the chloride ions present naturally in the tissue and forms silver chloride crystals in situ at the injection site. The precipitated silver chloride crystals release silver ion at the local site to prove therapeutic effect by slow dissolution of the salt. Care is taken to protect silver nitrate and silver chloride from light. Light can decompose the silver salt.

In another modification, bovine pericardium tissue is first incubated in 2 percent sodium chloride solution first for two hours. The tissue is then removed, wiped, and is then infused with silver nitrate solution as described before. The incubation in silver chloride assures a constant concentration of chloride ions in the tissue, which enables uniform results. The same can be done for live tissue. The live tissue is washed/wiped with saline solution prior to infusion of silver nitrate solution.

Example 18

Delivery of Botox Solution Using Oscillating Needle Device

Fluorescent Botox Injectable Composition

A commercially available Botox composition is procured. The sterile composition is pooled to make 5 ml Botox solution in 15 ml glass vial. 50 mg of sodium fluorscein is added to the solution. The solution is sterile filtered in sterile polypropylene tube. A oscillating tattoo machine needle is dipped inside the colored and fluorescent Botox solution. The solution is injected in the rat skin via oscillating needle using a tattoo machine. The dose is controlled by turning the oscillation/pulsation on or off by the foot paddle and changing the injecting site. The injected solution is clearly visible via bright fluorescence under blue or white light. The presence of color/fluorescence indicates the presence of Botox and intensity of fluorescence generally indicates the concentration of drug at that site. The fluorscein concentration may be varied 0.01 to 10 percent depending on the brightness of fluorescence desired. Other fluorescent biocompatible dyes that can be used but not limited to: eosin Y, ethyl eosin and the like may also be used.

Example 19

Preparing Microparticles In Situ Using Hand Operated Oscillating Needle 1 g PLGA copolymer, 100 mg rifampin, 10 mg methylene blue or eosin Y as a colorant and 4.9 g DMSO are added in a 50 ml glass beaker with magnetic stirrer. The mixture is stirred until complete dissolution of all ingredients. The mixture is sterile filtered using O.2 micron PTFE filter. The filtered solution is loaded in one ml syringe fitted with 22 gauge needle. A chicken leg piece obtained from local grocery store is used a model surgical local site for injecting the drug. The syringe is hand inserted in the chicken leg tissue at the rate of one injection every three-five seconds (approximately 12-20 injections per minute) while pushing the liquid gently out during insertion. The insertion is made at every approximately 0.5 mm distance along a 1 cm imaginary line at depth of 0.1 to 1 mm. All the injections were into the same 1 cm area and some the injections might have been done at the same site. Total of 20-100 injections are made during this procedure. The excess fluid oozing on the surface is wiped using paper towel. The injected fluid can be clearly seen with a naked eye even after wiping. The portion of tissue where composition is injected is cut from the leg piece and is used in characterizing the particle size of precipitated polymer particle. Another tissue piece prepared in the similar way is used incubated in 5 ml PBS and rifampin release is monitored over a period of one week at 37 degree C. The PBS was exchanged at 1 min, 10 min, 1 h, 2 h, 10 h, 24 h, 2 day, and each day thereafter until 7 days. At each time interval, fresh PBS is exchanged. The drug in the eluted sample is analyzed using HPLC or spectrophotometer.

In another modification of above example, 25 mg PLGA (50:50 polymer, molecular weight 8000-10000 g/mole), 25 mg coumarin 6 as fluorescent colorant and model hydrophobic drug and 0.2 ml DMSO are mixed in 15 ml glass vial. The yellow green solution is hand infused in the chicken leg as described above (total area of deposition 0.5 square cm and total injections around 100). The deposition is made at the rate of 1 injection per second approximately. In another embodiment, the same solution is also infused using oscillating needle apparatus at the rate of 200 oscillations per minute for about 1 minute to compare the method with hand injections. The light colored deposited. The injected compositions showed bright green fluorescence when exposed with blue light.

Example 20

General Method for Injectable Formulation Development

Injectable device Variables: Oscillation frequency, oscillation length, needle diameter (size), needle type (multi lumen or single lumen), area of application, depth of penetration and the like.

Injectable Composition Variable: Type of polymer, polymer molecular weight, polymer concentration, type of solvent, solvent concentration, viscosity of composition, drug concentration, wetting agents type and amount added, microparticle size, microparticle shape and microparticle porosity, microparticle color, and the like.

Test Substrate: Pericardial tissue, transparent or semitransparent thermoreversible gel like gelatin gel (Jell-O like gel cast in a petri dish), live rat skin tissue, chicken leg muscle tissue and the like.

Observations that can be recorded or made by changing various variables as described above include but not limited to: The amount of composition injected per injection, injection volume per injection, droplet size and shape formed, microparticle size and shape formed, depth of penetration, distribution and spacing of particles formed, drug concentration in the injected area, drug release rate in the injected area and the like.

The injected composition in the tissue may be assessed by histology techniques. Briefly the injected area of tissue may be cut and subjected to histological techniques (encapsulating in wax or acrylic cement or frozen tissue), drying, slicing, staining and observing particle size by microscope or scanning electron microscope or electron microscope. A reconstruction of 3 dimensional distribution of particle size can be made from histological data.

The tissue with injected composition or gelatin gel may be dissolved in 4 percent pepsin solution 0.1M HCL for 24 h at 37 degree C. to recover injected particles. The recovered particles may be analyzed for particle size and distribution. Laser light scattering or SEM may be used to assess particle size, distribution and shape. The gelatin gel or thermoreversible may be heated at around 60-70 degree C. or cooled below 10 degree C. to liquefy the gel. The microparticles in the liquefied gel may be filtered and analyzed.

The injected tissue may be isolated and incubated in PBS under sink condition at 37 degree C. to elute encapsulated drug of a period of time. The eluted drug may be analyzed by HPLC, UV-VIS spectrophotometer or other means. Rate of release (drug elution over a period of time) is then constructed from the observed data.

A statistical designed experiment (DOE) may be used to test many variables discussed above, which can help to reduce the number of experiments needed to develop a given injectable composition.

The list of variables and resulting data described above is a partial list only and should not be considered as limitation of this invention.

Example 21

Ophthalmic Drug Delivery Composition

In Situ Deposition of Sustained Drug Delivery Composition in Corneal Tissue

Ten fresh bovine or porcine eyes are obtained from local slaughterhouse. 25 mg PLGA (50:50, molecular weight 8000-10000 g/mole), 25 mg coumarin 6 as fluorescent colorant and a model hydrophobic drug and 0.2 ml DMSO are mixed in 15 ml glass vial. The solution is loaded in a tattoo needle, which is attached to a rotary tattoo machine. The apparatus used is similar to described in FIG. 20. The bovine eye is held by hand the other hand is used to inject the polymer solution in the transparent cornea. The composition is injected around the iris or other transparent area as circular line (circle diameter around 1 cm) or as straight line or as a plus sign. The oscillation speed is maintained 3000 injections per minute and the depth of penetration is kept at 10-200 microns. The excess polymer solution is wiped off using paper napkin. PBS solution is poured on the injected area and any loose material that is not embedded or tattooed in the cornea is wiped of. The deposited solution precipitates in the deposited area and the precipitated polymer/solution is visible as light yellow line. Upon exposing the tattooed line to blue light, the yellow line displays bright green fluoresce indicating successful deposition in the tissue. The drug entrapped in the precipitated polymer releases the coumarin 6 in a sustained manner. In another example, another eye is used to deposit or inject dexamethasone loaded microspheres suspension in PBS (size less than 300 microns, drug loading 30 percent, PLGA 50:50 polymer, molecular weight 50000 g/mole suspended in PBS solution). The implanted tissue is surgically removed from the eye and incubated in 10 ml PBS solution at 27 degree C. under sink conditions and the drug release is monitored for 30 days. Tissues from untreated eyes are also cut and used as a control. The drug elution is monitored by HPLC or UV-ViS spectrophotometer and an elution profile is generated.

In another modification of above example, a circular section of bovine cornea is cut from the eye. The shape and area of the tissue is same as commercially used contact lenses. The tissue is decellularized and then injected with drug delivery composition as described above. The injected cornea can be used as temporary contact lens loaded with sustained drug delivery composition. In another modification of above example, the tissue is crosslinked with 20 mg/ml in PBS pH 7.2 disulfosuccinimidyl suberate for 12 h prior to injection. The disulfosuccinimidyl suberate crosslinking method is known in the prior art.

Example 22

Injection of Fluorescent Composition Using Oscillating Needle Apparatus

Injection of Deposited Patterns in a Muscle Tissue or Bioprosthetic Tissue

In this example, a freshly obtained chicken leg piece is used as a model open surgical tissue for deposition of injectable sustained drug delivery compositions in various shapes or patterns.

25 mg PLGA (50:50, molecular weight 8000-10000 g/mole), 25 mg coumarin 6 as fluorescent colorant and a model hydrophobic drug and 0.2 ml DMSO are mixed in 15 ml glass vial. The solution is loaded in a tattoo needle, which is attached to a rotary tattoo machine similar to described in FIG. 20. The needle tip is dipped into polymer solution and the machine is started by pressing the foot paddle. The vibrating needle (3000 rpm per minute) is used to tattoo or deposit the polymer solution in a plus sign shape or as a circle on the chicken leg muscle. The excess fluid from the muscle surface is wiped off. The water in the muscle tissue precipitates the PLGA polymer and the precipitated polymer along with model drug/colorant is entrapped in the tissue. A saline solution is used to wash the injected surface area. Care is taken to make sure only embedded material stays in place and all surface solution/materials is wiped/washed off or removed. The injected/deposited area is photographed under normal light and under blue light. The deposited material can be clearly seen under both the light conditions but precipitated microparticles shows of much more prominently under the blue light.

In another embodiment, the same composition is embedded/infused using a same apparatus and same parameters in unfixed pericardial tissue and in glutaraldehyde crosslinked porcine submucosa tissue.

Example 23

Bioprosthesis Tissue Crosslinking Using Oscillating Needle Device

Selective Area of the Bioprosthesis Tissue Crosslinked Using Oscillating Needle Device In a 250 ml glass beaker, 1 g PEG10K4ARM glutarate NHS ester purchased from commercial sources is dissolved in 10 ml PBS buffer (20 mM, pH 7.2) along with 1-2 mg of Eosin Y as colorant or sodium fluorscein as fluorescent agent. 10 cm by 10 cm fresh and cleaned bovine pericardium tissue is used for tissue crosslinking. The crosslinker solution is loaded in a tattoo needle, which is attached to a rotary tattoo machine similar to described in FIG. 20. The needle tip is dipped into crosslinker solution and the machine is started by pressing the foot paddle. The vibrating needle (50-3000 rpm per minute) is used to tattoo or deposit the crosslinker solution in a plus sign shape or as a 1 cm diameter circle shape. The solution is also infused in 1 cm by 1 cm area at the center of the tissue in the shape of a solid square. The excess fluid from is wiped off after 30 minutes to 6 h incubation. This tissue incubation with the crosslinker enables the PEG crosslinker to react with extracellular matrix, preferably with collagen matrix. Being a polymeric crosslinker, the diffusion of crosslinker is generally limited to the area of infusion. Collagen proteins exposed to the tissue crosslinker under effective crosslinker conditions crosslinks the tissue. The injected area of the tissue and non-injected area of the tissue is subjected to pepsin digestion test or shrink temperature test. The crosslinked (infused) tissue shows substantial resistance to pepsin digestion and/or shows high shrink temperature relative to not-infused or un-infused tissue indicating that crosslinking can be restricted to infusion area only. By controlling size and area of crosslinker solution infusion, it is possible to create areas of the same bioprosthesis tissue that is crosslinked and therefore biostable or not crosslinked therefore biodegradable. The infusion areas can be of any shape and size such as circle, triangular, symmetric or not symmetric shape or irregular shape. The color in the composition helps to detect the deposited crosslinker solution in the tissue.

In a variation of above example, the PEG glutarate NHS ester may be changed to, PEG succinate NHS ester, PEG adipate NHS ester, PEG suberate NHS ester to obtain crosslinked tissue with various degradation time. The variation is hydrolysis rates of esters in crosslinking agents (succinate, glutarate, adipate, suberate) gives different degradation rates for the crosslinked tissue. The molecular weight of PEG crosslinker may vary from 400-35000, preferably 600-20000 g/mole. The crosslinker must have minimum 2 or more reactive groups per molecule. The crosslinkers may have three, four, five, six, seven, eight or more reactive groups per molecule. The crosslinker may be linear or branched in nature. The effective crosslinking conditions include: 10-100 mg/ml crosslinker concentration which may be dependent on molecular weight, pH 6-8, preferably pH 7.2 in biocompatible buffer like PBS, exposure time 1 minute to 12 h, preferably 30 minutes to 6 h. Other tissue crosslinkers such as glutaraldehyde (0.2 percent solution in PBS pH 7.2, 6 h incubation or more; activated di- or polyhydroxy acids (10-40 mg per ml in PBS or DMSO-water mixture, 10 min-6 h incubation), di or poly epoxides, di-polyisocyanate and the like known in the tissue crosslinking art may also be used. The effective crosslinking conditions must be determined prior to using such crosslinkers. The visualization agent or colorant used in such compositions should not have functional groups that can react with the crosslinker under tissue crosslinking conditions.

Example 24

Tissue Crosslinking Using Oscillating Needle Device

Crosslinking of Corneal Tissue

Crosslinking of Live Tissue Such as Corneal Tissue

Ten fresh bovine or porcine eyes are obtained from local slaughterhouse In a 250 ml glass beaker, 1 g PEG10K4ARM glutarate NHS ester purchased from commercial sources is dissolved in 10 ml PBS buffer along with 2 mg of sodium fluorscein or methylene blue or eosin as visualization/fluorescent agent. The solution is sterile filtered. The crosslinker solution is loaded in a sterile tattoo needle, which is attached to a rotary tattoo machine similar to described in FIG. 20. The needle tip is dipped into crosslinker solution or injectable composition reservoir on the machine filled with the crosslinker solution. The oscillating machine is powered and started by pressing the foot paddle on the machine. The vibrating needle (50-3000 rpm per minute) is used to tattoo or deposit the crosslinker solution in 0.5 cm dia circle shape in the bovine eye. The needle depth penetration is restricted to 10-100 microns only. The tissue is also infused in 5 mm by 5 mm area on the cornea as a solid square. The excess fluid from the tissue surface is wiped off after 30 minutes to 6 h incubation. The tissue incubation with the crosslinker enables the PEG crosslinker to react with extracellular matrix in the cornea, preferably with collagen matrix. Being a polymeric crosslinker, the diffusion of crosslinker is generally limited to the area of infusion deposition. In another eye, entire corneal tissue is infused with the crosslinking solution and incubated for 6 h. The injected area of the cornea tissue is cut and separated and is subjected to pepsin digestion test or shrink temperature test. Untreated corneal tissues from other untreated eyes are used as control untreated tissue. The treated tissue shows substantial resistance to pepsin digestion and/or higher shrink temperature relative to control tissue (untreated tissue) indicating tissue crosslinking.

In another modification of above ambident, one left eye of the live rabbit is infused with crosslinker solution and right eye is used as untreated control. The corneal tissue is then isolated and subjected to pepsin digestion test or shrink temperature tests.

In a variation of above example, disulfosuccinimidyl suberate (DSS) solution (DSS concentration 20 mg/ml in PBS pH 7.2, 0.1 mg ml sodium fluorscein as colorant is infused in place of PEG10K4ARM glutarate NHS ester. This crosslinker produce biostable tissue in the infused area.

Example 25

Prevention of Post-Operative Adhesions by Local Infusion of Polymeric Lubricants Using Injectable Device Described in this Invention A treatment solution is made by dissolving 4 g PEG10K4ARM NHS ester in 96 g PBS pH 7.2 and 10 mg sodium fluorscein as a coloring agent and the solution is sterile filtered. A control solution is made by dissolving 4 g PEG 10000 tetrafunctional with terminal alcohol groups (PEG10K4ARM) in 96 g PBS, pH 7.2 and 10 mg sodium fluorscein as coloring agent and the solution is sterile filtered. 2 groups 30 Sprague Dawley rats (average weight 250-300 G) are used in this experiment. One group is labeled as control and the other group is labeled as treated. The rats are anesthetized, an abdominal incision is made and rat cecum is located. A standard surgical cotton gauze pad is used to make an abrasion injury (abrading the cecum surface by gauze, injury area 0.5 to 2 sq. cm). The injury may cause mild bleeding on the injured surface. Either treatment or control solution is infused using oscillating needle device described in this invention (Example 23 or 24 for illustrative device conditions) on the entire secum surface. The infusion is limited to 10-100 microns dip. Excess solution is dabbed away and the animal is closed, ear tagged for identification and maintained on standard diet for 14 days. After 14 days, the rats are subjected to CO2 asphyxiation and the animals are opened to see the post-operative adhesions formed in the abdomen. The adhesions formed are graded on the scale from 1 to 3 for number of adhesions as well as severity of adhesions (zero for no adhesion, 1 for tiny adhesion, 2 for small adhesion and 3 for severe adhesions). The scores for adhesions are used to compare treated versus control group using t-test.

In a similar experiment as above, 1 percent sodium hyaluronate along with 0.1 percent sodium fluorscein or 1 percent indocyanine green is as a treatment solution. The saline solution along with same concentration of colorant is used as a control solution. Both solutions are infused using oscillating needle device.

In another modification of above example, PLGA microparticles or PEG based degradable hydrogel particles (particle size less than 300 microns) with 10 percent tissue plasminogen activator (TPA) as a drug loading, sustained releasing for 2-7 days is used to infuse in the secum. The control sample is infused with saline solution only. The treated and untreated groups are compared for surgical adhesion formation as mentioned previously.

Although the present invention has been particularly shown and described with reference to exemplary embodiments thereof, it will be understood by those of ordinary skill in the art that various changes in form and details may be made therein without departing from the spirit and scope of the present invention as defined by the appended claims. Therefore, the present embodiments are to be considered as illustrative and not restrictive and the invention is not to be limited to the written description.

REFERENCES

The following references, to the extent that they provide exemplary procedural or other details supplementary to those set forth herein, are specifically incorporated herein by reference:
1. Purification of Laboratory Chemicals; D. D. PERRIN, Butterworth-Heinemann; 4th edition.
2. E. Khor, Biomaterials, Volume 18, Page 95 (1997)
3. Brandrup, J et al. (Editor) "Polymer Handbook" 4th Edition, John Wiley & Sons. (2005)
4. J. Antony, "Design of Experiments for Engineers and Scientists", Elsevier (2003)
5. Roberts et al. Advanced Drug Delivery Reviews, Volume 54, 459-476 (2002 R. P.
6. Patel R. P. et. al.; R. J. of Pharmaceuticals, Volume 01, Page 65, (2011)

The invention claimed is:
1. A method for delivering an injectable composition at a local site in a tissue, the method comprising:
providing an injectable composition having a bioactive agent; and
injecting the injectable composition in the tissue at an amount of 1.0E-03 ml to 1.0E-16 ml per injection,
wherein the bioactive agent is encapsulated in a plurality of biodegradable microparticles, the microparticles being dispersed in a fluid carrier.
2. The method according to claim 1, wherein the microparticles in the injectable composition have an average particle size in the range of 500 nm to 300 microns.
3. The method according to claim 2, wherein the microparticles in the injectable composition are of substantially spherical, semispherical, elliptical, circular disk, or irregular shape.
4. The method according to claim 1, wherein the fluid carrier of the injectable composition is an aqueous based medium.
5. The method according to claim 1, wherein the injected microparticles are deposited in a pre-determined two or three-dimensional pattern in the tissue.
6. The method according to claim 1, wherein the microparticles have a visualization agent.
7. The method according to claim 6, wherein the visualization agent is a coloring composition, a fluorescent composition or a radio opaque contrast agent or an NMR contrast agent.
8. The method according to claim 1, wherein the biodegradable microparticles are prepared from a biodegradable polymer selected from a group comprising of polymers, dendramers, copolymers or oligomers of glycolide, dl-lactide, d-lactide, l-lactide, caprolactone, dioxanone and trimethylene carbonate; degradable polyurethanes; polyamides; polyesters; polypeptides; polyhydroxyacids; polyorthocarbonates, polylactic acid; polyglycolic acid; polyanhydrides; and polylactones.
9. The method of claim 1, wherein the injectable composition is injected in the tissue at a depth of 10 microns to 5 mm.

* * * * *